(12) United States Patent
Williams et al.

(10) Patent No.: US 8,790,704 B2
(45) Date of Patent: *Jul. 29, 2014

(54) COMBINATION PEPTIDE-NANOPARTICLES AND DELIVERY SYSTEMS INCORPORATING SAME

(75) Inventors: Phillip Williams, Botley (GB); Thomas Rademacher, Boars Hill (GB); Alexander Mark Schobel, Whitehouse Station, NJ (US); Eric Dadey, Furlong, PA (US)

(73) Assignees: Monosol RX, LLC, Warren, NJ (US); Midatech Limited, Abingdon, Oxfordshire (GB)

( * ) Notice: Subject to any disclaimer, the term of this patent is extended or adjusted under 35 U.S.C. 154(b) by 0 days.

This patent is subject to a terminal disclaimer.

(21) Appl. No.: 13/492,040

(22) Filed: Jun. 8, 2012

(65) Prior Publication Data

US 2012/0301535 A1  Nov. 29, 2012

Related U.S. Application Data

(63) Continuation-in-part of application No. 13/157,783, filed on Jun. 10, 2011, now Pat. No. 8,568,781, and a continuation-in-part of application No. 13/157,836, filed on Jun. 10, 2011, and a continuation-in-part of application No. PCT/GB2011/000882, filed on Jun. 10, 2011, and a continuation-in-part of application No. PCT/US2011/039979, filed on Jun. 10, 2011.

(60) Provisional application No. 61/570,598, filed on Dec. 14, 2011, provisional application No. 61/353,380, filed on Jun. 10, 2010, provisional application No. 61/353,366, filed on Jun. 10, 2010.

(51) Int. Cl.
| | | |
|---|---|---|
| A61K 9/14 | (2006.01) | |
| A61K 38/00 | (2006.01) | |
| A61K 38/28 | (2006.01) | |
| C07K 5/00 | (2006.01) | |
| C07K 7/00 | (2006.01) | |
| A61K 47/48 | (2006.01) | |

(52) U.S. Cl.
CPC ........ *A61K 47/48861* (2013.01); *Y10S 977/773* (2013.01); *Y10S 977/795* (2013.01); *Y10S 977/838* (2013.01); *Y10S 977/906* (2013.01)
USPC .............. 424/489; 514/1.1; 514/6.8; 514/6.9; 530/303; 530/304; 530/308; 977/773; 977/795; 977/838; 977/906

(58) Field of Classification Search
USPC ........... 424/489; 530/303, 304, 308; 977/773, 977/795, 838, 906; 514/1.1, 6.8, 6.9
See application file for complete search history.

(56) References Cited

U.S. PATENT DOCUMENTS

| 7,179,788 B2 | 2/2007 | DeFelippis et al. |
| 7,531,191 B2 | 5/2009 | Zion et al. |

(Continued)

OTHER PUBLICATIONS

Written Opinion/Search Report from the PCT application mailed Aug. 17, 2012.

(Continued)

*Primary Examiner* — Blessing M Fubara
(74) *Attorney, Agent, or Firm* — Hoffmann & Baron, LLP

(57) ABSTRACT

Nanoparticles having a core and a corona of ligands covalently linked to the core, wherein differing species of peptides are bound to the nanoparticles and incorporated into various dosage forms.

74 Claims, 32 Drawing Sheets

(56) References Cited

U.S. PATENT DOCUMENTS

| | | | |
|---|---|---|---|
| 8,568,781 B2 * | 10/2013 | Rademacher et al. | ........ 424/489 |
| 2004/0058457 A1 | 3/2004 | Huang et al. | |
| 2008/0300173 A1 | 12/2008 | DeFrees | |
| 2009/0192075 A1 | 7/2009 | Steiner | |
| 2009/0297614 A1 | 12/2009 | Rademacher et al. | |
| 2010/0221309 A1 | 9/2010 | Myers et al. | |

* cited by examiner

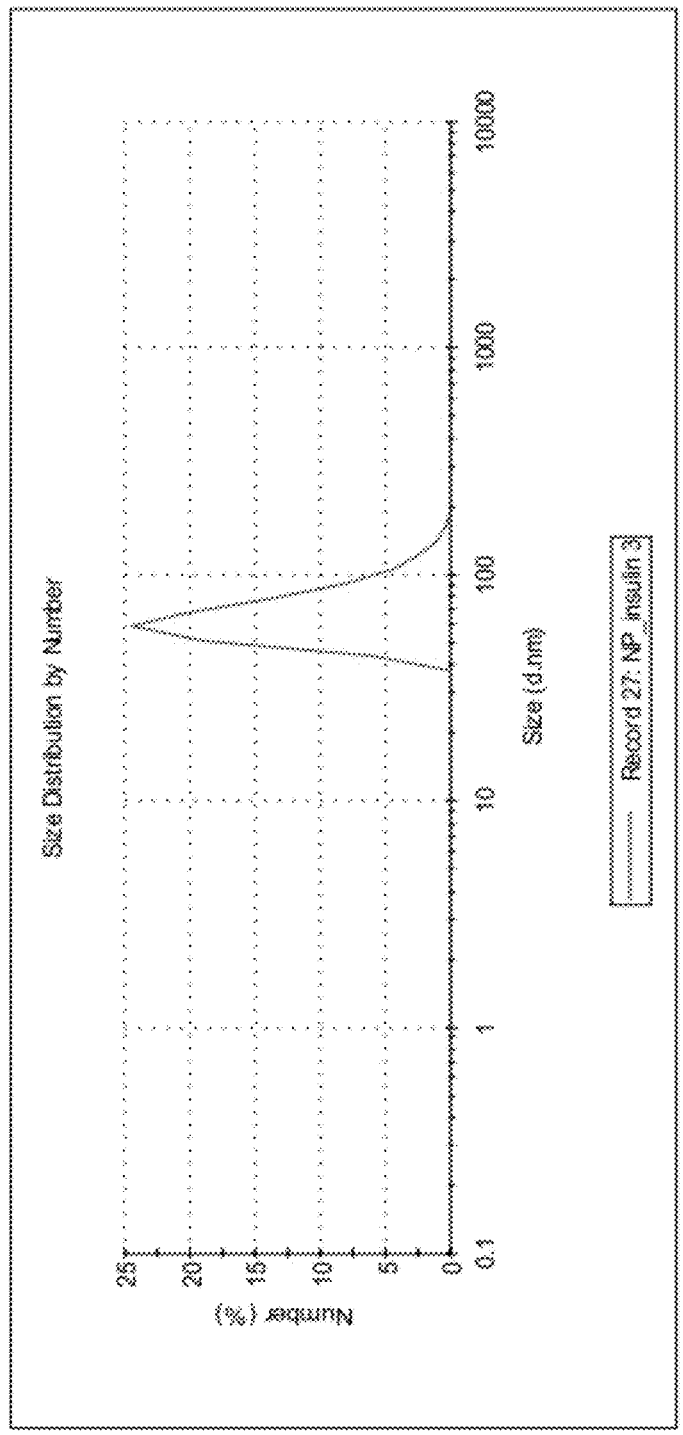

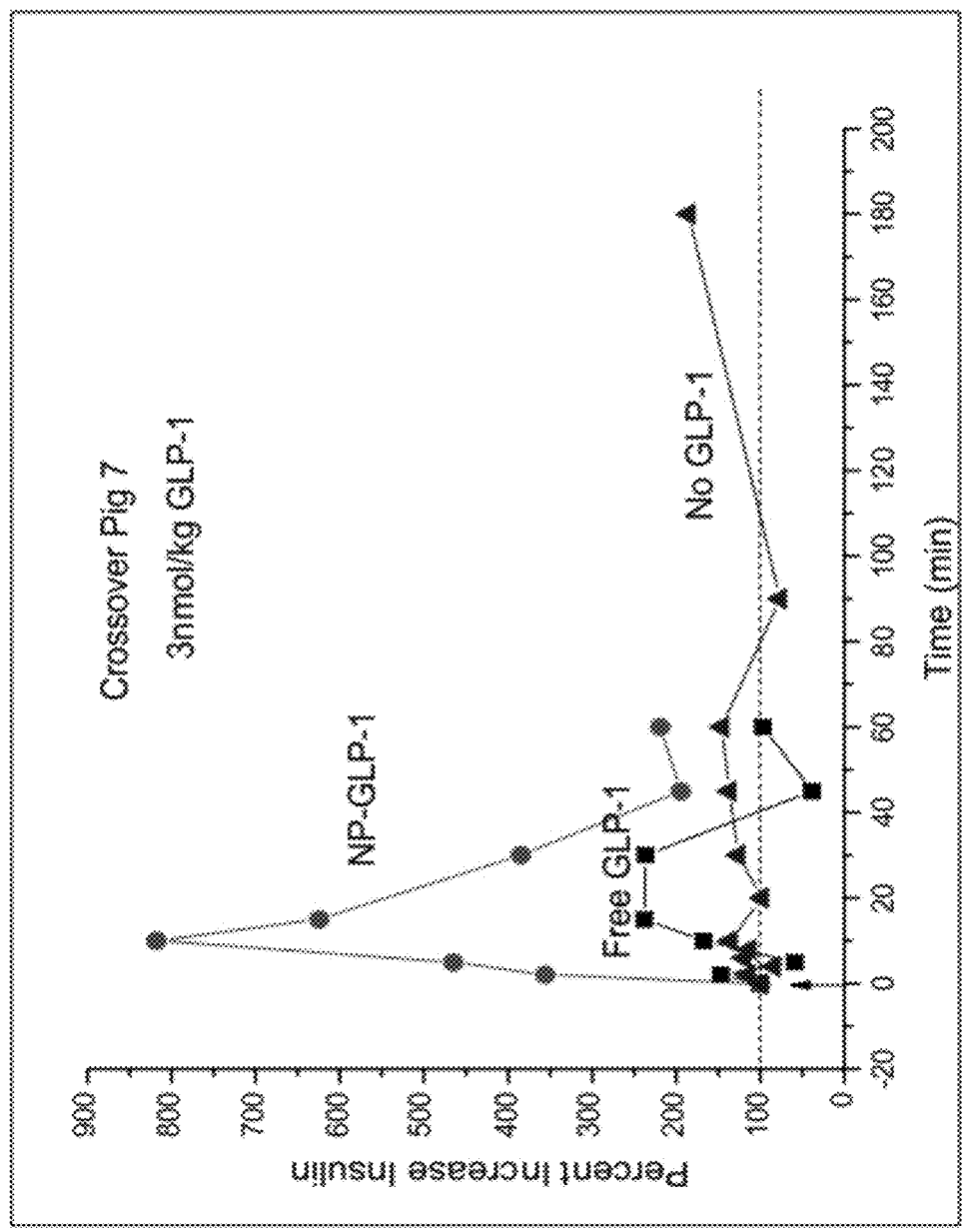

COMBINATION PEPTIDE-NANOPARTICLES AND DELIVERY SYSTEMS INCORPORATING SAME

CROSS-REFERENCE TO RELATED APPLICATIONS

The present invention claims priority to U.S. Provisional Application No. 61/570,598, filed Dec. 14, 2011, and claims priority to International Application No. PCT/US2011/39979, filed Jun. 10, 2011, and claims priority to International Application No. PCT/GB2011/000882, filed Jun. 10, 2011, and claims priority to U.S. application Ser. No. 13/157,836, filed Jun. 10, 2011, which claims priority to U.S. Application No. 61/353,366, filed Jun. 10, 2010, and claims priority to U.S. application Ser. No. 13/157,783, filed Jun. 10, 2011, which claims priority to U.S. Application No. 61/353,380, filed Jun. 10, 2010, the entire contents of each of which are incorporated by reference herein.

The subject matter of this application was made by or on behalf of MonoSol Rx, LLC and Midatech Limited pursuant to a joint research agreement. The joint research agreement was in effect before the date the present invention was made, and the invention was made as a result of activities undertaken within the scope of the joint research agreement.

FIELD OF THE INVENTION

The present invention relates to bioactive particles, particularly for use in medicine, and includes methods for treatment of disorders, e.g., of blood glucose regulation.

BACKGROUND TO THE INVENTION

The present invention is directed at compositions and products, and methods of making and administering such compositions and products, including for the treatment of mammals and particularly humans.

Bioactive agents, such as peptides, frequently suffer from poor stability, particularly thermo-stability, which may limit the conditions to which the agents can be subjected during preparation, processing, storage and/or delivery. For example, insulin is widely-used in the control and treatment of, e.g., Type 1 & Type 2 diabetes mellitus. Medical preparations of insulin for human use are generally formulated with one or more preservatives and/or stabilisers. Moreover, limited gastrointestinal stability typically presents a barrier to effective oral administration of bioactive peptides, such as insulin.

Bioactive agents such as peptide hormones frequently exhibit sub-optimal pharmacokinetic and/or pharmacodynamic properties when administered by conventional methods and delivery systems. Moreover, administration of combinations of bioactive agents is significantly complicated by varying, and often poorly-matched, pharmacokinetic and/or pharmacodynamic profiles of each of the individual actives that make up the combination.

There remains an unmet need for compositions for delivery of combinations of bioactive peptides that exhibit a more desirable treatment profile.

BRIEF DESCRIPTION OF THE INVENTION

The present invention addresses the aforementioned difficulties by providing a combination active-carrying compositions for delivery of active agents such as peptides.

The present invention provides nanoparticles which as described herein, include a metal and/or semiconductor core, a corona of ligands and a combination of two or more differing bioactives bound to the corona. The two or more differing bioactives are thereby brought into relatively close association at a molecular level. As described in further detail herein, the concomitant bioactives, bound to a common nanoparticle, display novel and desirable pharmacodynamic and pharmacokinetic properties.

Accordingly, in a first aspect the present invention provides a nanoparticle comprising:
 (i) a core comprising a metal and/or a semiconductor;
 (ii) a corona comprising a plurality of ligands covalently linked to the core, wherein at least one of said ligands comprises a carbohydrate moiety; and
 (iii) at least two different species of peptide bound to the corona.

In a further aspect the present invention provides a plurality of nanoparticles of the invention.

In a further aspect, the present invention provides a pharmaceutical composition, formulation or dosage unit comprising a plurality of nanoparticles of the invention and one or more pharmaceutically acceptable carriers or excipients.

In a further aspect, the present invention provides a method of modifying at least one pharmcodynamic and/or pharmacokinetic property of a combination of at least two different peptides, the method comprising:
 contacting the combination of at least two peptides with a nanoparticle under conditions which allow the at least two peptides to bind to the nanoparticle.

In a further aspect, the present invention provides a method for enhancing the bioavailability of insulin and/or reducing the pancreatic insulinotropic effect of GLP-1 upon administration of the GLP-1 to a mammalian subject, the method comprising:
 contacting both insulin and GLP-1 with a nanoparticle as under conditions which allow the insulin and the GLP-1 to bind to the nanoparticle, thereby forming a nanoparticle having both insulin and GLP-1 bound thereto.

In a further aspect, the present invention provides a method of lowering blood glucose in a mammalian subject in need thereof, comprising administering a therapeutically effective amount of a nanoparticle of the invention.

In a further aspect, the present invention provides a method of treating diabetes in a mammalian subject in need thereof, comprising administering a therapeutically effective amount of a nanoparticle of the invention.

In a further aspect, the present invention provides a nanoparticle of the invention for use in a method of medical treatment.

In a further aspect, the present invention provides a nanoparticle of the invention for use in a method of treatment of diabetes in a mammalian subject.

In a further aspect, the present invention provides use of nanoparticle of the invention in the preparation of a medicament for use in a method of treatment of diabetes.

In a further aspect, the present invention provides an article of manufacture comprising:
 at least one nanoparticle of the invention;
 a container for housing the at least one nanoparticle; and
 an insert and/or a label.

In a further aspect, there is provided a therapeutic or bioaffecting film delivery system comprising: (a) one or more film matrices comprising at least one polymer; (b) a plurality of nanoparticles incorporated in at least one of said film matrices, said nanoparticles comprising: (i) a core comprising a metal and/or a semiconductor; (ii) a corona comprising a plurality of ligands covalently linked to the core, wherein at least one of said ligands comprises a carbohydrate moiety; and (iii) at least two different species of peptide bound to the corona.

In a further aspect, there is provided a insulin-containing film delivery system comprising: (a) one or more film matrices comprising at least one polymer; (b) a plurality of nanoparticles incorporated in at least one of said film matrices, said nanoparticles comprising: (i) a core comprising a gold; (ii) a plurality of ligands covalently attached to the core and forming a corona around the core, wherein the ligands comprise 2'-thioethyl-α-D-galactopyranoside and 1-amino-17-mercapto-3,6,9,12,15,-pentaoxa-heptadecanol each bonded to the core via their respective sulphur atoms, and wherein the nanoparticles have an average of at least five insulin monomers bound per nanoparticle core and (ii) at least one GLP-1 molecule or GLP-1 analogue molecule bound per nanoparticle core.

In a further aspect, there is provided a process for making a film having a substantially uniform distribution of components, comprising the steps of: (a) forming a flowable polymer matrix comprising a water-soluble or water swellable polymer, a solvent and an active-carrying component, said active-carrying component comprising a plurality of nanoparticles comprising: (i) a core comprising a metal; (ii) a corona comprising a plurality of ligands covalently linked to the core, wherein at least one of said ligands comprises a carbohydrate moiety; and (iii) at least two different species of peptide bound to the corona; said matrix having a substantially uniform distribution of said active; (b) casting said flowable polymer matrix; (c) evaporating at least a portion of said solvent from said flowable polymer matrix to form a visco-elastic film within about 10 minutes or fewer to maintain said uniform distribution of said active by locking-in or substantially preventing migration of said active within said visco-elastic film; and (d) forming a resulting film from said visco-elastic film, wherein said resulting film has a water content of 10% or less and said substantially uniform distribution of active by said locking-in or substantially preventing migration of said active is maintained.

In a further aspect, there is provided a process for making a film having a substantially uniform distribution of components, comprising the steps of: (a) forming a masterbatch pre-mix comprising a solvent and a polymer selected from the group consisting of water-soluble polymers, water-swellable polymers and combinations thereof; (b) adding an active-carrying component to a pre-determined amount of said masterbatch pre-mix to form a flowable polymer matrix, said active-carrying component comprising a plurality of nanoparticles comprising: (i) a core comprising a metal; (ii) a corona comprising a plurality of ligands covalently linked to the core, wherein at least one of said ligands comprises a carbohydrate moiety; and (iii) at least two different species of peptide bound to the corona; said matrix having a substantially uniform distribution of said active; (c) casting said flowable polymer matrix; (d) evaporating at least a portion of said solvent from said flowable polymer matrix to form a visco-elastic film within about 10 minutes or fewer to maintain said uniform distribution of said active-carrying component by locking-in or substantially preventing migration of said active within said visco-elastic film; and (e) forming a resulting film from said visco-elastic film, wherein said resulting film has a water content of 10% or less and said uniform distribution of active-carrying component by said locking-in or substantially preventing migration of said active-carrying component is maintained.

In a further aspect, there is provided an article of manufacture comprising at least one film comprising: (a) one or more film matrices comprising at least one polymer; (b) a plurality of nanoparticles incorporated in at least one of said film matrices, said nanoparticles comprising: (i) a core comprising a metal; (ii) a corona comprising a plurality of ligands covalently linked to the core, wherein at least one of said ligands comprises a carbohydrate moiety; and (iii) at least two different species of peptide bound to the corona; and said at least one film has a water content of about 10% or less by weight of the at least one film and a variance per unit volume of the plurality of nanoparticles or active carried by the nanoparticles of no greater than about 10% or less.

In a further aspect, there is provided a method of reducing the glucose excursion in a mammal comprising administering a composition comprising a nanoparticle comprising: (i) a core comprising a metal and/or a semiconductor; (ii) a corona comprising a plurality of ligands covalently linked to the core, wherein at least one of said ligands comprises a carbohydrate moiety; and (iii) at least two different species of peptide bound to the corona. The peptides preferably comprise: (i) insulin or a suitable analogue thereof; and (ii) GLP-1 or a suitable analogue thereof as well as exenatide and its suitable analogues thereof. The glucose excursion is preferably reduced such that the maximum blood glucose concentration (glucose $C_{max}$") following a glucose challenge is not more than 2.5 times, not more than 2 times or not more than 1.75 time baseline glucose prior to the glucose challenge. Thus, the method may comprise flattening the glucose excursion in response to a glucose challenge such that the glucose excursion is in the control range exhibited by healthy non-diabetic subjects when subject to the same glucose challenge.

In a further aspect, there is provided a method of controlling glucose excursion in a patient while maintaining a substantially normal glucagon response, comprising: administering a composition comprising a nanoparticle comprising: (i) a core comprising a metal and/or a semiconductor; (ii) a corona comprising a plurality of ligands covalently linked to the core, wherein at least one of said ligands comprises a carbohydrate moiety; and (iii) at least two different species of peptide bound to the corona.

In a further aspect, there is provided a method of controlling the release of endogenous insulin in the body such that an insulinotropic effect is substantially reduced comprising, administering a composition comprising a nanoparticle comprising: (i) a core comprising a metal and/or a semiconductor; (ii) a corona comprising a plurality of ligands covalently linked to the core, wherein at least one of said ligands comprises a carbohydrate moiety; and (iii) at least two different species of peptide bound to the corona.

Peptide-carrying nanoparticles are described in unpublished international patent application No. PCT/GB2011/000882, filed 10 Jun. 2011, and U.S. patent application Ser. No. 13/157,783, filed 10 Jun. 2011, the entire contents of which are expressly incorporated herein for all purposes.

Nanoparticle film delivery systems are described in unpublished international application No. PCT/US2011/39979, filed 10 Jun. 2011, and U.S. patent application Ser. No. 13/157,836, filed 10 Jun. 2011, the entire contents of which are expressly incorporated herein for all purposes.

The present invention includes the combination of the aspects and preferred features described except where such a combination is clearly impermissible or is stated to be expressly avoided. These and further aspects and embodiments of the invention are described in further detail below and with reference to the accompanying examples and figures.

BRIEF DESCRIPTION OF THE FIGURES

FIG. 36 shows plots of percent increase in insulin levels following i.v. infusion of: NP-GLP-1 (circles); free GLP-1 (squares); and NP-insulin (triangles), simultaneous with a glucose infusion.

DETAILED DESCRIPTION OF THE INVENTION

Figure 1:
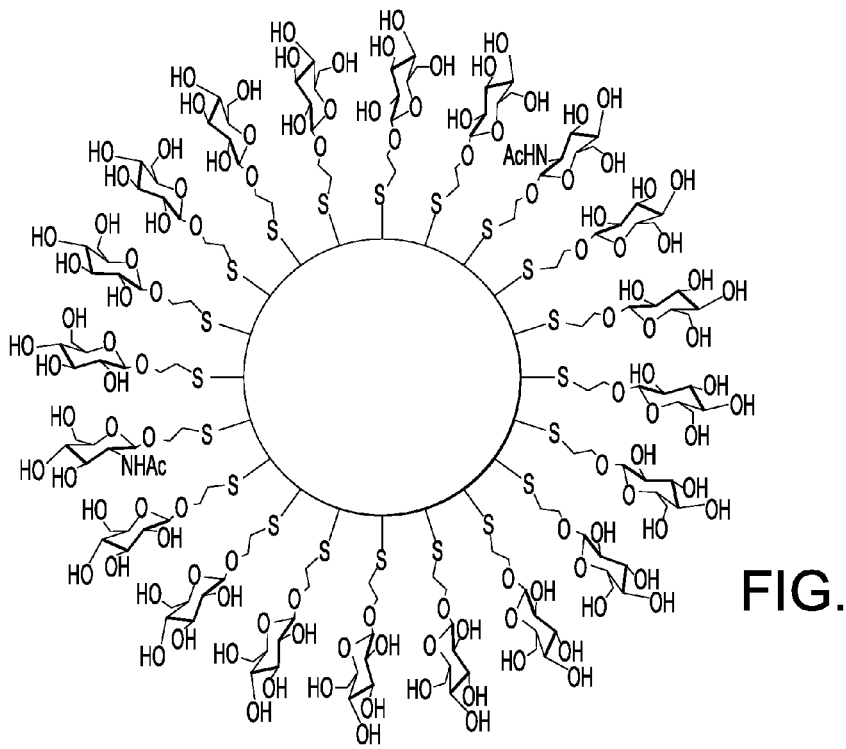
FIG. 1 shows a schematic representation of nanoparticles having a plurality of ligands in the ratio 9:1 of GlcC2:GlcNAc "NP-GlcC2(9)GlcNAc(1)"

In describing the present invention, the following terms will be employed, and are intended to be defined as indicated below.

As used herein, "nanoparticle" refers to a particle having a nanomeric scale, and is not intended to convey any specific shape limitation. In particular, "nanoparticle" encompasses nanospheres, nanotubes, nanoboxes, nanoclusters, nanorods and the like. In certain embodiments the nanoparticles and/or nanoparticle cores contemplated herein have a generally polyhedral or spherical geometry.

Nanoparticles comprising a plurality of carbohydrate-containing ligands have been described in, for example, WO 2002/032404, WO 2004/108165, WO 2005/116226, WO 2006/037979, WO 2007/015105, WO 2007/122388, WO 2005/091704 (the entire contents of each of which is expressly incorporated herein by reference) and such nanoparticles may find use in accordance with the present invention. Moreover, gold-coated nanoparticles including a magnetic core of iron oxide ferrites (having the formula $XFe_2O_4$, where X=Fe, Mn or Co) are described in European patent application publication No. EP2305310, the entire contents of which are expressly incorporated herein by reference, and may find use in accordance with the present invention.

As used herein, "corona" refers to a layer or coating, which may partially or completely cover the exposed surface of the nanoparticle core. The corona includes a plurality of ligands which include at least one carbohydrate moiety. Thus, the corona may be considered to be an organic layer that surrounds or partially surrounds the metallic core. In certain embodiments the corona provides and/or participates in passivating the core of the nanoparticle. Thus, in certain cases the corona may include a sufficiently complete coating layer substantially to stabilise the metal-containing core. However, it is specifically contemplated herein that certain nanoparticles having cores, e.g., that include a metal oxide-containing inner core coated with a noble metal may include a corona that only partially coats the core surface.

As used herein, "peptide" is intended to encompass any sequence of amino acids and specifically includes peptides, polypeptides proteins (including proteins having secondary, tertiary and/or quaternary structure) and fragments thereof. The expression "peptide bound to" is specifically intended to encompass a part (but may include the whole) of the amino acid sequence of the peptide forming a bonding interaction with one or more parts (such as a chemical group or moiety) of one or more of the plurality of ligands of the nanoparticle. In certain embodiments the peptide may have a molecular weight of <500 kDa, <100 kDa, <50 kDa, such as up to 20 kDa.

The term "bound" is intended to include a physical and/or a chemical association between two components. This term includes any form of chemical linkage, e.g., covalent, ionic, hydrogen bonding or intermolecular forces, such as van der Waals forces or electrostatic forces. The term includes physical coupling or linking. This physical and or chemical association may be intended to be reversible, i.e., the component may be separated or disassociated, one from the other, e.g., to release the active component from the carrier component.

As used herein the term "carbohydrate" is intended to include compounds of the general formula $C_n(H_2O)_m$ where n=m and n is greater than 3. Also, included within the definition of carbohydrate are carbohydrate analogues/mimetics that are not included in the general formula $C_n(H_2O)_m$. The carbohydrate analogues/mimetics include but are not limited to pseudo-sugars (carba-sugars), amino-sugars, imino-sugars and inositols. Amino-sugars include polyhydroxylated piperidines, pyrrolidines, pyrrolizidines and indolizidines.

The phrases "uniformity of active" and "uniformity of active content" are intended to mean that the active is present in the product in an amount such that substantially equally sized dosage units can be prepared from the manufactured product, or some division of, and that the dosage units will not vary in their active content when compared to each other by more than about 10% by weight. That is, the variance of active content from dosage unit to dosage unit is about 10% or less. The phrases "uniformity of active" and "uniformity of active content" are intended to be distinct and separate from other physical properties of uniformity, such as visual uniformity. Visual uniformity may include, for example, a uniform, smooth or glossy appearance, or ability to reflect light, none of which relate directly to the content of the film. For example, the properties of being "mottle free" or being "glossy" relate to surface appearance and shininess, respectively. These properties do not indicate that the content in the product is uniform. Although a product, such as a film, may be mottle-free or glossy, it may not necessarily be uniform in its active content. The converse may also be true. It is possible, of course, that a film product may have each of the uniformity properties outlined above, but each property is distinct and is not dependent upon the others.

As used herein, the term "degradation temperature" is intended to mean a temperature at which some degree of degradation of an active occurs. Actives, such as pharmaceuticals and biological actives, are known to degrade over a range of various temperatures and in the presence of other materials. The term "degradation temperature" is not necessarily the temperature at which degradation of the active begins, but is intended to include a range of temperatures at which some degradation of an active component occurs or continues to occur, alone or in the presence of other materials. Any temperature at which degradation of the active occurs is included in this term.

As used herein the term "film" includes delivery systems of any thickness, including films, sheets, discs, wafers, and the like, in any shape, including rectangular, square, or other desired shape. The film may be in the form of a continuous roll of film or may be sized to a desired length and width. The films described herein may be any desired thickness and size suitable for the intended use. For example, a film of the present invention may be sized such that it may be placed into the oral cavity of the user. Other films may be sized for application to the skin of the user, i.e., a topical use. For example, some films may have a relatively thin thickness of from about 0.1 to about 10 mils, while others may have a somewhat thicker thickness of from about 10 to about 30 mils. For some films, especially those intended for topical use, the thickness may be even larger, i.e., greater than about 30 mils. It will be understood, of course, that the thickness of the film may be limited due to the formulation used, and thicker films may require longer drying times. Further, thicker films may desirably be formed through lamination of thinner films. In addition, the term "film" includes single-layer compositions as well as multi-layer compositions, such as laminated films, coatings on films and the like. The composition in its dried film form maintains a uniform distribution of components through the application of controlled drying of the film. Films may include a pouch or region of drug between two films.

The active components used herein may be formed as part of a film delivery system. In this fashion, the active components described herein may be dispersed throughout the film, or may be deposited onto one or more surfaces of the film. In either way, the amount of nanoparticles per unit area is desirably substantially uniform throughout the film. It is desired that the films of the present invention include a uniformity of component distribution throughout the volume of a given film. Such uniformity includes a substantially uniform amount of nanoparticles per unit volume of the film, whether the nanoparticles are within the matrix of the film or coated, laminated, or stabilized on one or more surfaces thereof.

When such films are cut into individual units, the amount of nanoparticles in the unit can be known with a great deal of accuracy.

Uniformity of components throughout the film is beneficial in administering an accurate and effective dose to a user. Various methods of forming uniform films, as well as various additives and fillers, may be used, including those methods and materials described in U.S. Pat. Nos. 7,425,292, 7,357,891, and 7,666,337, which are herein incorporated by reference in their entireties. In some particularly desirable embodiments, the amount of active-carrying component, or the amount of active per se, per unit volume does not vary more than about 10%, as discussed above. Thus a large sheet of film may be made and equally sized dosage units cut therefrom and the amount of active-carrying component or active per se in each dosage unit will not vary more than 10% by weight between units.

The present invention provides a nanoparticle comprising:
(i) a core comprising a metal and/or a semiconductor;
(ii) a corona comprising a plurality of ligands covalently linked to the core, wherein at least one of said ligands comprises a carbohydrate moiety; and
(iii) at least two different species of peptide bound to the corona. Said at least two different species of peptide may be reversibly and/or non-covalently bound to the corona.

The combination of peptides may be bound to the corona such that at least a fraction, or more, of each of the bound peptides is released from the nanoparticle upon contacting the nanoparticle with a physiological solution, e.g. a saline solution. The release may facilitate biological effects of the active peptides, for example by allowing the peptides to interact with their biological receptors. Generally, the peptides will be bioactive peptides, i.e. capable of stimulating a physiological response in a mammalian subject. In some cases in accordance with the present invention, each of the at least two different species of peptide may be independently selected from the group consisting of: insulin, glucagon-like peptide-1 ("GLP-1"; including without limitation GLP-1 (7-37) and GLP-1-(7-36)NH$_2$), IGF1, IGF2, relaxin, INSL5, INSL6, INSL7, pancreatic polypeptide(PP), peptide tyrosine tyrosine (PTT), neuropeptide Y, oxytocin, vasopressin, GnRH, TRH, CRH, GHRH/somatostatin, FSH, LH, TSH, CGA, prolactin, ClIP, ACTH, MSH, enorphins, lipotropin, GH, calcitonin, PTH, inhibin, relaxin, hCG, HPL, glucagons, somatostatin, melatonin, thymosin, thmulin, gastrin, ghrelin, thymopoietin, CCK, GIP secretin, motin VIP, enteroglucagon, IGF-1, IGF-2, leptin, adiponectin, resistin Osteocalcin, renin, EPO, calicitrol, ANP, BNP, chemokines, cytokines, adipokines, PYY(3-36), oxyntomodulin and all suitable biologically active analogues of any one of the peptides listed herein. Thus, in certain cases one or more of the peptides may be capable of stimulating a reduction in blood glucose levels in a mammalian subject. For example, one of the peptides may comprise or consist of monomeric and/or dimeric human insulin or a suitable analogue of human insulin. Furthermore, in some cases one of the peptides may comprise or consist of GLP-1 or a suitable analogue thereof. In certain cases, the combination may be a combination of (i) insulin or an insulin analogue; and (ii) GLP-1 or a suitable GLP-1 analogue as well as exenatide and its suitable analogues thereof. A number of suitable GLP-1 analogues are known in the art, and may find use in accordance with any aspect of the present invention.

As described herein, the present inventors have found that the in vivo biological effects of a nanoparticle having both insulin and GLP-1 bound to the corona of the same nanoparticle differ from those exhibited by a mixture of a first nanoparticle having insulin bound to its corona and a second nanoparticle having GLP-1 bound to its corona. The combination nanoparticle with both insulin and GLP-1 bound to the corona (NP-insulin/GLP-1) exhibits pharmacodynamic and pharmacokinetic properties that are distinct from the aforementioned mixture, and which are in many respects superior from a therapeutic standpoint. The combination NP-insulin/GLP-1 particle may advantageously exhibit one or more properties selected from: reduced glucose excursion in response to a glucose challenge, enhanced biodistribution of insulin, enhanced glucagon response, a decreased in situ pancreatic insulinotropic effect, when administered to a mammalian subject. Without wishing to be bound by any particular theory, it is presently believed that therapy based on the combination NP-insulin/GLP-1 particle may be associated with reduced risk of pancreatitis, for example pancreatitis induced or exacerbated by the in situ pancreatic insulinotropic effect of exogenous or endogenous GLP-1.

In some cases in accordance with the present invention the two different species of peptide comprise first and second peptides which differ, and the molar ratio of said first peptide to said second peptide is in the range 1:100 to 100:1, preferably the ratio is in the range 1:10 to 10:1. In certain cases, the first peptide comprises insulin and the second peptide comprises GLP-1 and the molar ratio of insulin to GLP-1 is in the range 5:1 to 20:1.

In some cases in accordance with the present invention said carbohydrate moiety may comprises a monosaccharide and/or a disaccharide. The carbohydrate moiety may be as defined further herein, including a carbohydrate mimetic. The carbohydrate moiety may be covalently linked to the core via a linker selected from the group consisting of: sulphur-containing linkers, amino-containing linkers, phosphate-containing linkers and oxygen-containing linkers. In some cases the linker comprises an alkyl chain of at least two carbons.

In accordance with the present invention said at least one ligand comprising a carbohydrate moiety may in some cases be selected from the group consisting of: 2'-thioethyl-α-D-galactopyranoside, 2'-thioethyl-β-D-glucopyranoside, 2'-thioethyl-2-acetamido-2-deoxy-β-D-glucopyranoside, 5'-thiopentanyl-2-deoxy-2-imidazolacetamido-α,β-D-glucopyranoside and 2'-thioethyl-α-D-glucopyranoside, wherein said at least one ligand comprising a carbohydrate moiety is covalently linked to the core via its sulphur atom.

It is specifically contemplated herein that said plurality of ligands covalently linked to the core may comprise at least a first ligand and a second ligand, wherein the first and second ligands are different. For example the first and second ligands may be as follows:
(a) said first ligand comprises 2'-thioethyl-α-D-galactopyranoside and said second ligand comprises 1-amino-17-mercapto-3,6,9,12,15,-pentaoxa-heptadecanol;
(b) said first ligand comprises 2'-thioethyl-β-D-glucopyranoside or 2'-thioethyl-α-D-glucopyranoside and said second ligand comprises 5'-thiopentanyl-2-deoxy-2-imidazolacetamido-α,β-D-glucopyranoside;
(c) said first ligand comprises 2'-thioethyl-β-D-glucopyranoside or 2'-thioethyl-α-D-glucopyranoside and said second ligand comprises 1-amino-17-mercapto-3,6,9,12,15,-pentaoxa-heptadecanol; or
(d) said first ligand comprises 2'-thioethyl-2-acetamido-2-deoxy-β-D-glucopyranoside and said second ligand comprises 1-amino-17-mercapto-3,6,9,12,15,-pentaoxa-heptadecanol,
and wherein said first and second ligands are covalently linked to the core via their respective sulphur atoms.

In some cases the first ligand may comprise a carbohydrate moiety and said second ligand a non-carbohydrate ligand.

One or more of the ligands may be an amine group. In particular, the second ligand may comprise 1-amino-17-mercapto-3,6,9,12,15,-pentaoxa-heptadecanol covalently linked to the core via its sulphur atom.

As described further herein, where there different ligands are present on the nanoparticle they may be present at, e.g., certain defined ratios or ranges of ratios. For example, the first ligand and said second ligand may present on the nanoparticle in a ratio in the range of 1:40 to 40:1, 1:10 to 10:1 or even 1:2 to 2:1.

It has been found that the nanoparticles in accordance with the present invention may be provided with a variety of numbers of ligands forming the corona. For example, in some cases the corona comprises at least 5 ligands per core, e.g. between about 10 to about 1000 ligands per core or 44-106 ligands per core.

The number of peptide molecules bound per core is not particularly limited. For certain applications, it may be desirable to employ as few as 2, 3 or 4 peptides per core, while in other cases the nanoparticle of the invention may comprise at least 5, 10, 15, 20, 50 or more peptide molecules bound per core.

The nanoparticle "core" includes a metal and/or a semiconductor. Suitable cores are described in, e.g., WO 2002/032404, WO 2004/108165, WO 2005/116226, WO 2006/037979, WO 2007/015105, WO 2007/122388, WO 2005/091704 (the entire contents of each of which is expressly incorporated herein by reference) and such nanoparticle cores may find use in accordance with the present invention. Moreover, gold-coated nanoparticles including a magnetic core of iron oxide ferrites (having the formula $XFe_2O_4$, where X=Fe, Mn or Co) are described in European patent application publication No. EP2305310, the entire contents of which are expressly incorporated herein by reference, and may find use in accordance with the present invention.

In some cases in accordance with the present invention the nanoparticle core includes a metal selected from the group of: Au, Ag, Cu, Pt, Pd, Fe, Co, Gd, Zn or any combination thereof. The core may include a passive metal selected from the group of: Au, Ag, Pt, Pd and Cu, or any combination thereof. In certain embodiments a specific combination of metals may be employed, such as a combination of metals selected from the group of: Au/Fe, Au/Ag, Au/Cu, Au/Ag/Cu, Au/Pt, Au/Pd, Au/Ag/Cu/Pd, Au/Gd, Au/Fe/Cu, Au/Fe/Gd, Au/Fe/Cu/Gd.

In some cases in accordance with the present invention the nanoparticle core may be magnetic. The core may include an NMR active atom, such as a metal selected from the group of: $Mn^{2+}$, $Gd^{3+}$, $Eu^{2+}$, $Cu^{2+}$, $V^{2+}$, $Co^{2+}$, $Ni^{2+}$, $Fe^{2+}$, $Fe^{3+}$ and lanthanides$^{3+}$.

In some cases in accordance with the present invention the nanoparticle core may include a semiconductor, such as that selected from the group of: cadmium selenide, cadmium sulphide, cadmium tellurium and zinc sulphide.

In some cases in accordance with the present invention the nanoparticle core may include a metal oxide coated with a metal selected from the group of: Au, Ag, Cu, Pt, Pd and Zn, or any combination thereof. The metal oxide may advantageously be of the formula $XFe_2O_4$, where X is a metal selected from the group of: Fe, Mn and Co.

The nanoparticle core in accordance with the present invention may in some cases have a diameter in the range of about 0.5 nm to about 50 nm, such as about 1 nm to about 10 nm or about 1.5 nm to about 2 nm.

The presence of more than one species of peptide bound to the nanoparticle may exhibit preferred properties (in particular, pharmacodynamic and/or pharmacokinetic properties such as bioavailability or treatment profile) compared with binding of a single species of peptide. In particular, combinations of peptides may be carried on a nanoparticle such that the peptides perform mutually beneficial or complementary functions and/or act in concert, such as in a synergistic fashion. The presence of more than one species may be used for the purpose of treating one or more conditions and for one or more therapeutic indications.

In accordance with the present invention the nanoparticle of the invention may comprise a component having a divalent state, such as a metal or a compound having a divalent state, or an oxide or salt thereof. For example, metals or metal complexes having the ability to exist in a divalent state are particularly useful. Such a component may be in the divalent state as added or may be transformed into a divalent state after addition. Oxides and salts of the divalent component are also useful and may be added directly or formed in situ subsequent to addition. Among the useful salts of the divalent component include halide salts, such as chloride, iodide, bromide and fluoride. Such divalent components may include, for example, zinc, magnesium, copper, nickel, cobalt, cadmium, or calcium, and their oxides and salts thereof. The component is desirably present in an amount sufficient to produce a stabilizing effect and/or in an amount sufficient to enhance the binding of the peptide to the corona to a level greater than the level of binding of the peptide to the corona in the absence of the component having a divalent state. In some cases, the component having a divalent state is desirably present in an amount of about 0.5 to 2.0 equivalents to the core metal (e.g. gold), or optionally about 0.75 to 1.5 equivalents to the core metal (e.g. gold). In the context of the present invention, "equivalents" may be mole equivalents, for example 1.0 equivalent of zinc may be taken to mean the same number of zinc atoms or $Zn^{2+}$ cations as the number of gold atoms in the core of the nanoparticle.

The divalent component may in some cases be present in the corona of the nanoparticle. It is specifically contemplated herein that the divalent component may be included in the nanoparticle, including in the corona of the nanoparticle as a result of inclusion of the divalent component in the process of synthesis of the nanoparticle. Additionally or alternatively, the divalent component may be added after synthesis of the nanoparticle. In some cases in accordance with the present invention, the divalent component, such as zinc may be selected from: $Zn^{2+}$ and ZnO. For example, the zinc may be in the form of $ZnCl_2$.

In a further aspect the invention provides a plurality of nanoparticles of the invention. For example, a plurality may be 100, 1000, 100000, or more. The plurality may be in as associated form, a suspension or contained together in a single package, container or carrier. In certain cases, the plurality may take the form of one or more doses (e.g. a defined quantity of peptide or peptide activity units), such as in the form of a therapeutic dose or defined number of doses.

In a further aspect the present invention provides a pharmaceutical composition comprising a plurality of nanoparticles of the invention and one or more pharmaceutically acceptable carriers or excipients. In some cases, the pharmaceutical composition may be formulated for administration to a mammalian subject by intraveneous (i.v.), intramuscular (i.m.), intradermal (i.d.) or subcutaneous (s.c) route.

In a further aspect of the invention, the pharmaceutical composition comprising a plurality of nanoparticles of the present invention may be incorporated into a nasal delivery system. Such delivery systems may include a variety of stabilizing agents, surface active agents, penetrating agents, typically in a buffered aqueous solution. Desirably, the pH of the solution is chosen such that penetration is enhanced for absorption of the active while minimizing irritation of the nasal mucus membranes. This permits rapid absorption of the active, such as the insulin/GLP-1 nanoparticles, into the bloodstream. Among the surface active agents useful are non-ionic agents such as polyoxyethylene fatty acid ester, polyoxyethylene alcohol ethers, polyoxyethylene polyoxypropylene alcohol ethers, polyoxyethylene sorbitan fatty acid esters, polyoxyethylene alkylphenyl ether, polyoxyethylene hydrogenated castor oil and combinations thereof. Generally, surface active agents having a hydrophilic lipophilic balance value in the range of from about 9 to about 22 are preferred. Polyethylene glycol may also be used in place of the aforementioned surface active agents or in addition to such agents. Polyethylene glycols having molecular weights of about 200 to about 7500 and more preferably from about 600 to 7500 are more preferable. The insulin content of the nasal delivery system composition may be from about 0.1 to about 10% by weight. The upper limit is governed by the need for prevention of precipitation and/or stability concerns.

In another aspect of the invention, there is provided implantable compositions designed to controllably release the insulin/GLP-1 nanoparticles into the body. Such implantable compositions may comprise one or more bioerodable polymers, such as poly(glycolic acid) (PGA), poly(lactic acid) (PLA), polydioxanoes, polyoxalates, poly($\alpha$-esters), polyanhydrides, polyacetates, polycaprolactones and combinations thereof. These polymers may be combined with various other components as described herein to enhance the release profile and the erodability and hence, absorption of the actives. The implant may be in the form of a film, particulate, disc, or other suitable delivery form.

In another aspect of the invention, there is provided a buccal dosage form designed to adhere to the buccal membrane and controllably release the active. Such dosage forms may comprise one or more of the film compositions described herein which contain the inventive nanoparticles and in particular, the insulin/GLP-1 nanoparticles. In some aspects, the buccal dosage form may comprise an outer film and inner film, whereby the inventive nanoparticles may be present in one or more of the two films. Desirably, the nanoparticles containing the active are present in the inner film. More desirably, the outer film occludes the inner film and provides adhesivity to the cheek, while the inner film is surrounded by the outer film and provides release of the inventive nanoparticles. In such a manner, the nanoparticles containing the actives are thereby directed toward the mucus membrane of the buccal cavity.

Nanoparticles of the present invention may also be delivered sublingually, for example using the inventive film compositions. Absorption may be through more than one mucosal membrane, for example multiple dosages may be used or a single dose may affect more than one membrane. Moreover, dosages may be reconstituted in liquid media and used in injectable compositions.

In a further aspect, the present invention provides a method of modifying at least one pharmcodynamic and/or pharmacokinetic property of a combination of at least two different peptides, the method comprising:
contacting the combination of at least two peptides with a nanoparticle under conditions which allow the at least two peptides to bind to the nanoparticle. The nanoparticle may be a nanoparticle as described in accordance with the first aspect of the invention.

In particular, the nanoparticle may comprise:
(i) a core comprising a metal and/or a semiconductor;
(ii) a corona comprising a plurality of ligands covalently linked to the core, wherein at least one of said ligands comprises a carbohydrate moiety.

The method may be a method of modifying at least one pharmcodynamic and/or pharmacokinetic property of a combination of at least two different peptides independently selected from the group consisting of: insulin, GLP-1, IGF1, IGF2, relaxin, INSL5, INSL6, INSL7, pancreatic polypeptide(PP), peptide tyrosine tyrosine(PTT), neuropeptide Y, oxytocin, vasopressin, GnRH, TRH, CRH, GHRH/somatostatin, FSH, LH, TSH, CGA, prolactin, ClIP, ACTH, MSH, enorphins, lipotropin, GH, calcitonin, PTH, inhibin, relaxin, hCG, HPL, glucagons, somatostatin, melatonin, thymosin, thmulin, gastrin, ghrelin, thymopoietin, CCK, GIP secretin, motin VIP, enteroglucagon, IGF-1, IGF-2, leptin, adiponectin, resistin Osteocalcin, renin, EPO, calicitrol, ANP, BNP, chemokines, cytokines, adipokines, and suitable biologically active analogues of any one of the peptides listed herein. In some cases at least one of said peptides comprises monomeric and/or dimeric human insulin or a suitable analogue of human insulin. In some cases at least one of said peptides comprises GLP-1 or a suitable analogue thereof. In some cases the at least two different species of peptide comprise: (i) insulin or an analogue thereof; and (ii) GLP-1 or a suitable analogue thereof as well as exenatide and its suitable analogues thereof.

The method in accordance with this aspect of the invention may be for enhancing the biodistribution of the combination of peptides upon administration of said combination of peptides to a mammalian subject. For example, the biodistribution of the two or more different species of peptide co-bound to the nanoparticle may be enhanced as compared with a mixture of the same peptides which are not co-bound to a nanoparticle.

Accordingly, the present invention provides a method for: reducing the glucose excursion of a subject in response to a glucose challenge;

enhancing biodistribution and/or bioavailability in a subject; enhancing the glucagon response of a subject; and/or reducing the pancreatic insulinotropic effect in a subject when insulin and GLP-1 are administered to a mammalian subject, the method comprising:

contacting both said insulin and said GLP-1 with a nanoparticle under conditions which allow the insulin and the GLP-1 to bind to the nanoparticle, thereby forming a nanoparticle having both insulin and GLP-1 bound thereto.

In a further aspect the present invention provides a method of lowering blood glucose in a mammalian subject (for example a human) in need thereof, comprising administering a therapeutically effective amount of a nanoparticle of the invention, for example a nanoparticle having insulin and GLP-1 bound to the corona.

In a further aspect the present invention provides a method of treating diabetes in a mammalian subject in need thereof, comprising administering a therapeutically effective amount of a nanoparticle of the invention, for example a nanoparticle having insulin and GLP-1 bound to the corona. The nanoparticle of the invention or a pharmaceutical composition comprising the nanoparticle may be administered to a subject by any suitable route of administration. In particular cases, the nanoparticle of the invention or pharmaceutical composition comprising said nanoparticle may be administered intraveneously (i.v.), intramuscularly (i.m.), intradermally (i.d.) or subcutaneously (s.c.).

In a further aspect the present invention provides a nanoparticle of the invention for use in a method of medical treatment. The nanoparticle may be formulated for pharmaceutical use, for example by combining one or, typically, a plurality of nanoparticles of the invention with one or more pharmaceutically acceptable excipients or carriers. The nanoparticle of the invention or pharmaceutical composition comprising said nanoparticle may be formulated for administration by any suitable route for delivery to a subject. In particular, the nanoparticle of the invention or pharmaceutical composition comprising said nanoparticle may be formulated for administration intraveneously (i.v.), intramuscularly (i.m.), intradermally (i.d.) or subcutaneously (s.c.).

In a further aspect the present invention provides a nanoparticle of the invention (for example a nanoparticle having insulin and GLP-1 bound to the corona) for use in a method of lowering blood glucose in a mammalian subject in need thereof and/or treating diabetes in a mammalian subject in need thereof.

In a further aspect the present invention provides use of a nanoparticle of the invention (for example a nanoparticle having insulin and GLP-1 bound to the corona) in the preparation of a medicament for use in a method of lowering blood glucose in a mammalian subject in need thereof and/or treating diabetes.

The subject may be a human or any of a variety of domestic, farm, experimental or companion animals, such as a dog, cat, cow, sheep, pig, horse, non-human primate, mouse, rat or rabbit. In some cases, the subject is has been diagnosed as having, or being at risk of developing, diabetes mellitus (including type 1 diabetes, type-2 diabetes, insulin resistance or gestational diabetes). Additionally or alternatively, the subject may have, or be at risk of developing, pancreatitis (including insulin- or GLP-1-induced pancreatitis).

In a further aspect the present invention provides an article of manufacture comprising:
 at least one nanoparticle of the invention;
 a container for housing the at least one nanoparticle; and
 an insert and/or a label.

As described herein with reference to certain embodiments of the present invention, the peptides may be bound such that at least a fraction or portion of the bound peptides is released from the nanoparticle upon contacting the nanoparticle with a physiological solution. As described herein the peptides may be bound to the nanoparticle in a manner such that the peptides are stabilised (e.g. thermostabilised) while bound, but are releasable and available in a form that is biologically active (for example, releasable such that each of the bound peptides is detectable by ELISA and/or capable of exerting at least one biological action in an in vitro or in vivo system that is characteristic of the free peptide). In particular, when the peptides includes (human) insulin, the binding to the nanoparticle may be such that a suspension of the nanoparticles gives a positive result in an ELISA for (human) insulin and/or exerts an effect on blood glucose levels in a mammalian subject following administration thereto.

A variety of release kinetics are contemplated for dissociation of bound peptide molecules from the nanoparticle, including bi- or multi-phase release (such as an initial fast release followed by a slower subsequent release phase). For example, the release may include dissociation of one or more of the different species of bound peptide molecules from the nanoparticle rapidly within seconds or minutes followed by further sustained release over a period of at least 2, 4, 6, 8 or more hours. Such release kinetics may be advantageous in certain circumstances, e.g. where sustained action is desired, in comparison with, e.g., an injection of the free peptides.

Mixing a Film Forming Matrix

As discussed above, the active components of the present invention may be provided in the form of a film dosage form. In such embodiments, a flowable film-forming matrix is prepared to be uniform in content in accordance with the teachings of the present invention. Uniformity should be maintained as the flowable mass is formed into a film and dried. During the drying process of the present invention, several factors produce uniformity within the film while maintaining the active component at a safe temperature, i.e., below a temperature at which degradation occurs. First, the films of the present invention have an extremely short heat history, usually only on the order of minutes, so that total temperature exposure is minimized to the extent possible. The films are controllably dried to prevent aggregation and migration of components, as well as preventing heat build up within. The films may be dried from the bottom. In any drying method, however, it is desirable to rapidly form a visco-elastic film within the first fifteen minutes of drying, and desirably within the first ten minutes of drying, and even more preferably within the first four minutes of drying. Due to the short heat exposure and evaporative cooling, the film components such as drug or volatile actives remain unaffected by high temperatures, and small-scale particles of active agent are maintained in a non-aggregated fashion. In contrast, skinning on the top surface traps liquid carrier molecules of increased energy within the film, thereby causing the temperature within the film to rise and exposing active components to high, potentially deleterious temperatures. Preferably, the interior of the film does not reach a level at which degradation of the active contained therein will occur or, if occurring, the degradation does not affect the potency of the film. Once the rapid formation of a visco-elastic film is achieved, to "lock-in" the uniformity of active content per unit dose, the film may be further dried, such as by exposure to heat, radiation, or other drying source. The step of further drying the thus-formed viscoelastic film may reduce the water or solvent content in the film to less than 10% by weight, less than 8% by weight, less than 6% by weight, less than 4% by weight, or less than 2% by weight.

Second, thermal mixing occurs within the film due to controlled drying and absence of surface skinning. Thermal mixing occurs via convection currents in the film. As heat is applied to the bottom of the film, the liquid near the bottom increases in temperature, expands, and becomes less dense. As such, this hotter liquid rises and cooler liquid takes its place. While rising, the hotter liquid mixes with the cooler liquid and shares thermal energy with it, i.e., transfers heat. As the cycle repeats, thermal energy is spread throughout the film.

Robust thermal mixing achieved by the controlled drying process of the present invention produces uniform heat diffusion throughout the film. In the absence of such thermal mixing, "hot spots" may develop. Pockets of heat in the film result in the formation of particle aggregates or danger areas within the film and subsequent non-uniformity. The formation of such aggregates or agglomerations is undesirable because it leads to non-uniform films in which the active may be randomly distributed. Such uneven distribution may lead to large differences in the amount of active per film, which is problematic from a safety and efficacy perspective.

Furthermore, thermal mixing helps to maintain a lower overall temperature inside the film. Although the film surfaces may be exposed to a temperature above that at which the active component degrades, the film interior may not reach this temperature. Due to this temperature differential, the active does not degrade to a level that reduces the amount of viable active to an undesirable amount. That is, while some degradation of the active may occur during drying, the remaining active is within about 10% of a target level of the active, as will be explained below.

For instance, the films of the present invention may be dried for 15 minutes or less, desirably 10 minutes or less to achieve a desired solvent content. Drying the films at 80° C. for 10 minutes produces a temperature differential of about 5° C. This means that after 10 minutes of drying, the temperature of the inside of the film is 5° C. less than the outside exposure temperature. In many cases, however, drying times of less than 10 minutes are sufficient, such as 4 to 6 minutes. Drying for 4 minutes may be accompanied by a temperature differential of about 30° C., and drying for 6 minutes may be accompanied by a differential of about 25° C. Due to such large temperature differentials, the films may be dried at efficient, high external temperatures without causing heat sensitive actives to degrade. Further drying may be used to reduce the solvent content to an even lower level.

After mechanical mixing, the film may be placed on a conveyor for continued thermal mixing during the drying process. At the outset of the drying process, the film preferably is heated from the bottom as it is travels via conveyor. Heat may be supplied to the film by a heating mechanism, such as, but not limited to, a dryer. As the film is heated, the liquid carrier, or volatile, begins to evaporate. Thermal mixing also initiates as hotter liquid rises and cooler liquid takes its place. Because no skin forms on the top surface of the film, the volatile liquid continues to evaporate and thermal mixing continues to distribute thermal energy throughout the film. Once a sufficient amount of the volatile liquid has evaporated, thermal mixing has produced uniform heat diffusion throughout the film. The components desirably are locked into a uniform distribution throughout the film. It may be desired to form a visco-elastic solid rapidly, for example within the first 15 minutes or less, desirably within the first 10 minutes or less, more desirably within the first 6 minutes or less, and most desirably within the first 0.5 minutes to 4 minutes. Although minor amounts of liquid carrier, i.e., water, water/alcohol carrier, or other suitable carrier, may remain subsequent to formation of the visco-elastic film, the film may be dried further without affecting the desired uniformity of active content and heterogeneity of the film, if desired. Further drying forms the final film, by desirably removing solvent from the visco-elastic solid such that less than 10% of solvent remains, and more desirably less than 8% of solvent remains, and most desirably less than 6% of the solvent remains in the final film.

The internal temperature of the film matrix during drying is desirably less than about 100° C., desirably less than about 70° C., less than about 60° C., less than about 50° C., less than about 40° C., or less than about 30° C. The external temperature at which the film is dried may be higher than the internal temperature, and may be, for example, 40° C. or greater, 50° C. or greater, 60° or greater, 70° C. or greater, may be 80° C. or greater, or may be 100° C. or greater. The film may be exposed to a high temperature, such as about 100° C. or greater, for a short period of time, such as less than about a few minutes. For example, the air temperatures used to dry the film may be about 130° C. or higher, the upper limit being dictated by the specific formulation (e.g., the types and amount of solvent, polymers, fillers, etc.) and active used. The air temperature is also dictated by the length of the drying required to rapidly form the visco-elastic film to lock in the uniformity of content, as discussed herein.

Furthermore, particles or particulates may be added to the film-forming composition or material after the composition or material is cast into a film. For example, particles may be added to the film prior to the drying of the film. Particles may be controllably metered to the film and disposed onto the film through a suitable technique, such as through the use of a doctor blade, which is a device which marginally or softly touches the surface of the film and controllably disposes the particles onto the film surface. Other suitable, but non-limiting, techniques include the use of an additional roller to place the particles on the film surface, spraying the particles onto the film surface, and the like. The particles may be placed on either or both of the opposed film surfaces, i.e., the top and/or bottom film surfaces. Desirably, the particles are securably disposed onto the film, such as being embedded into the film. Moreover, such particles are desirably not fully encased or fully embedded into the film, but remain exposed to the surface of the film, such as in the case where the particles are partially embedded or partially encased.

Monitoring and control of the thickness of the film also contributes to the production of a uniform film by providing a film of uniform thickness. The thickness of the film may be monitored with gauges such as Beta Gauges. A gauge may be coupled to another gauge at the end of the drying apparatus, i.e. drying oven or tunnel, to communicate through feedback loops to control and adjust the opening in the coating apparatus, resulting in control of uniform film thickness. Alternatively, the thickness of the film can also be controlled by manual measurement during the production process to achieve the desired thickness of the film.

The film products are generally formed by combining a properly selected polymer and polar solvent, as well as any agent or filler as desired. Desirably, the solvent content of the combination is at least about 30% by weight of the total combination. The material formed by this combination is formed into a film, desirably by roll coating, and then dried, desirably by a rapid and controlled drying process to maintain the uniformity of the film, more specifically, a non-self-aggregating uniform heterogeneity. The resulting film will desirably contain less than about 10% by weight solvent, more desirably less than about 8% by weight solvent, even more desirably less than about 6% by weight solvent and most desirably less than about 2%. The solvent may be water, a polar organic solvent including, but not limited to, ethanol, isopropanol, acetone, methylene chloride, or any combination thereof.

Consideration of the above discussed parameters, such as, but not limited to, rheology properties, viscosity, mixing method, casting method and drying method, also impact material selection for the different components of the present invention. Furthermore, such consideration with proper material selection provides the compositions of the present invention, including a pharmaceutical and/or cosmetic dosage form or film product having no more than a 10% variance of a pharmaceutical and/or cosmetic active per unit volume, or no more of than a ten percent (10%) variance by weight of an active-carrying component (e.g. nanoparticles) per unit volume of the film product. The compositional uniform distribution may be measured by preparing substantially equally-sized individual unit doses from the film, where the substantially equally-sized individual unit doses do not vary from each other by more than 10% of active component.

In other words, the uniformity of the present invention may be determined by the presence of no more than a 10% by weight of pharmaceutical, biological, bioeffecting, active-containing component, and/or cosmetic variance throughout the matrix, or in other words, substantially equally sized dosage units cut from the same film do not vary from each other by more than about 10% of the target level of active content. Desirably, the variance is less than 5% by weight, less than 2% by weight, less than 1% by weight, or less than 0.5% by weight.

In some embodiments, compositional uniformity may be measured with respect to a target or desired level of active. The film is prepared so as to provide each unit dose with a target level of active therein. Compositional uniformity is achieved when each individual unit dose varies by no more than 10% of the target level of active (by weight). More desirably, each unit dose varies by no more than 8% of the target level of active, no more than 6% of the target level of active, or no more than 4% of the target level of active. In addition, if any degradation of the active occurs during the process, the amount of remaining active that has not degraded should be within 10% of the target level, or within about 8% of the target level, or within about 6% of the target level, or within about 4% of the target level.

Film-Forming Polymers

The film units of the present invention include at least one water soluble polymer. The films may also include water swellable or water insoluble polymers, if desired.

In some embodiments, the self-supporting film includes a saccharide-based polymer, which is water soluble. For example, the saccharide-based polymer may be cellulose or a cellulose derivative. Specific examples of useful saccharide-based, water soluble polymers include, but are not limited to, polydextrose, pullulan, hydroxypropylmethyl cellulose (HPMC), hydroxyethyl cellulose (HPC), hydroxypropyl cellulose, carboxymethyl cellulose, sodium alginate, xanthan gum, tragancanth gum, guar gum, acacia gum, arabic gum, starch, gelatin, and combinations thereof.

In some preferred embodiments, the saccharide-based polymer may be at least one cellulosic polymer, polydextrose, or combinations thereof. The film may also include non-saccharide-based, water soluble or water insoluble polymers. Examples of non-saccharide based, water soluble polymers include polyethylene oxide, polyvinylpyrrolidone, polyvinyl alcohol, polyethylene glycol, polyacrylic acid, methyl-methacrylate copolymer, carboxyvinyl copolymers, and combinations thereof. Specific examples of useful water insoluble polymers include, but are not limited to, ethyl cellulose, hydroxypropyl ethyl cellulose, cellulose acetate phthalate, hydroxypropyl methyl cellulose phthalate and combinations thereof.

In some further preferred embodiments, the polymer is a combination of hydroxypropylmethyl cellulose and polyethylene oxide. In some other preferred embodiments, the polymer is a combination of polydextrose and polyethylene oxide. In still further preferred embodiments, the polymer is a combination of polydextrose, hydroxy propylmethyl cellulose and polyethylene oxide.

As used herein, the phrase "water soluble polymer" and variants thereof refer to a polymer that is at least partially soluble in water, and desirably fully or predominantly soluble in water, or absorbs water. In some embodiments, the film unit of the present invention is at least partially dissolvable when exposed to a wetting agent. In some other embodiments, the inventive film unit is substantially dissolvable when exposed to a wetting agent.

Polymers that absorb water are often referred to as being water swellable polymers. The materials useful with the present invention may be water soluble or water swellable at room temperature and other temperatures, such as temperatures exceeding room temperature. Moreover, the materials may be water soluble or water swellable at pressures less than atmospheric pressure. Desirably, the water soluble polymers are water soluble or water swellable having at least 20 percent by weight water uptake. Water swellable polymers having a 25 or greater percent by weight water uptake are also useful. Films or dosage forms of the present invention formed from such water soluble polymers are desirably sufficiently water soluble to be dissolvable upon contact with bodily fluids.

Other polymers useful for incorporation into the films of the present invention include biodegradable polymers, copolymers, block polymers and combinations thereof. Among the known useful polymers or polymer classes which meet the above criteria are: poly(glycolic acid) (PGA), poly (lactic acid) (PLA), polydioxanoes, polyoxalates, poly($\alpha$-esters), polyanhydrides, polyacetates, polycaprolactones, poly(orthoesters), polyamino acids, polyaminocarbonates, polyurethanes, polycarbonates, polyamides, poly(alkyl cyanoacrylates), and mixtures and copolymers thereof. Additional useful polymers include, stereopolymers of L- and D-lactic acid, copolymers of bis(p-carboxyphenoxy)propane acid and sebacic acid, sebacic acid copolymers, copolymers of caprolactone, poly(lactic acid)/poly(glycolic acid)/poly-ethyleneglycol copolymers, copolymers of polyurethane and (poly(lactic acid), copolymers of polyurethane and poly(lactic acid), copolymers of $\alpha$-amino acids, copolymers of $\alpha$-amino acids and caproic acid, copolymers of $\alpha$-benzyl glutamate and polyethylene glycol, copolymers of succinate and poly(glycols), polyphosphazene, polyhydroxy-alkanoates and mixtures thereof. Binary and ternary systems are contemplated.

Other specific polymers useful include those marketed under the Medisorb and Biodel trademarks. The Medisorb materials are marketed by the Dupont Company of Wilmington, Del. and are generically identified as a "lactide/glycolide co-polymer" containing "propanoic acid, 2-hydroxy-polymer with hydroxy-polymer with hydroxyacetic acid." Four such polymers include lactide/glycolide 100 L, believed to be 100% lactide having a melting point within the range of 338°-347° F. (170°-175° C.); lactide/glycolide 100 L, believed to be 100% glycolide having a melting point within the range of 437°-455° F. (225°-235° C.); lactide/glycolide 85/15, believed to be 85% lactide and 15% glycolide with a melting point within the range of 338°-347° F. (170°-175° C.); and lactide/glycolide 50/50, believed to be a copolymer of 50% lactide and 50% glycolide with a melting point within the range of 338°-347° F. (170°-175° C.).

The Biodel materials represent a family of various polyanhydrides which differ chemically.

Although a variety of different polymers may be used, it is desired to select polymers to provide a desired viscosity of the mixture prior to drying. For example, if the agent or other components are not soluble in the selected solvent, a polymer that will provide a greater viscosity is desired to assist in maintaining uniformity. On the other hand, if the components are soluble in the solvent, a polymer that provides a lower viscosity may be preferred.

The polymer plays an important role in affecting the viscosity of the film. Viscosity is one property of a liquid that controls the stability of the topical agent in a solution, an emulsion, a colloid or a suspension. Generally the viscosity of the matrix will vary from about 400 cps to about 100,000 cps, preferably from about 800 cps to about 60,000 cps, and most preferably from about 1,000 cps to about 40,000 cps. Desirably, the viscosity of the film-forming matrix will rapidly increase upon initiation of the drying process.

The viscosity may be adjusted based on the selected topical agent component, depending on the other components within the matrix. For example, if the component is not soluble within the selected solvent, a proper viscosity may be selected to prevent the component from settling which would adversely affect the uniformity of the resulting film. The viscosity may be adjusted in different ways. To increase viscosity of the film matrix, the polymer may be chosen of a higher molecular weight or crosslinkers may be added, such as salts of calcium, sodium and potassium. The viscosity may also be adjusted by adjusting the temperature or by adding a viscosity increasing component. Components that will increase the viscosity or stabilize the emulsion/suspension include higher molecular weight polymers and polysaccharides and gums, which include without limitation, alginate, carrageenan, hydroxypropyl methyl cellulose, locust bean gum, guar gum, xanthan gum, dextran, gum arabic, gellan gum and combinations thereof.

It has also been observed that certain polymers which when used alone would ordinarily require a plasticizer to achieve a flexible film, can be combined without a plasticizer and yet achieve flexible films. For example, HPMC and HPC when used in combination provide a flexible, strong film with the appropriate plasticity and elasticity for manufacturing and storage. No additional plasticizer or polyalcohol is needed for flexibility.

Additionally, polyethylene oxide (PEO), when used alone or in combination with a hydrophilic cellulosic polymer and/or polydextrose, achieves flexible, strong films. Additional plasticizers or polyalcohols are not needed for flexibility. Non-limiting examples of suitable cellulosic polymers for combination with PEO include HPC and HPMC. PEO and HPC have essentially no gelation temperature, while HPMC has a gelation temperature of 58-64° C. (Methocel EF available from Dow Chemical Co.). Moreover, these films are sufficiently flexible even when substantially free of organic solvents, which may be removed without compromising film properties. As such, if there is no solvent present, then there is no plasticizer in the films. PEO based films also exhibit good resistance to tearing, little or no curling, and fast dissolution rates when the polymer component contains appropriate levels of PEO.

To achieve the desired film properties, the level and/or molecular weight of PEO in the polymer component may be varied. Modifying the PEO content affects properties such as tear resistance, dissolution rate, and adhesion tendencies. Thus, one method for controlling film properties is to modify the PEO content. For instance, in some embodiments rapid dissolving films are desirable. By modifying the content of the polymer component, the desired dissolution characteristics can be achieved.

In accordance with the present invention, PEO desirably ranges from about 20% to 100% by weight in the polymer component. In some embodiments, the amount of PEO desirably ranges from about 1 mg to about 200 mg. The hydrophilic cellulosic polymer and/or polydextrose ranges from about 0% to about 80% by weight, or in a ratio of up to about 4:1 with the PEO, and desirably in a ratio of about 1:1.

In some embodiments, it may be desirable to vary the PEO levels to promote certain film properties. To obtain films with high tear resistance and fast dissolution rates, levels of about 50% or greater of PEO in the polymer component are desirable. To achieve adhesion prevention, i.e., preventing the film from adhering to the roof of the mouth, PEO levels of about 20% to 75% are desirable. In some embodiments, however, adhesion to the roof of the mouth may be desired, such as for administration to animals or children. In such cases, higher levels of PEO may be employed. More specifically, structural integrity and dissolution of the film can be controlled such that the film can adhere to mucosa and be readily removed, or adhere more firmly and be difficult to remove, depending on the intended use.

The molecular weight of the PEO may also be varied. High molecular weight PEO, such as about 4 million, may be desired to increase mucoadhesivity of the film. More desirably, the molecular weight may range from about 100,000 to 900,000, more desirably from about 100,000 to 600,000, and most desirably from about 100,000 to 300,000. In some embodiments, it may be desirable to combine high molecular weight (600,000 to 900,000) with low molecular weight (100,000 to 300,000) PEOs in the polymer component.

For instance, certain film properties, such as fast dissolution rates and high tear resistance, may be attained by combining small amounts of high molecular weight PEOs with larger amounts of lower molecular weight PEOs. Desirably, such compositions contain about 60% or greater levels of the lower molecular weight PEO in the PEO-blend polymer component.

To balance the properties of adhesion prevention, fast dissolution rate, and good tear resistance, desirable film compositions may include about 50% to 75%, by weight of the total composition, low molecular weight PEO, optionally combined with a small amount of a higher molecular weight PEO, with the remainder of the polymer component containing a hydrophilic cellulosic polymer (HPC or HPMC) and/or polydextrose.

In some embodiments the film may include polyvinyl alcohol (PVA), alone or in combination with at least one additional polymer Examples of an additional polymer include a cellulosic polymer, starch, polyvinyl pyrrolidone (PVP), polyethylene oxide (PEO), an alginate, a pectin, or combinations thereof. PVA can be used in the films to improve film strength and/or to vary and slow dissolution times. The films are especially useful for the delivery of cosmetics, nutraceuticals and pharmaceuticals. In a preferred embodiment, the film includes PVA without any added plasticizers. For example, the film can include both PVA, which provides strength to the film and PEO, which provides flexibility to the film and nay obviate the need for a plasticizer.

PVA can be used in varying amounts depending upon the product application and characteristics desired. For example, in general, a larger amount of PVA will increase film strength and increase dissolution time. For films that require high active dosing, PVA can be used effectively at minimum amount of 0.5, preferably 1%, more preferably 5%, by weight of the film, to improve film strength. The PVA an be effectively used at a maximum amount, for example, 80%, preferably 50%, more preferably 25% by weight of the film. For slowing dissolution time, PVA can be used at levels as high as 80%. A film containing an active can be coated on one or both surfaces with a PVA containing layer to modify the dissolution of the film and the release of an active from the film.

High loading of actives can decrease the strength and flexibility of the film. Including PVA in the film either alone or in combination with at least one other polymer can increase the tensile strength of the film. Also, drug particles or taste-masked or coated or modified release drug particles may have a larger particle size, which can make loading of these particles into the film difficult. PVA can increase the viscosity of the film solution to allow improved drug loading.

Controlled Release Films

The term "controlled release" is intended to mean the release of the components at a pre-selected or desired rate. For example, in embodiments where the film includes nanoparticles within the body of the film, it may be desirable to control its release from the film. This rate will vary depending upon the application. Desirable rates include fast or immediate release profiles as well as delayed, sustained or sequential release. Combinations of release patterns, such as initial spiked release followed by lower levels of sustained release of active are contemplated. Pulsed releases of the agent are also contemplated.

Dissolvable films generally fall into three main classes: fast dissolving, moderate dissolving and slow dissolving. Films of the present invention are dissolvable in the presence of liquid, such as in the oral cavity of the user or when mixed with a liquid, such as water. Fast dissolving films generally dissolve in about 1 second to about 30 seconds. Moderate dissolving films generally dissolve in about 1 to about 30 minutes, and slow dissolving films generally dissolve in more than 30 minutes, e.g., up to about 60 minutes or more. Fast dissolving films may consist of low molecular weight hydrophilic polymers (i.e., polymers having a molecular weight between about 1,000 to 200,000). In contrast, slow dissolving films generally have high molecular weight polymers (i.e., having a molecular weight in the millions).

Moderate dissolving films tend to fall in between the fast and slow dissolving films. Moderate dissolving films dissolve rather quickly, but also have a good level of mucoadhesion. Moderate films are also flexible, quickly wettable, and are typically non-irritating to the user. For oral-dissolving films, moderate dissolving films are preferred, since such films provide a quick enough dissolution rate (between about 1 minute and about 5 minutes), while providing an acceptable mucoadhesion level such that the film is not easily removable once it is placed in the oral cavity of the user.

The polymers that are chosen for the films of the present invention may also be chosen to allow for controlled disintegration of the components. This may be achieved by providing a substantially water insoluble film that incorporates an nanoparticle that will be released from the film over time. This may be accomplished by incorporating a variety of different soluble or insoluble polymers and may also include biodegradable polymers in combination. Alternatively, coated controlled release agent particles may be incorporated into a readily soluble film matrix to achieve the controlled release property of the nanoparticles.

The convenience of administering a single dose of a medication which releases components in a controlled fashion over an extended period of time, as opposed to the administration of a number of single doses at regular intervals has long been recognized in the pharmaceutical arts. The advantage to the patient and clinician in having consistent and uniform levels of medication delivered to the body over an extended period of time are likewise recognized.

In some embodiments, the erosion or disintegration of the film (e.g., the residence time) can be controlled by a combination of factors. One factor may be the thickness of the film, whereby due to its physical dimensions, disintegration of a thicker film in the body, such as in the oral cavity, as with a buccal dosage form, is designed to be slower than a film that has thinner dimensions. Additionally, the selection of amounts and types of polymers and/or molecular weights of polymers, as well as inclusion of additives or disintegration aides, may be employed to vary residence time. Selection of polymers and inclusion of additives may be used alone or in combination with the use of different thicknesses to achieve the desired residence time. These factors have the ability to effect the release of active in a desired time.

Optional Components

A variety of other components and fillers may also be added to the films of the present invention. These may include, without limitation, surfactants; plasticizers which assist in compatibilizing the components within the mixture; polyalcohols; anti-foaming agents, such as silicone-containing compounds, which promote a smoother film surface by releasing oxygen from the film; and thermo-setting gels such as pectin, carageenan, and gelatin, which help in maintaining the dispersion of components.

The variety of additives that can be incorporated into the inventive compositions may provide a variety of different functions. Examples of classes of additives include excipients, lubricants, buffering agents, stabilizers, blowing agents, pigments, coloring agents, fillers, bulking agents, fragrances, release modifiers, adjuvants, plasticizers, flow accelerators, mold release agents, polyols, granulating agents, diluents, binders, buffers, absorbents, glidants, adhesives, anti-adherents, acidulants, softeners, resins, demulcents, solvents, surfactants, emulsifiers, elastomers and mixtures thereof. These additives may be added with the active ingredient(s).

Useful additives include, for example, gelatin, vegetable proteins such as sunflower protein, soybean proteins, cotton seed proteins, peanut proteins, grape seed proteins, whey proteins, whey protein isolates, blood proteins, egg proteins, acrylated proteins, water soluble polysaccharides such as alginates, carrageenans, guar gum, agar-agar, xanthan gum, gellan gum, gum arabic and related gums (gum ghatti, gum karaya, gum tragancanth), pectin, water soluble derivatives of cellulose: alkylcelluloses hydroxyalkylcelluloses and hydroxyalkylalkylcelluloses, such as methylcelulose, hydroxymethylcellulose, hydroxyethylcellulose, hydroxypropylcellulose, hydroxyethylmethylcellulose, hydroxypropylmethylcellulose, hydroxybutylmethylcellulose, cellulose esters and hydroxyalkylcellulose esters such as cellulose acetate phthalate (CAP), hydroxypropylmethylcellulose (HPMC); carboxyalkylcelluloses, carboxyalkylalkylcelluloses, carboxyalkylcellulose esters such as carboxymethylcellulose and their alkali metal salts; water soluble synthetic polymers such as polyacrylic acids and polyacrylic acid esters, polymethacrylic acids and polymethacrylic acid esters, polyvinylacetates, polyvinylalcohols, polyvinylacetatephthalates (PVAP), polyvinylpyrrolidone (PVP), PVY/vinyl acetate copolymer, and polycrotonic acids; also suitable are phthalated gelatin, gelatin succinate, crosslinked gelatin, shellac, water soluble chemical derivatives of starch, cationically modified acrylates and methacrylates possessing, for example, a tertiary or quaternary amino group, such as the diethylaminoethyl group, which may be quaternized if desired; and other similar polymers.

Such extenders may optionally be added in any desired amount desirably within the range of up to about 80%, desirably about 3% to 50% and more desirably within the range of 3% to 20% based on the weight of all components.

Further additives may be glidants and opacifiers, such as the oxides of magnesium aluminum, silicon, titanium, etc. desirably in a concentration range of about 0.02% to about 3% by weight and desirably about 0.02% to about 1% based on the weight of all components.

Further examples of additives are plasticizers which include polyalkylene oxides, such as polyethylene glycols, polypropylene glycols, polyethylene-propylene glycols, organic plasticizers with low molecular weights, such as glycerol, glycerol monoacetate, diacetate or triacetate, triacetin, polysorbate, cetyl alcohol, propylene glycol, sorbitol, sodium diethylsulfosuccinate, triethyl citrate, tributyl citrate, and the like, added in concentrations ranging from about 0.5% to about 30%, and desirably ranging from about 0.5% to about 20% based on the weight of the polymer.

There may further be added compounds to improve the texture of the starch material such as animal or vegetable fats, desirably in their hydrogenated form, especially those which are solid at room temperature. These fats desirably have a melting point of 50° C. or higher. Preferred are tri-glycerides with $C_{12}$-, $C_{14}$-, $C_{16}$-, $C_{18}$-, $C_{20}$- and $C_{22}$-fatty acids. These fats can be added alone without adding extenders or plasticizers and can be advantageously added alone or together with mono- and/or di-glycerides or phosphatides, especially lecithin. The mono- and di-glycerides are desirably derived from the types of fats described above, i.e. with $C_{12}$-, $C_{14}$-, $C_{16}$-, $C_{18}$-, $C_{20}$- and $C_{22}$-fatty acids.

The total amounts used of the fats, mono-, di-glycerides and/or lecithins are up to about 5% and preferably within the range of about 0.5% to about 2% by weight of the total composition It is further useful to add silicon dioxide, calcium silicate, or titanium dioxide in a concentration of about 0.02% to about 1% by weight of the total composition. These compounds act as opacifiers and flow agents.

These additives are to be used in amounts sufficient to achieve their intended purpose. Generally, the combination of certain of these additives will alter the overall release profile of the active ingredient and can be used to modify, i.e. impede or accelerate the release.

Lecithin is one surface active agent for use in the present invention. Lecithin can be included in the feedstock in an amount of from about 0.25% to about 2.00% by weight. Other surface active agents, i.e. surfactants, include, but are not limited to, cetyl alcohol, sodium lauryl sulfate, the Spans™ and Tweens™ which are commercially available from ICI Americas, Inc. Ethoxylated oils, including ethoxylated castor oils, such as Cremophor® EL which is commercially available from BASF, are also useful. Carbowax™ is yet another modifier which is very useful in the present invention. Tweens™ or combinations of surface active agents may be used to achieve the desired hydrophilic-lipophilic balance ("HLB"). The present invention, however, does not require the use of a surfactant and films or film-forming compositions of the present invention may be essentially free of a surfactant while still providing the desirable uniformity features of the present invention.

As additional modifiers which enhance the procedure and product of the present invention are identified, Applicants intend to include all such additional modifiers within the scope of the invention claimed herein.

Other ingredients include binders which contribute to the ease of formation and general quality of the films. Non-limiting examples of binders include starches, pregelatinize starches, gelatin, polyvinylpyrrolidone, methylcellulose, sodium carboxymethylcellulose, ethylcellulose, polyacrylamides, polyvinyloxoazolidone, and polyvinylalcohols.

Films of the present invention, particularly films useful for oral ingestion by a user, may further include one or more taste-enhancing agents, such as flavors and/or sweeteners. Suitable flavors and sweeteners include those set forth in U.S. Pat. No. 7,425,292, the entire contents of which are incorporated by reference herein.

Further potential additives include solubility enhancing agents, such as substances that form inclusion compounds with active components. Such agents may be useful in improving the properties of very insoluble and/or unstable actives. In general, these substances are doughnut-shaped molecules with hydrophobic internal cavities and hydrophilic exteriors. Insoluble and/or instable actives may fit within the hydrophobic cavity, thereby producing an inclusion complex, which is soluble in water. Accordingly, the formation of the inclusion complex permits very insoluble and/or instable actives to be dissolved in water. A particularly desirable example of such agents are cyclodextrins, which are cyclic carbohydrates derived from starch. Other similar substances, however, are considered well within the scope of the present invention.

The various embodiments of the invention may include penetration and permeation enhancers. Among such useful enhancers are included medium chain mono- and diacylglycerol fatty acid derivative, such as glycerol laurate, and mixtures thereof; synthetic and natural surfactants and mixtures thereof; medium chain fatty acids and salts and esters thereof, including mono-, di- and triglycerides such as sodium caprylate and sodium caprate and mixtures thereof; bile salts; chelating agents, such as EDTA; detergents; cylodextrins, enamine derivatives, phospholipids, lecithins, cetomacrogels, sodium salicylate, sodium-5-methoxysalicyclic acid; glycerol and polyethylene glycol estess such as those sold under the name Labrasol; zonula occludens toxin; and alkyl glycosides. Additionally, combinations of penetration and permeation enhancers from different classes are also useful.

Additional permeation enhancers include, Polysorbate 80, phosphatidylcholine, nmethylpiperazine, sodium salicylate, melittin, and palmitoyl carnitine chloride (pcc). 23-lauryl ether, aprotinin, azone, benzalkonium chloride, cetylpyridinium chloride, cetyltrimethylammonium bromide, cyclodextrin, dextran sulfate, lauric acid, lauric acid/propylene glycol, lysophosphatidylcholine, menthol, methoxysalicylate, methyloleate, oleic acid, phosphatidylcholine, polyoxyethylene, sodium edta, sodium glycocholate, sodium taurocholate, sodium lauryl sulfate, sodium salicylate, sodium glycodeoxycholate, sodium taurodeoxycholate, sulfoxides, and combinations thereof.

Additional permeation and or penetration enhancers include dimethylsulfoxide, decylmethylsulfoxide, alkysulfoxides:

Alkanols, such as ethanol, propanol, butanol, pentanol, hexanol, octanolnonanol, decanol, 2-butanol, 2-pentanol, benzyl alcohol:

Fatty acids and their corresponding alcohols, such as caprylic, decyl, lauryl, 2-lauryl, myristly, cetyl, stearyl oleyl, linoleyl, linolenyll alcohol;

Linear carboxylic acids such as valeric, heptanoic, pelagonic, caproic, capric, lauric, Myristic, stearic, oleic, caprylic; Branched carboxylic acids such as isovaleric, neopentanoic, neoheptanoic, neononanoic, trimethyl hexanoic, neodecanoic, isostearic; fatty acid esters, such as aliphatic-isopropyl n-butyrate, isopropyl n-hexanoate, isopropyl n-decanoate, isopropyl myristate, isopropyl palmitate, octyldodecyl myristate; Alkyl esters such as ethyl acetate, butyl acetate, methyl acetate, methylvalerate, methylpropionate, diethyl sebacate, ethyl oleate; propylene glycol, polyethylene glycol, ethylene glycol, diethylene glycol, triethylene glycol, dipropylene glycol, glycerol, propanediol, butanediol, pentanediol, hexanetriol, urea, dimethylacetamide, diethyltoluamide, dimethylformamide, dimethyloctamide, dimethyldecamide; biodegradable cyclic urea, such as 1-alkyl-4-imidazolin-2-one; Pyrrolidone derivatives, such as 1-methyl-2-pyrrolidone, 2-pyrrolidone, 1-lauryl-2-pyrrolidone, 1-methyl-4-carboxy-2-pyrrolidone, 1-hexyl-4-carboxy-2-pyrrolidone, 1-lauryl-4-carboxy-2pyrrolidone, 1-methyl1-4-methoxycarbonyl-2-pyrrolidone, 1-hexyl-4-methoxycarbonyl-2 pyrrolidone, 1-lauryl-4-methoxycarbonyl-2-pyrrolidone, N-cyclohexylpyrrolidone, N-dimethylaminopropylpyrrolidone, N-cocoalkypyrrolidone, N-tallowalkylpyrrolidone; biodegradable pyrrolidone derivatives such as the fatty acid esters of N-(2-hydroxyethyl)-2-pyrrolidone; Cyclic amides such as 1-dodecylazacycloheptane-2-one (Azone), 1-geranylazacycloheptan-2-one, 1 farnesylazacycloheptan-2-one, 1-teranylgeranylazacycloheptan-2-one, 1-(3,7-dimethyloctyl)azacycloheptan-2-one, 1-(3,7,11-trimethyldodecyl)azacyclohaptan-2-one, 1-geranylazacyclohexane-2-one, 1-geranylazacyclopentan-2,5-dione, 1-farnesylazacyclopentan-2-one; Hexamethylenelauramide and its derivatives; diethanolamine, triethanolamine; Anionic surfactants such as sodium laurate, sodium lauryl sulphate; Cationic surfactants such as cetyltrimethyl ammonium bromide, tetradecyltrimethylammonium bromide, benzalkonium chloride, octadecyltrimethylammonium chloride, cetylpyridinium chloride, dodecyltrimethylammonium chloride, hexadecyltrimethylammonium chloride;
Nonionic surfactants such as those sold under the tradenames Poloxamer (231, 182, 184), Brij (30, 93, 96, 99), Span (20, 40, 60, 80, 85), Tween (20, 40, 60, 80),
Myrj (45, 51, 52), Miglyol 840; Bile salts such as Sodium cholate, sodium salts of taurocholic, Glycholic, desoxycholic acids; lecithin; Hydrocarbons such as D-Limonene, a-pinene, B-carene; Alcohols such as a-Terpineol, terpinen-4-ol, carvol; Ketones such as carvone, pulegonee, piperitone, menthone; Oxides such as cyclohexene ocide, limonene oxide, a-pinene oxice,
cyclopentene oxide, 1,8-cineole; Oils such as Ylang ylang, anise, chenopodium, eucalyptus; N-heptane, N-octane, N-nonane, N-decane, N-undecane, N-dodecane, N-tridecane, N-tetradecane, N-hexadecane;
Salicylic acid and salicylates (including their methyl, ethyl, and propyl glycol derivatives); citric and succinic acid.

As previously stated, combinations of penetration and permeation enhancers from different classes are also useful.

Forming the Film

The films of the present invention may be formed into a film strip or a sheet prior to drying. After the desired components are combined to form a multi-component matrix, including the polymer, water, and nanoparticles, as well as any other component as desired, the combination is formed into a sheet or film, by any method known in the art such as coating, spreading, casting or drawing the multi-component matrix. If a multi-layered film is desired, this may be accomplished by co-extruding more than one combination of components which may be of the same or different composition. A multi-layered film may also be achieved by coating, spreading, or casting a combination onto an already formed film layer, thus forming a multi-layered film with the already formed film layer and a second layer. The already formed film layer may be the same or may be different than the second layer. The already formed film layer may be partially dried when the second layer is coated, spread, or cast onto its surface, or it may be fully dried to a desired solvent content. The already formed film layer may be dissolvable or disintegrable, and its dissolution or disintegration time may be longer or shorter than that of the second film layer.

A number of techniques may be employed in the mixing stage to prevent bubble inclusions in the final film. To provide a composition mixture with substantially no air bubble formation in the final product, anti-foaming or surface-tension reducing agents are employed. Additionally, the speed of the mixture is desirably controlled to prevent cavitation of the mixture in a manner which pulls air into the mix. Finally, air bubble reduction can further be achieved by allowing the mix to stand for a sufficient time for bubbles to escape prior to drying the film. Desirably, the inventive process first forms a masterbatch of film-forming components without active ingredients or volatile materials. In one embodiment, the active(s) are combined with smaller mixes of the masterbatch just prior to casting. Thus, the masterbatch pre-mix can be allowed to stand for a longer time without concern for instability of the active agent or other ingredients.

Although a variety of different film-forming techniques may be used, it is desirable to select a method that will provide a flexible film, such as reverse roll coating. The flexibility of the film allows for the sheets of film to be rolled and transported for storage or prior to being cut into individual dosage forms. Desirably, the films will also be self-supporting or, in other words, able to maintain their integrity and structure in the absence of a separate support. Furthermore, the films of the present invention may be selected of materials that are edible or ingestible.

Casting or Depositing the Film Composition

The invention uses processes for making self-supporting films having a substantially uniform distribution of components. The self supporting film is particularly useful for delivery of actives as discussed herein. The processes for making the film are designed to maintain the compositional uniformity of components distributed throughout the film, which is particularly necessary when actives, such as pharmaceutical actives, are incorporated into the film. In the pharmaceutical context, it is essential that the film is compositionally uniform so that it can be divided into individual film dosage units, each dosage unit having the appropriate amount of active when administered, such that regulatory approval can be secured.

The process may further include the preliminary steps of forming a masterbatch premix of an edible water-soluble polymer and water; optionally deaerating the premix (such as by mixing); feeding a predetermining amount of the premix to at least one mixer; adding the nanoparticles to the mixer; and mixing the components to achieve a uniform distribution thereof. Thereafter, the wet film is formed and dried.

Coating or casting methods are particularly useful for the purpose of forming the films of the present invention. Specific examples include reverse roll coating, gravure coating, immersion or dip coating, metering rod or meyer bar coating, slot die or extrusion coating, gap or knife over roll coating, air knife coating, curtain coating, or combinations thereof, especially when a multi-layered film is desired.

Roll coating, or more specifically reverse roll coating, is particularly desired when forming films in accordance with the present invention. This procedure provides excellent control and uniformity of the resulting films, which is desired in the present invention. In this procedure, the coating material is measured onto the applicator roller by the precision setting of the gap between the upper metering roller and the application roller below it. The coating is transferred from the application roller to the substrate as it passes around the support roller adjacent to the application roller. Both three roll and four roll processes are common.

The gravure coating process relies on an engraved roller running in a coating bath, which fills the engraved dots or lines of the roller with the coating material. The excess coating on the roller is wiped off by a doctor blade and the coating is then deposited onto the substrate as it passes between the engraved roller and a pressure roller.

Offset Gravure is common, where the coating is deposited on an intermediate roller before transfer to the substrate.

In the simple process of immersion or dip coating, the substrate is dipped into a bath of the coating, which is normally of a low viscosity to enable the coating to run back into the bath as the substrate emerges.

In the metering rod coating process, an excess of the coating is deposited onto the substrate as it passes over the bath roller. The wire-wound metering rod, sometimes known as a Meyer Bar, allows the desired quantity of the coating to remain on the substrate. The quantity is determined by the diameter of the wire used on the rod.

In the slot die process, the coating is squeezed out by gravity or under pressure through a slot and onto the substrate. If the coating is 100% solids, the process is termed "Extrusion" and in this case, the line speed is frequently much faster than the speed of the extrusion. This enables coatings to be considerably thinner than the width of the slot.

The gap or knife over roll process relies on a coating being applied to the substrate which then passes through a "gap" between a "knife" and a support roller. As the coating and substrate pass through, the excess is scraped off.

Air knife coating is where the coating is applied to the substrate and the excess is "blown off" by a powerful jet from the air knife. This procedure is useful for aqueous coatings.

In the curtain coating process, a bath with a slot in the base allows a continuous curtain of the coating to fall into the gap between two conveyors. The object to be coated is passed along the conveyor at a controlled speed and so receives the coating on its upper face.

Drying the Film

The drying step can also be a contributing factor with regard to maintaining the uniformity of the film composition. A controlled drying process is particularly important when, in the absence of a viscosity increasing composition or a composition in which the viscosity is controlled, for example by the selection of the polymer, the components within the film may have an increased tendency to aggregate or conglomerate. An alternative method of forming a film with an accurate dosage, that would not necessitate the controlled drying process, would be to cast the films on a predetermined well. With this method, although the components may aggregate, this will not result in the migration of the active to an adjacent dosage form, since each well may define the dosage unit per se.

One process used to make the films is described in U.S. Pat. No. 7,425,292, which is incorporated in its entirety herein by reference. In this process, the films are prepared by rapidly forming a visco-elastic film by applying hot air currents to the film to prevent flow migration and intermolecular forces from creating aggregates or conglomerates thereby maintaining compositional uniform distribution of components in the film; and further drying the visco-elastic film to form a self-supporting film.

The wet film forming matrix first may be fed onto the top side of a surface prior to the application of hot air currents. The wet film is desirably formed from a deaerated matrix within a time period before the active contained therein degrades. The process may further include a step of dividing the dried film into individual dosage units of equal dimensions and compositional make-up. There may be hot air currents applied to the top surface, if desired. In such embodiments, it may be desired that hot air currents be applied to the bottom surface of the film at a higher velocity than to the top surface of the film during drying. Hot air currents applied to dry the top of the films are preferably less than that which would cause surface rippling or skinning. This permits the film to sufficiently thicken in viscosity to lock-in volumetric uniformity while permitting evaporation of water through the non-skinned surface.

When a controlled or rapid drying process is used, liquid carriers are removed from the film in a manner such that the uniformity, or more specifically, the non-self-aggregating uniform heterogeneity, that is obtained in the wet film is maintained.

Desirably, the film is rapidly dried, such that a solid, visco-elastic structure is initially formed and the contents of the film are "locked in". This can take place within the first few minutes, e.g. about the first 0.5 to about 15 minutes, desirably about the first 10 minutes, and most desirably about the first 4.0 minutes of the drying process. This rapid drying may be achieved by increasing the viscosity of the film at the initiation of the drying process, such as by initially exposing the film to a drying source, such as heat or radiation energy. Rapid drying means that the film product's viscosity begins to develop at the initiation of the drying process to lock in the uniformity of the active content as described above. The rapid increase in viscosity is achieved at the initial stage of drying because the initial rate of heat transfer in the film should be sufficiently high in order to achieve the visco-elastic film formation.

It may be desired to limit the amount of top air flow during this initial drying stage. Controlling the drying in this manner prevents the destruction and reformation of the film's top surface, which results from conventional drying methods. This is accomplished by forming the film and placing it on the top side of a surface having top and bottom sides. Then, heat is initially applied to the bottom side of the film to provide the necessary energy to evaporate or otherwise remove the liquid carrier. The films dried in this manner dry more quickly and evenly as compared to air-dried films, or those dried by conventional drying means. In contrast to an air-dried film that dries first at the top and edges, the films dried by applying heat to the bottom dry simultaneously at the center as well as at the edges. This also prevents settling of ingredients that occurs with films dried by conventional means.

The internal temperature of the film forming matrix during drying is desirably about 100° C. or less, desirably about 70° C. or less, and most desirably about 60° C. or less. It may be desired to dry the film such that the temperature within the film is less than the boiling point of any solvent or solvents that are within the film forming matrix. Further, it is desirable that the temperature within the film forming matrix is maintained below a temperature at which substantial degradation of actives contained within the film will occur. It is noted, however, that the temperature outside of the film may be above the temperature within the film, and in some instances may be substantially higher than the temperature within the film. The interior of the film remains at a temperature below which substantial degradation of the active contained therein occurs. It is generally understood that some degradation of the active may occur, but such degradation should not be of a substantial amount such that the uniformity of the non-degraded active content is outside the uniformity levels set forth above. That is, unit doses cut from the film should not vary from each other or from the target level of active by about 10% of viable, non-degraded active content.

Another method of controlling the drying process, which may be used alone or in combination with other controlled methods as disclosed above includes controlling and modifying the humidity within the drying apparatus where the film is being dried. In this manner, the premature drying of the top surface of the film may be avoided.

Another method of drying tracks that previously set forth by Magoon, which is based on an interesting property of water. Although water transmits energy by conduction and convection both within and to its surroundings, water only radiates energy within and to water. Therefore, the apparatus of Magoon includes a surface onto which the fruit pulp is placed that is transparent to infrared radiation. The underside of the surface is in contact with a temperature controlled water bath. The water bath temperature is desirably controlled at a temperature slightly below the boiling temperature of water. When the wet fruit pulp is placed on the surface of the apparatus, this creates a "refractance window." This means that infrared energy is permitted to radiate through the surface only to the area on the surface occupied by the fruit pulp, and only until the fruit pulp is dry. The apparatus of Magoon provides the films of the present invention with an efficient drying time reducing the instance of aggregation of the components of the film.

The objective of the drying processes described herein is to provide a method of drying the films that avoids complications, such as the noted "rippling" effect, that are associated with conventional drying methods and which initially dry the upper surface of the film, trapping moisture inside. In conventional oven drying methods, as the moisture trapped inside subsequently evaporates, the top surface is altered by being ripped open and then reformed.

These complications are avoided by the present drying methods, and a uniform film is provided by drying the bottom surface of the film first or otherwise preventing the formation of polymer film formation (skin) on the top surface of the film prior to drying the depth of the film. This may be achieved by applying heat as described above, or alternatively by the introduction of radiation (such as controlled microwaves) to evaporate the water or other polar solvent within the film. In some embodiments, the film is rapidly dried so as to form a visco-elastic structure within the first ten minutes of drying, and more particularly within the first four minutes of drying. Desirably, the film is dried at such a rapid rate that any components, including the nanoparticles, do not undesirably aggregate together. By rapidly drying the wet matrix, a substantial number of the nanoparticles do not have time to agglomerate.

Yet alternatively, drying may be achieved by using balanced fluid flow, such as balanced air flow, where the bottom and top air flows are controlled to provide a uniform film. In such a case, the air flow directed at the top of the film should not create a condition which would cause movement of particles present in the wet film, due to forces generated by the air currents, that is, any top air flow that is present during this drying stage should be insufficient to overcome the inherent viscosity of the film surface. Additionally, any air currents directed at the bottom of the film should desirably be controlled such that the film does not lift up due to forces from the air. There may be more top air currents than bottom air currents, so long as the air currents are controlled so as to avoid skinning, rippling, or movement of particles within the matrix that results in undesirable agglomeration or non-uniformity. Uncontrolled air currents, either above or below the film, can create non-uniformity in the final film products. The humidity level of the area surrounding the top surface may also be appropriately adjusted to prevent premature closure or skinning of the polymer surface.

The present invention yields exceptionally uniform film products when attention is paid to reducing the aggregation of the compositional components. By avoiding the introduction of and eliminating excessive air in the mixing process, selecting polymers and solvents to provide a controllable viscosity and by drying the film in a rapid manner from the bottom up, such films result. Various drying methods include those set forth in U.S. Pat. Nos. 7,425,292 and 7,357,891, which are herein incorporated by reference in their entireties.

The films may initially have a thickness of about 500 μm to about 1,500 μm, or about 20 mils to about 60 mils, and when dried have a thickness from about 3 μm to about 250 μm, or about 0.1 mils to about 10 mils. In some embodiments, the film product has a thickness of greater than 0.1 mils. In some other embodiments, the film product has a thickness of about 10 mils or fewer. In some further embodiments, the film product has a thickness of about 0.5 mils to about 5 mils. Desirably, the dried films will have a thickness of about 2 mils to about 8 mils, and more desirably, from about 3 mils to about 6 mils.

Extruding the Film Composition

In alternative embodiments, the film products of the present invention may be formed by extrusion rather than casting or deposition methods. Extrusion is particularly useful for film compositions containing polyethylene oxide-based polymer components, as discussed below. For instance, a single screw extrusion process may be employed in accordance with the present invention. According to such an extrusion process, pressure builds in the polymer melt so that it may be extruded through a die or injected into a mold.

It may be particularly desirable to employ extrusion methods for forming film compositions containing PEO polymer components. These compositions contain PEO or PEO blends in the polymer component, and may be essentially free of added plasticizers, and/or surfactants, and polyalcohols.

The compositions may be extruded as a sheet at processing temperatures of less than about 90° C. Extrusion may proceed by squeezing the film composition through rollers or a die to obtain a uniform matrix. The extruded film composition then is cooled by any mechanism known to those of ordinary skill in the art. For example, chill rollers, air cooling beds, or water cooling beds may be employed. The cooling step is particularly desirable for film compositions containing PEO polymer components because PEO tends to hold heat. The thus formed sheets can be formed into various shapes, as desired.

Uses of Thin Films

The thin films of the present invention are well suited for many uses. The high degree of uniformity of the components of the film makes them particularly well suited for incorporating pharmaceuticals. Furthermore, the polymers used in construction of the films may be chosen to allow for a range of disintegration times for the films. A variation or extension in the time over which a film will disintegrate may achieve control over the rate that the active is released, which may allow for a sustained release delivery system. In addition, the films may be used for the administration of nanoparticles to skin and other body surfaces, including those with mucous membranes.

The films may be used to administer nanoparticles through topical, oral, or any other administration desired. The films may also be reconstituted in a suitable liquid carrier and subsequently administered by injection or infusion. Administration may be accomplished by preparing the film as described above, introducing the film to a skin or mucosal surface of a mammal, and wetting the film if necessary, for example. If desired, this film may be prepared and adhered to a second or support layer from which it is removed prior to use, i.e. application to the skin. An adhesive may be used to attach the film to the support or backing material, which may be any of those known in the art, and is preferably not water soluble. If an adhesive is used, it will desirably be an adhesive that does not alter the properties of the active. Mucoadhesive compositions are also useful. The film compositions in many cases serve as mucoadhesives themselves.

The films of the present invention take advantage of the films' tendency to dissolve quickly when wetted, i.e., through contact with a wetting agent such as water or saliva. The nanoparticles may be introduced to a liquid by preparing a film in accordance with the present invention, introducing it to a liquid, and allowing the film to dissolve. This may be used to prepare a liquid dosage form of the nanoparticles, which may then be administered to the user.

The following is presented by way of example and is not to be construed as a limitation to the scope of the claims.

EXAMPLES

Example 1

Preparation of Ligands

Preparation of 2-thio-ethyl-α-D-galactoside (α-galactose C2SH)

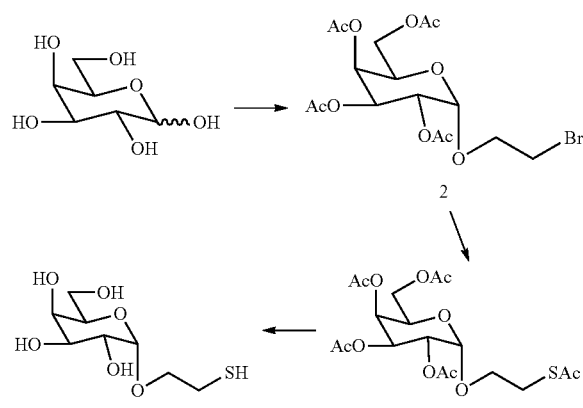

To a suspension of galactose (3 g, 16.65 mmol) in 2-bromoethanol (30 ml), acid resin Amberlite 120-His added to reach pH 2. The reaction is stirred for 16 hours at 50-60° C. The reaction mixture is filtered and washed with MeOH. Triethylamine is added to reach pH 8. The crude of the reaction is concentrated and co evaporated 3 times with toluene. The reaction mixture is dissolved pyridine (75 mL) and Ac2O (35 mL) and a catalytic amount of DMAP are added at 0° C. and stirred for 3 h at rt. The mixture is diluted with AcOEt and washed with 1.$H_2O$; 2.HCl (10%)3. $NaHCO_3$ dis 4. $H_2O$. The organic layer is collected and dried over anhydrous $Na_2SO_4$. TLC (Hexane:AcOEt 3:1, 2 elutions) shows a major product (desired) and a lower Rf minority. The product is purified by flash chromatography using the mixture hexane:ethyl acetate 6:1 as eluyent and the 2-bromoethyl-alpha-galactoside (2) is obtained.

The product of the previous reaction, 2 is dissolved in 27 ml of 2-butanone. To this solution, a catalytic amount of tetrabutylammonium iodide and 4 equivalents of potassium thioacetate are added. The resulting suspension is stirred for 2 hours at room temperature. Throughout this period the reaction is tested by TLC (hexane-AcOEt 2:1, 2 elutions) for the disappearance of the starting material. The mixture is diluted with 20 ml of AcOEt and washed with a saturated NaCl solution. The organic phase is dried, filtered and evaporated under vacuum. The product is purified in hexane/AcOEt 2:1→1:1 to obtain the acetylthio-alpha-galactoside 3.

The new product of the reaction, 3 is dissolved in a mixture dichloromethane-methanol 2:1. To this mixture a solution of 1N sodium methoxide (1 equivalent) is added and stirred for 1 hour at room temperature. Amberlite IR-120H resin is added to achieve pH 5-6. The resulting mixture is then filtered and concentrated to dryness to obtain the final product (a-galactose C2SH).

Preparation of Amino-thiol Linker.

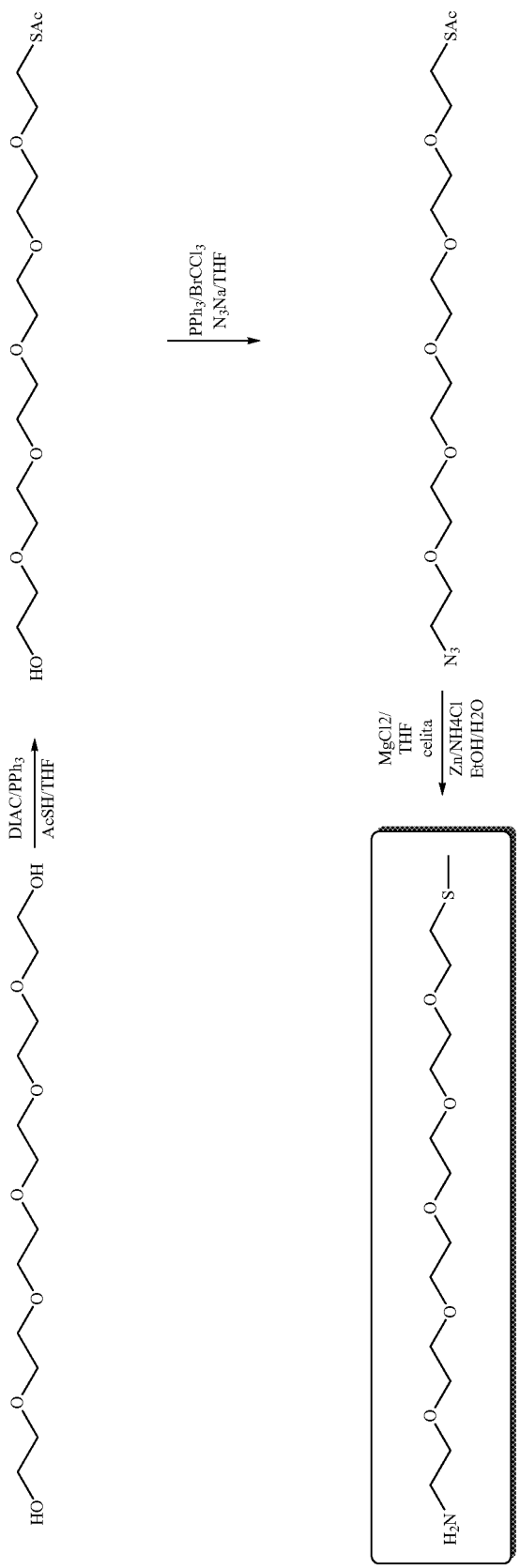

To a solution of PPh₃ (3 g, 11.4 mmol) in 20 ml dry THF, DIAC (2.3 g, 11.4 mmol) is added. The mixture is allowed to stir at 0° C. 15 min until the appearance of a white product. To this mixture a solution of hexaethyleneglycol (1.45 mL, 5.7 mmol) and HSAc (610 µl, 8.55 mmol) in dry THF (20 mL) is added dropwise (addition funnel). After 15 min the products begin to appear on TLC at Rf 0.2. The solution is concentrated in an evaporator. The crude of the reaction is dissolved in 50 ml of dichloromethane and washed with a solution of $K_2CO_3$ 10%. The organic phase is dried over anhydrous $Na_2SO_4$, filtered and concentrated under vacuum. Flash chromatography of the crude using AcOEt:Hexane 1:1, AcOEt and finally DCM:MeOH 4:1 as eluyent gave the acetyl-thio-hexaethyleneglycol derivative.

The reaction product is dissolved in 5 ml of DMF and PPh₃ (2.25 g, 8.55 mmol), NaN₃ (0.741 g, 11.4 mmol) and BrCl₃C (0,845 ml, 8.55 mmol) are added and the solution subsequently stirred for 40 min at room temperature. The resulting product has a higher Rf than the starting product when performing TLC (DCM:MeOH 25:1). The reaction mixture is diluted with 100 ml of diethylether and washed three times with $H_2O$. The organic phase is dried over anhydrous $Na_2SO_4$, filtered and evaporated under vacuum. The product is purified by flash chromatography using the mixture of eluyents DMC/MeOH 200:1 and DCM/MeOH 40:1 to obtain the azido-acetylthio-hexaethyleneglycol derivative.

To remove the triphenyl phosphine oxide, the reaction product is dissolved in 10 ml of THF and 0.5 g of $MgCl_2$ is added to this solution. The reaction is stirred for 2 h at 80° C. until a white precipitate appears and then is filtered through celite. The product is dissolved in a mixture of ethanol:$H_2O$ 3:1 and added Zn dust (0.45 g, 6.84 mmol) and $NH_4Cl$ (0.6 g, 11.4 mmol). The reaction was stirred at reflux for 1 h until the presence of starting material is no longer detectable by TLC (DCM/MeOH 25:1). The reaction is filtered through celite and the solvent is evaporated. The crude de reaction is diluted with AcOEt and extract with 5 ml $H_2O$. The aqueous phase is evaporated to dryness to obtain the amino-thiol-hexaethylenglycol product.

Example 2

Preparation of Mixed Gold Nanoparticles

Beta-glucose C2 derivative 1, N-acetylglucosamine C2 derivative 2, alpha-galactose C2 derivative 3, alpha-glucose C2 derivative 4, glucosamine C5 derivative 5 and hexaethyleneglycol amine linker 6 were taken from Midatech Biogune stock. N-(3-Dimethylaminopropyl)-N'-ethylcarbodiimide hydrochloride (EDC.HCl), $HAuCl_4$, $NaBH_4$ were purchased from Sigma-Aldrich Chemical Company. Imidazole-4-acetic acid monohydrochloride was purchased from Alfa Aesar. Company High quality MeOH and Nanopure water (18.1 mΩ) were used for all experiments and solutions.

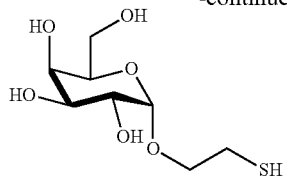

1

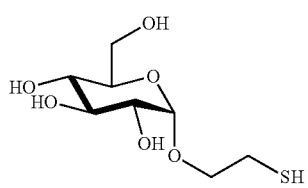

2

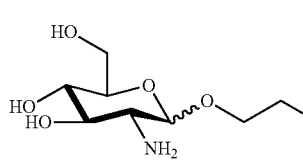

3

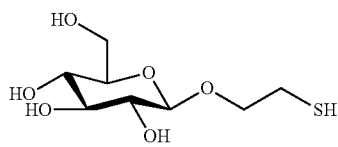

4

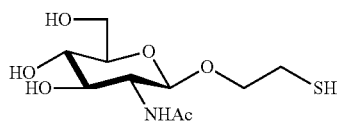

5

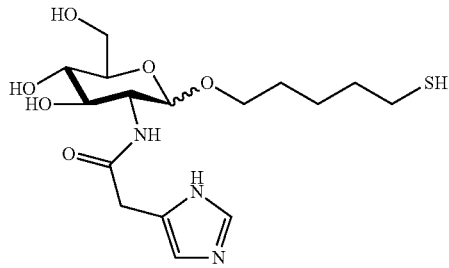

6

Nomenclature of the Ligands

GlcC2

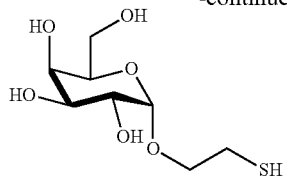

2'-thioethyl-β-D-glucopyranoside (beta)

GlcNHAcC2

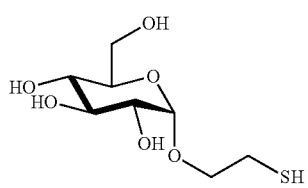

2'-thioethyl-2-acetamido-2-deoxy-β-D-glucopyranoside (beta)

GlcNH2-IAA-C5

5'-thiopentanyl-2-deoxy-2-imidazolacetamido-α,β-D-glucopyranoside (alpha, beta mix of isomers)

α-GalC2 (alpha)

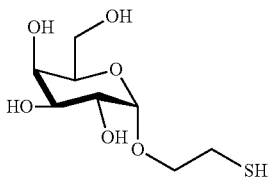

2'-thioethyl-α-D-galactopyranoside (alpha)

α-GlcC2 (alpha)

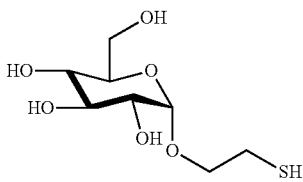

2'-thioethyl-α-D-glucopyranoside

EG6NH2

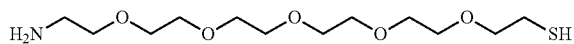

1-amino-17-mercapto-3,6,9,12,15,-pentaoxa-heptadecanol or 1-amino-6-mercapto-hexaethylenglycol (vulgar name)

Preparation of Nanoparticles (NP) Having a Plurality of Ligands

NP-GlcC2(9)GlcNAc(1)

To a solution of 1 (21.6 mg, 90 μmol) and 2(2.8 mg, 10 μmol) in MeOH (8.3 mL) a 0.025M aqueous solution of $HAuCl_4$ (1.33 mL, 33 μmol) was added. The solution was shaken during 30 seconds and then an aqueous solution of $NaBH_4$ 1N (0.67 mL, 0.67 mmol) was added in several portions (134 μL×5). The dark suspension was shaken during 100 minutes. The methanol layer was removed and the pellet was dissolved in 10 mL of water and purified by centrifugal filtering (10 KDa AMICON 4 mL, 4500 g, 15 min, 15° C.). The process was repeated three times, washing with 2 mL of water. The residue was dissolved in 7 mL of water. An aliquot was freeze dried for quantitation.

[NP]=0.8 mg/mL.

Without wishing to be bound by any theory, a schematic representation of the resulting nanoparticles having a plurality of ligands in the ratio 9:1 of GlcC2:GlcNAc "NP-GlcC2 (9)GlcNAc(1)" is shown in FIG. 1.

NP-GlcC2(4)GlcNAc(1)

To a solution of 1 (19.2 mg, 80 μmol) and 2(5.6 mg, 20 μmol) in MeOH (8.3 mL) a 0.025M aqueous solution of $HAuCl_4$ (1.33 mL, 33 μmol) was added. The solution was shaken during 30 seconds and then an aqueous solution of $NaBH_4$ 1N (0.67 mL, 0.67 mmol) was added in several portions (134 μL×5). The dark suspension was shaken during 100 minutes. The methanol layer was removed and the pellet was dissolved in 10 mL of water and purified by centrifugal filtering (10 KDa AMICON 4 mL, 4500 g, 15 min, 15° C.). The process was repeated three times, washing with 2 mL of water. The residue was dissolved in 7 mL of water. An aliquot was freeze dried for quantitation.

[NP]=0.8 mg/mL.

Figure 2:
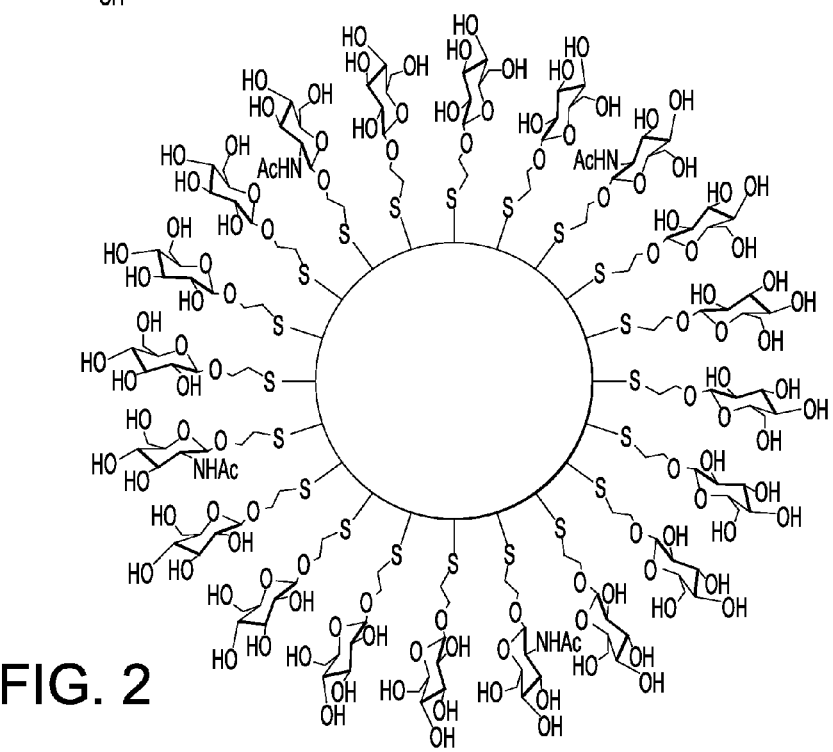
FIG. 2 shows a schematic representation of nanoparticles having a plurality of ligands in the ratio 4:1 of GlcC2:GlcNAc "NP-GlcC2(4)GlcNAc(1)"

Without wishing to be bound by any theory, a schematic representation of the resulting nanoparticles having a plurality of ligands in the ratio 4:1 of GlcC2:GlcNAc "NP-GlcC2 (4)GlcNAc(1)" is shown in FIG. 2.

NP-GlcC2(1)GlcNAc(1)

To a solution of 1 (12 mg, 50 μmol) and 2(14 mg, 50 μmol) in MeOH (8.3 mL) a 0.025M aqueous solution of $HAuCl_4$ (1.33 mL, 33 μmol) was added. The solution was shaken during 30 seconds and then an aqueous solution of $NaBH_4$ 1N (0.67 mL, 0.67 mmol) was added in several portions (134 μL×5). The dark suspension was shaken during 100 minutes. The methanol layer was removed and the pellet was dissolved in 10 mL of water and purified by centrifugal filtering (10 KDa AMICON 4 mL, 4500 g, 15 min, 15° C.). The process was repeated three times, washing with 2 mL of water. The residue was dissolved in 7 mL of water. An aliquot was freeze dried for quantitation.

[NP]=0.9 mg/mL.

Figure 3:
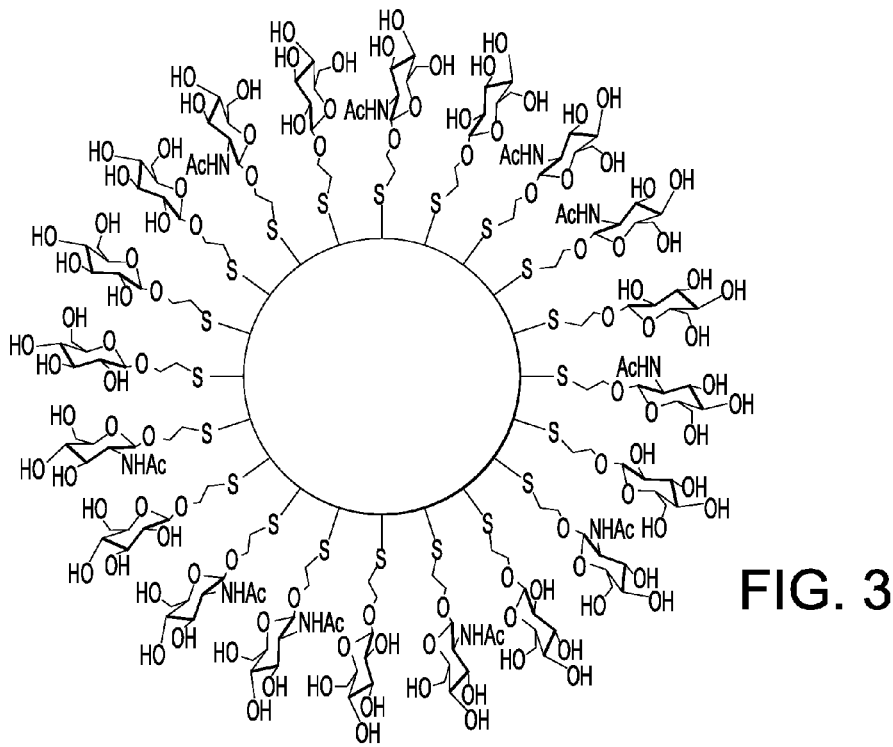
FIG. 3 shows a schematic representation of nanoparticles having a plurality of ligands in the ratio 1:1 of GlcC2:GlcNAc "NP-GlcC2(1)GlcNAc(1)"

Without wishing to be bound by any theory, a schematic representation of the resulting nanoparticles having a plurality of ligands in the ratio 1:1 of GlcC2:GlcNAc "NP-GlcC2 (1)GlcNAc(1)" is shown in FIG. 3.

NP-GlcC2(1)GlcNAc(9)

To a solution of 1 (2.4 mg, 10 μmol) and 2(25.3 mg, 90 μmol) in MeOH (8.3 mL) a 0.025M aqueous solution of $HAuCl_4$ (1.33 mL, 33 μmol) was added. The solution was shaken during 30 seconds and then an aqueous solution of $NaBH_4$ 1N (0.67 mL, 0.67 mmol) was added in several portions (134 μL×5). The dark suspension was shaken during 100 minutes. The methanol layer was removed and the pellet was dissolved in 10 mL of water and purified by centrifugal filtering (10 KDa AMICON 4 mL, 4500 g, 15 min, 15° C.). The process was repeated three times, washing with 2 mL of water. The residue was dissolved in 7 mL of water. An aliquot was freeze dried for quantitation.

[NP]=0.8 mg/mL.

Figure 4:
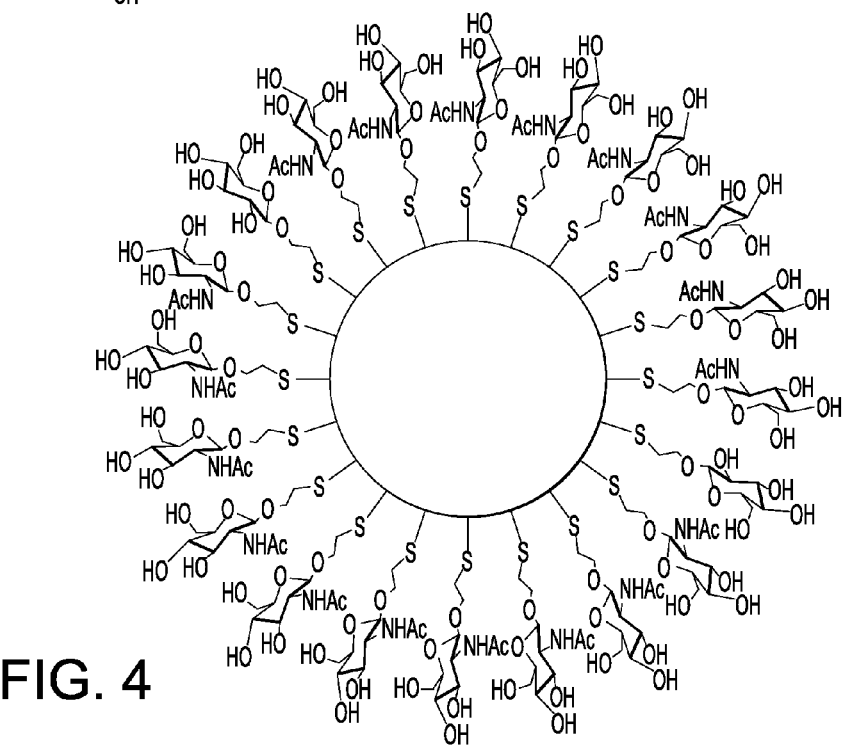
FIG. 4 shows a schematic representation of nanoparticles having a plurality of ligands in the ratio 1:9 of GlcC2:GlcNAc "NP-GlcC2(1)GlcNAc(9)"

Without wishing to be bound by any theory, a schematic representation of the resulting nanoparticles having a plurality of ligands in the ratio 1:9 of GlcC2:GlcNAc "NP-GlcC2 (1)GlcNAc(9)" is shown in FIG. 4.

NP-GlcC2(1)alpha-Gal(1)

To a solution of 1 (12 mg, 50 μmol) and 3 (12 mg, 50 μmol) in MeOH (8.3 mL) a 0.025M aqueous solution of $HAuCl_4$ (1.33 mL, 33 μmol) was added. The solution was shaken during 30 seconds and then an aqueous solution of $NaBH_4$ 1N (0.67 mL, 0.67 mmol) was added in several portions (134 μL×5). The dark suspension was shaken during 100 minutes. The methanol layer was removed and the pellet was dissolved in 10 mL of water and purified by centrifugal filtering (10 KDa AMICON 4 mL, 4500 g, 15 min, 15° C.). The process was repeated three times, washing with 2 mL of water. The residue was dissolved in 7 mL of water. An aliquot was freeze dried for quantitation. [NP]=0.7 mg/mL.

Figure 5:
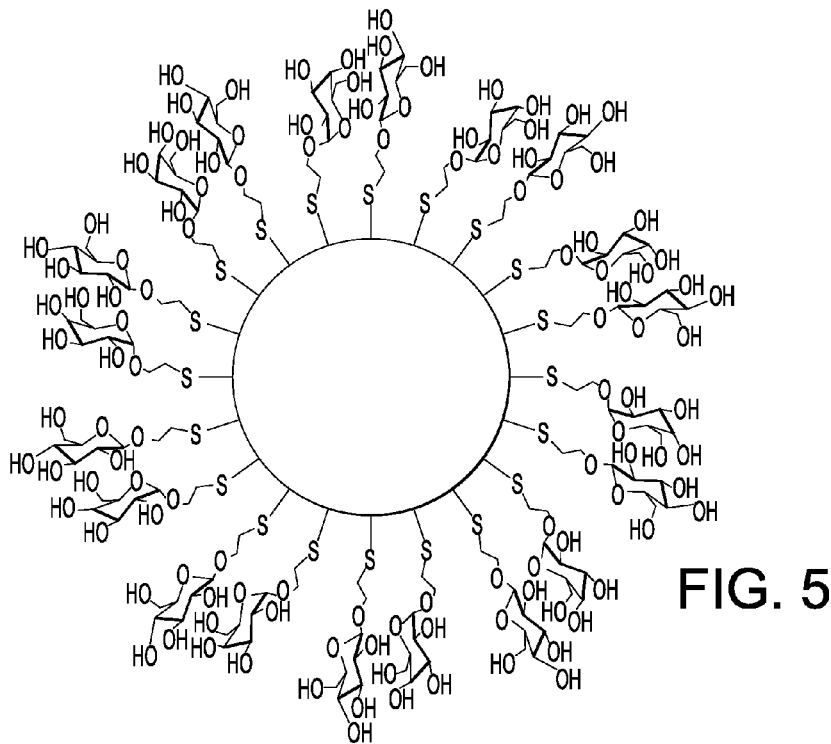
FIG. 5 shows a schematic representation of nanoparticles having a plurality of ligands in the ratio 1:1 of GlcC2:alpha-Gal "NP-GlcC2(1)alpha-Gal(1)"

Without wishing to be bound by any theory, a schematic representation of the resulting nanoparticles having a plurality of ligands in the ratio 1:1 of GlcC2:alpha-Gal "NP-GlcC2 (1)alpha-Gal(1)" is shown in FIG. 5.

NP-betaGlcC2(1)EG6NH2(1)

To a solution of 1 (12 mg, 50 µmol) and 6 (14.85 mg, 50 µmol) in MeOH (8.3 mL) a 0.025M aqueous solution of $HAuCl_4$ (1.33 mL, 33 µmol) was added. The solution was shaken during 30 seconds and then an aqueous solution of $NaBH_4$ 1N (0.67 mL, 0.67 mmol) was added in several portions (134 µL×5). The dark suspension was shaken during 100 minutes. The methanol layer was removed and the pellet was dissolved in 10 mL of water and purified by centrifugal filtering (10 KDa AMICON 4 mL, 4500 g, 15 min, 15° C.). The process was repeated three times, washing with 2 mL of water. The residue was dissolved in 7 mL of water. An aliquot was freeze dried for quantitation.

[NP]=0.9 mg/mL.

Figure 6:
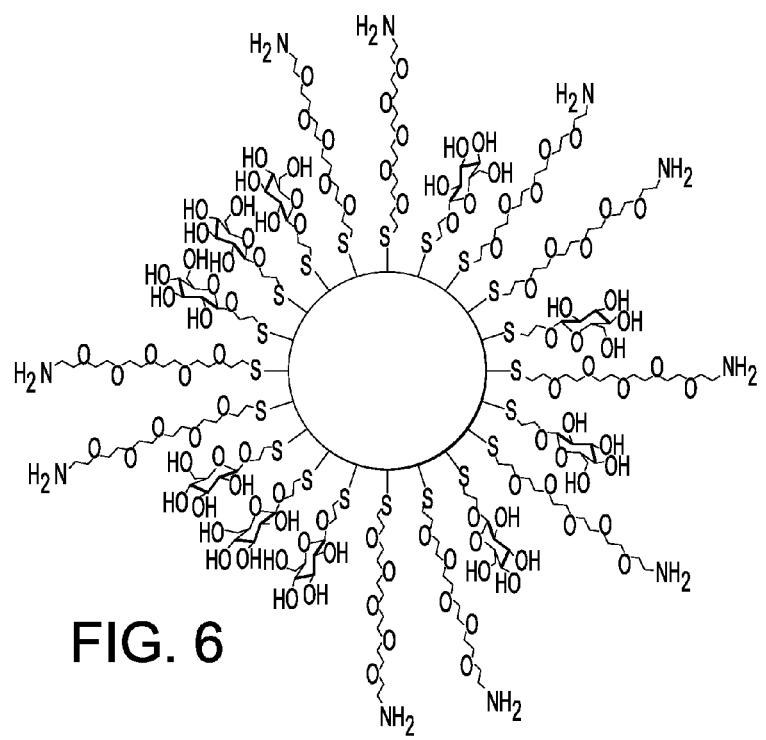
FIG. 6 shows a schematic representation of nanoparticles having a plurality of ligands in the ratio 1:1 of betaGlcC2:EG6NH2 "NP-betaGlcC2(1)EG6NH2(1)"

Without wishing to be bound by any theory, a schematic representation of the resulting nanoparticles having a plurality of ligands in the ratio 1:1 of betaGlcC2:EG6NH2 "NP-betaGlcC2(1)EG6NH2(1)" is shown in FIG. 6.

NP-GlcNHAc (1)EG6NH2(1)

To a solution of 2(14 mg, 50 µmol) and 6 (14.85 mg, 50 µmol) in MeOH (8.3 mL) a 0.025M aqueous solution of $HAuCl_4$ (1.33 mL, 33 µmol) was added. The solution was shaken during 30 seconds and then an aqueous solution of $NaBH_4$ 1N (0.67 mL, 0.67 mmol) was added in several portions (134 µL×5). The dark suspension was shaken during 100 minutes. The methanol layer was removed and the pellet was dissolved in 10 mL of water and purified by centrifugal filtering (10 KDa AMICON 4 mL, 4500 g, 15 min, 15° C.). The process was repeated three times, washing with 2 mL of water. The residue was dissolved in 6 mL of water. An aliquot was freeze dried for quantitation.

[NP]=0.6 mg/mL.

Figure 7:
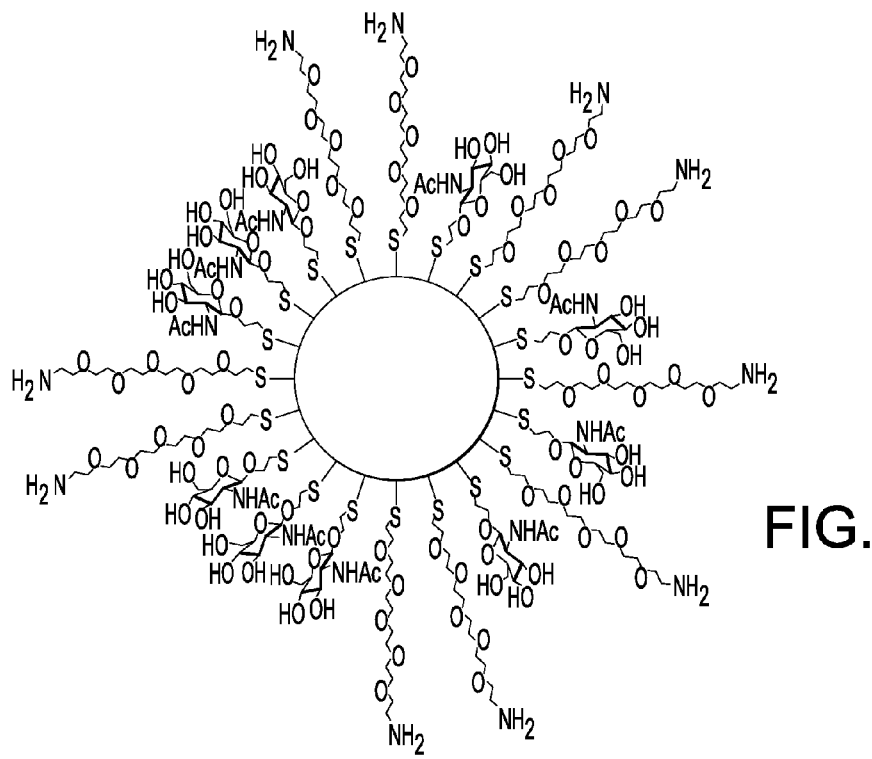
FIG. 7 shows a schematic representation of nanoparticles having a plurality of ligands in the ratio 1:1 of GlcNHAc:EG6NH2 "NP-GlcNHAc (1)EG6NH2(1)"

Without wishing to be bound by any theory, a schematic representation of the resulting nanoparticles having a plurality of ligands in the ratio 1:1 of GlcNHAc:EG6NH2 "NP-GlcNHAc(1)EG6NH2(1)" is shown in FIG. 7.

NP-alpha-Glc (1)EG6NH2(1)

To a solution of 4 (12 mg, 50 µmol) and 6 (14.85 mg, 50 µmol) in MeOH (8.3 mL) a 0.025M aqueous solution of $HAuCl_4$ (1.33 mL, 33 µmol) was added. The solution was shaken during 30 seconds and then an aqueous solution of $NaBH_4$ 1N (0.67 mL, 0.67 mmol) was added in several portions (134 µL×5). The dark suspension was shaken during 100 minutes. The methanol layer was removed and the pellet was dissolved in 10 mL of water and purified by centrifugal filtering (10 KDa AMICON 4 mL, 4500 g, 15 min, 15° C.). The process was repeated three times, washing with 2 mL of water. The residue was dissolved in 4 mL of water. An aliquot was freeze dried for quantitation.

[NP]=0.8 mg/mL.

Figure 8:
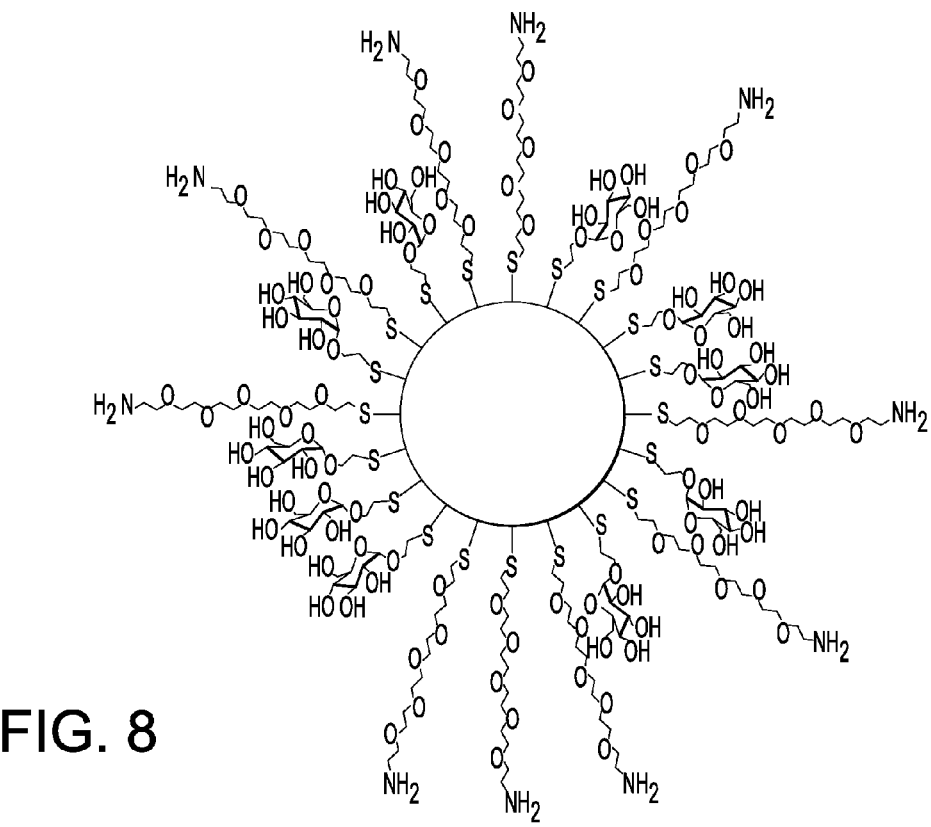
FIG. 8 shows a schematic representation of nanoparticles having a plurality of ligands in the ratio 1:1 of alpha-Glc:EG6NH2 "NP-alpha-Glc (1)EG6NH2(1)"

Without wishing to be bound by any theory, a schematic representation of the resulting nanoparticles having a plurality of ligands in the ratio 1:1 of alpha-Glc:EG6NH2 "NP-alpha-Glc (1)EG6NH2(1)" is shown in FIG. 8.

NP-alpha-Glc

To a solution of 4 (24 mg, 100 µmol) in MeOH (8.3 mL) a 0.025M aqueous solution of $HAuCl_4$ (1.33 mL, 33 µmol) was added. The solution was shaken during 30 seconds and then an aqueous solution of $NaBH_4$ 1N (0.67 mL, 0.67 mmol) was added in several portions (134 µL×5). The dark suspension was shaken during 100 minutes. The methanol layer was removed and the pellet was dissolved in 10 mL of water and purified by centrifugal filtering (10 KDa AMICON 4 mL, 4500 g, 15 min, 15° C.). The process was repeated three times, washing with 2 mL of water. The residue was dissolved in 5 mL of water. An aliquot was freeze dried for quantitation. [NP]=1.0 mg/mL.

Figure 9:
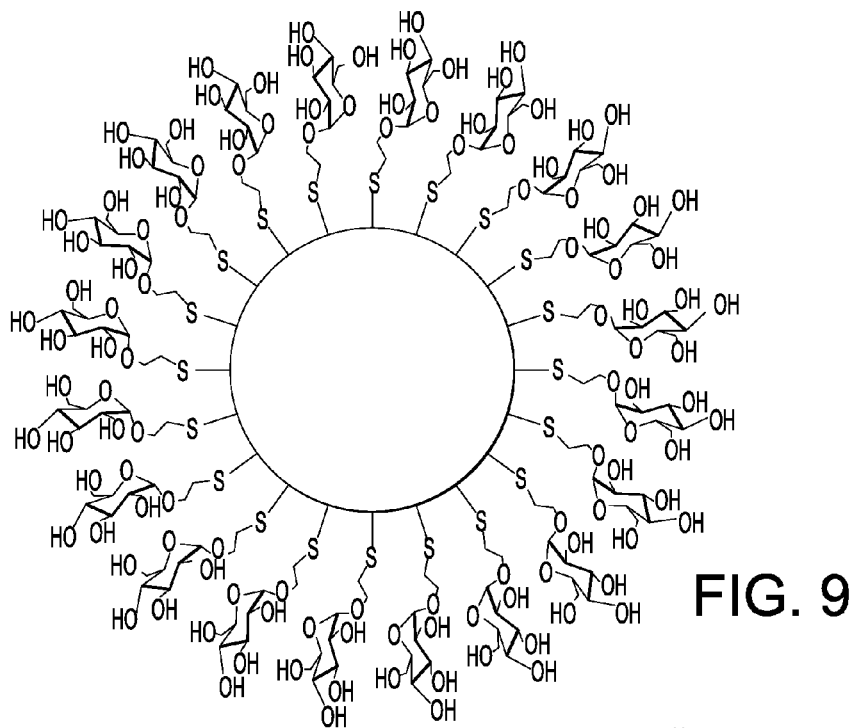
FIG. 9 shows a schematic representation of nanoparticles having a plurality of ligands of alpha-Glc "NP-alpha-Glc"

Without wishing to be bound by any theory, a schematic representation of the resulting nanoparticles having a plurality of ligands of alpha-Glc "NP-alpha-Glc" is shown in FIG. 9.

NP-GlcC2(1)GlcNH IAA (1)

To a solution of 1 (12 mg, 50 µmmol) and 5 (12 mg, 50 µmmol) in MeOH (8.3 mL) a 0.025M aqueous solution of $HAuCl_4$ (1.33 mL, 33 µmol) was added. The solution was shaken during 30 seconds and then an aqueous solution of $NaBH_4$ 1N (0.67 mL, 0.67 mmol) was added in several portions (134 µL×5). The dark suspension was shaken during 100 minutes. The methanol layer was removed and the pellet was dissolved in 10 mL of water and purified by centrifugal filtering (10 KDa AMICON 4 mL, 4500 g, 15 min, 15° C.). The process was repeated three times, washing with 2 mL of water. The residue was dissolved in 8 mL of 100 mM MES and treated with EDC (153 mg, 0.8 mmol) and imidazole-4-acetic acid monohydrochloride (81 mg, 0.5 mmol) for 14 hours. The mixture was and purified by centrifugal filtering (10 KDa AMICON 4 mL, 4500 g, 15 min, 15° C.). The process was repeated three times, washing with 2 mL of water. The residue was dissolved in 4 mL of water. An aliquot was freeze dried for quantitation. [NP]=0.9 mg/mL.

Figure 10:
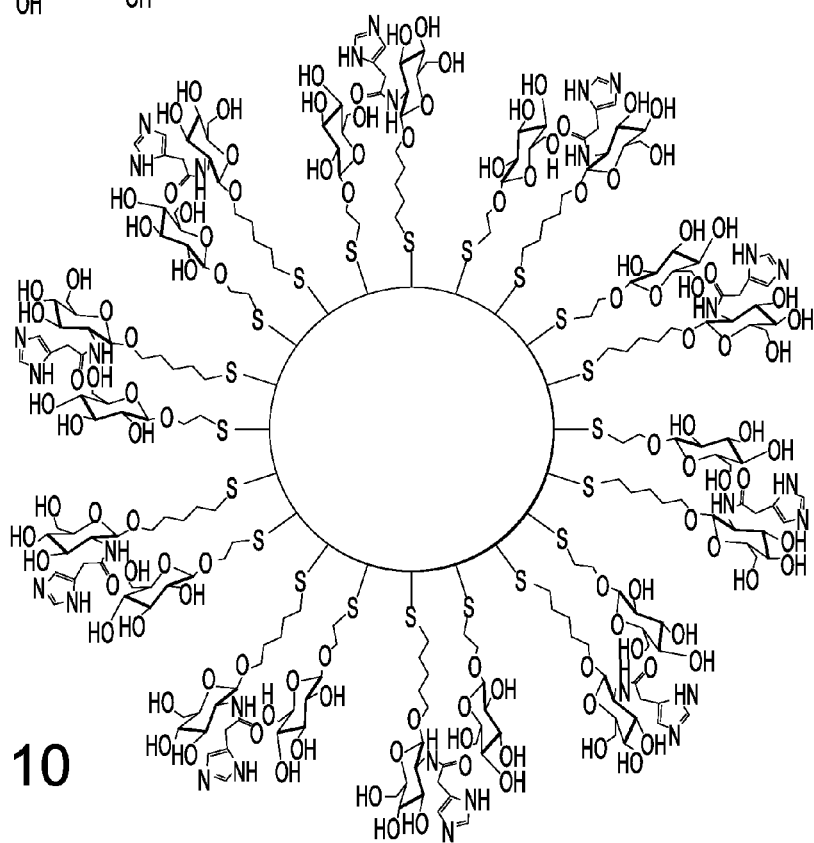
FIG. 10 shows a schematic representation of nanoparticles having a plurality of ligands in the ratio 1:1 of GlcC2:GlcN-H_IAA "NP-GlcC2(1)GlcNH_IAA (1)"

Without wishing to be bound by any theory, a schematic representation of the resulting nanoparticles having a plurality of ligands in the ratio 1:1 of GlcC2:GlcNH_IAA "NP-GlcC2(1)GlcNH_IAA (1)" is shown in FIG. 10.

NP-alpha-Gal(1)EG6NH2(1)

Preparation of amine alpha-gal gold nanoparticles Batch MI-NP-10-AMINE-GAL: To a mix of amine-mercapto hexaethylenglycol linker 6 and alpha-galactose ligand 3 in a ratio 1:1 (0.58 mmol, 3 eq.) in MeOH (49 mL) was added an aqueous solution of gold salt (7.86 mL, 0.19 mmol, 0.025M). The reaction was stirred during 30 seconds and then, an aqueous solution of NaBH4 (1N) was added in several portions (4.32 mL, 4.32 mmol). The reaction was shaken for 100 minutes at 900 rpm. After this time, the suspension was centrifuged 1 minute at 14000 rpm. The supernatant is removed and the precipitated was dissolved in 2 mL of water. Then, 2 mL of the suspension were introduced in two filters (AMICON, 10 KDa, 4 mL) and were centrifuged 5 minutes at 4500 g. The residue in the filter was washed twice more with water. The final residue was dissolved in 80 mL of water.

Figure 11:
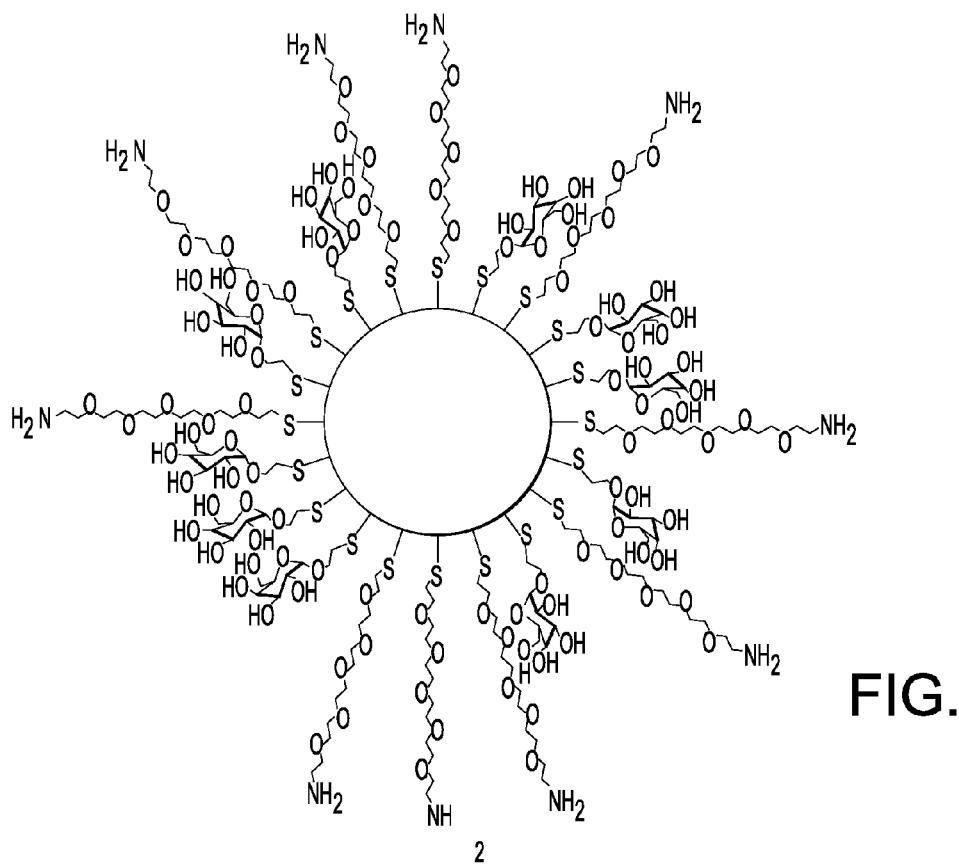
FIG. 11 shows a schematic representation of nanoparticles having a plurality of ligands in the ratio 1:1 of alpha-Gal:EG6NH2 "NP-alpha-Gal (1)EG6NH2(1)". In certain examples, the NP-alpha-Gal(1)EG6NH2(1) nanoparticles are referred to herein as batch NP10.
Figure 12:
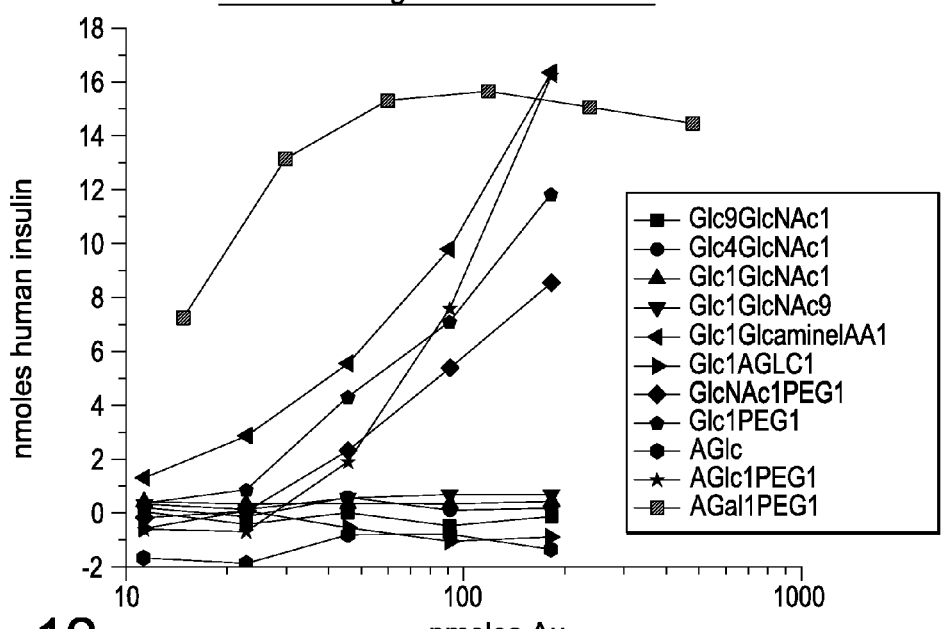
FIG. 12 shows insulin binding curves of human insulin bound (in nmoles) per amount of gold (in nmoles) for 11 different nanoparticle coronal compositions.
Figure 13:
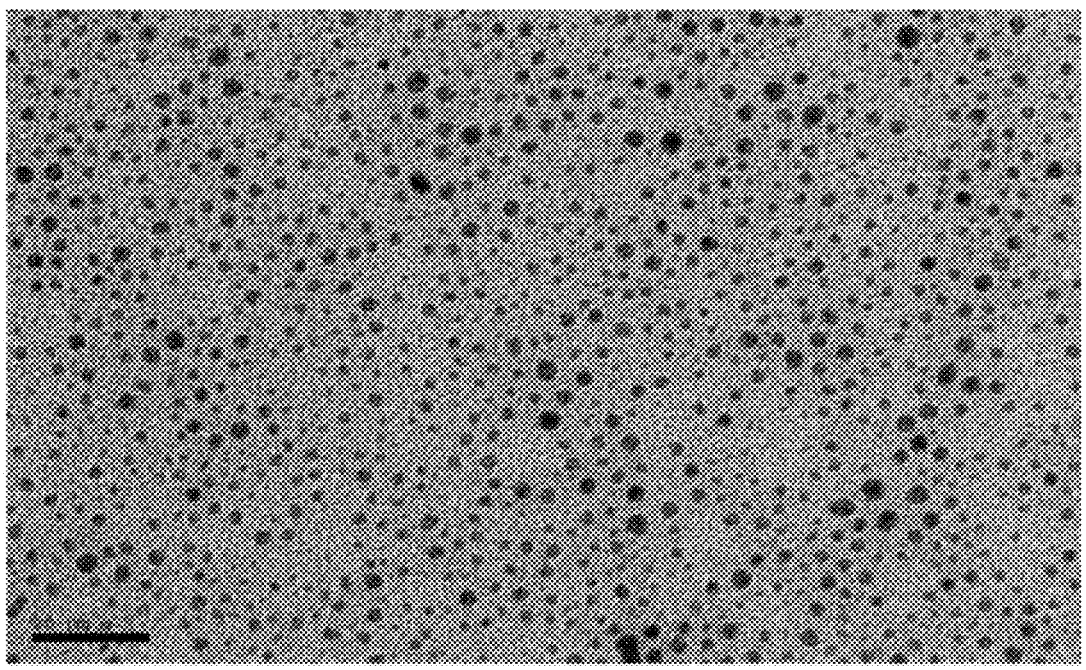
FIG. 13 shows a transmission electron microscopy (TEM) image NP-alpha-Gal (1)EG6NH2(1) nanoparticles {batch #NP10}.
Figure 14A:
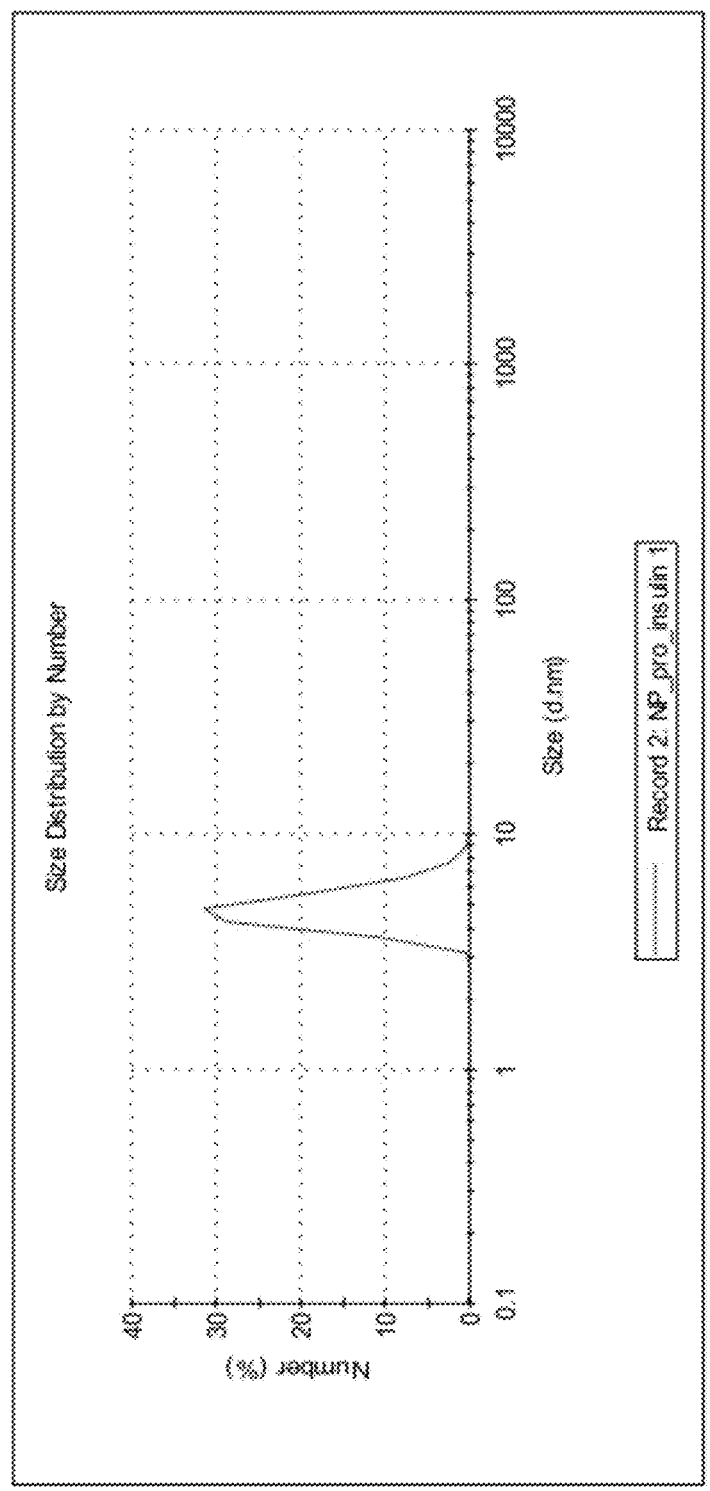
FIG. 14 shows size distribution plots determined by dynamic light scattering (DLS) for MI-NP-10 amine-gal (i.e. NP-alpha-Gal (1)EG6NH2(1) nanoparticles by, A) number and B) volume.
Figure 14B:
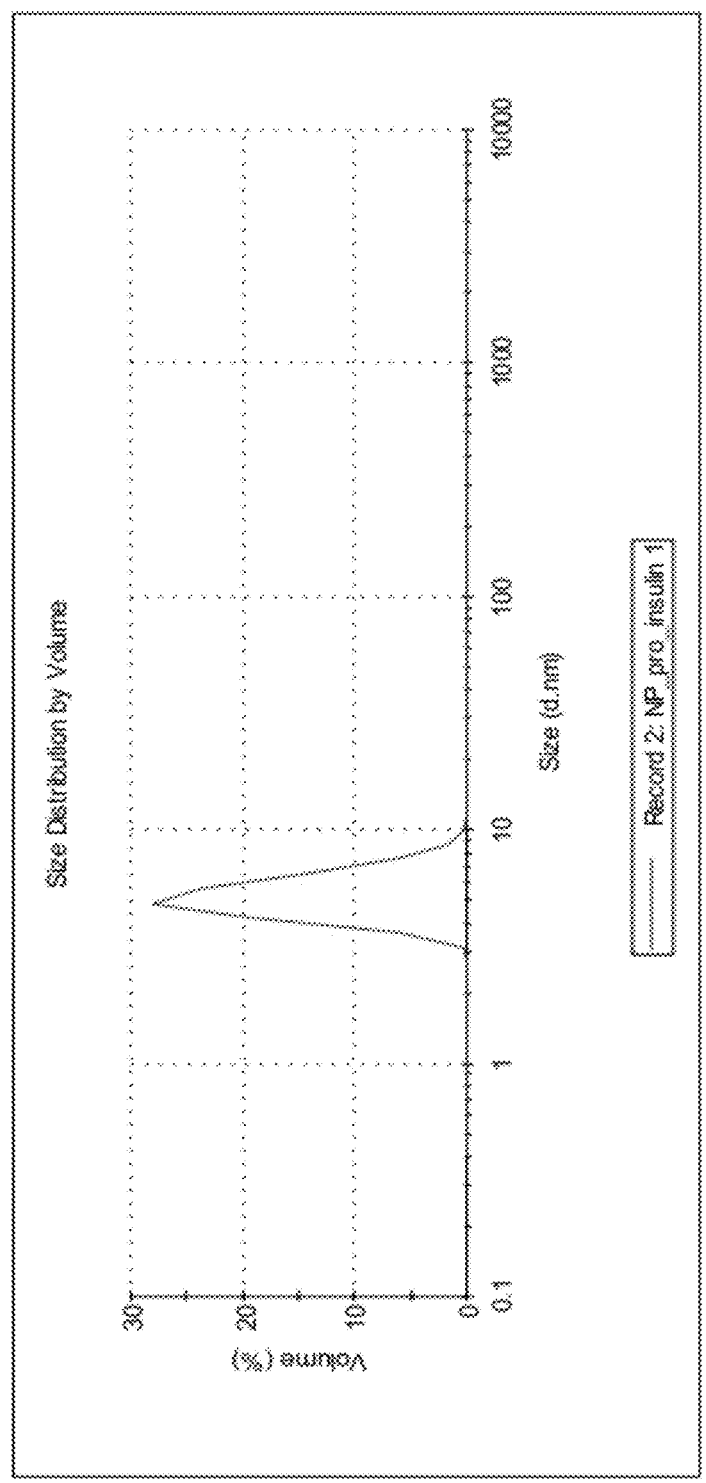

Without wishing to be bound by any theory, a schematic representation of the resulting nanoparticles having a plurality of ligands in the ratio 1:1 of alpha-Gal:EG6NH2 "NP-alpha-Gal (1)EG6NH2(1)" is shown in FIG. 11.

For the preparation of gold NPs manufacture was under laminar flow cabinet. All glass and plastic material (such as eppendorfs, vials and bottles) and solvent (water, HAc) were first sterilized in an autoclave. All other disposables (such as tips and filters) came pre-sterilized.

Example 3

Insulin Binding to Nanoparticles

The following method details how the binding of insulin to alphaGal(1)EG6NH2(1) NPs was performed. The method used fixed insulin and variable NP levels, lower/different levels of NP were used for the other NP samples tested, but with this exception the method was the same for all NPs tested.

Preparation of insulin stock solution; weight 20 mg human insulin into a clean glass vial and add 8.7 ml 10 mM HCl mix gently insulin will dissolve completely, then pH back to 7.5 by adding 1.3 ml 100 mM Tris base, the solution will go cloudy briefly as the insulin passes through its isoelectric point, check the pH is 7.5 and store capped at 4° C., this is the 2 mg/ml insulin stock solution.

Add variable amounts of alphaGal(1)EG6NH2(1) NPs to an eppendorf or suitably sized vessel, for example; 15, 30, 60, 120, 240 and 480 nmoles gold content of NP, make up to a total volume of 200 µl with water, then add 50 µl of human insulin (2 mg/ml in tris HCl pH7.5—see above for preparation of insulin stock solution). Mix gently and leave at room temp for 2 h, follow with a 2 minute bench spin (2000 rpm) to bring down the aggregate. A standard tube which has just 200 µl water and 50 µl insulin should be performed to give the maximum supernatant value, as should a blank i.e. 50 µl Tris HCl pH7.5+200 µl water. If high accuracy is required a sample containing a known amount of alphaGal(1)EG6NH2 (1) NP i.e. 10 µg gold content is made up to 200 µl with water, and 50 µl of the insulin buffer added (Tris HCl pH7.5), this can be used to correct for the slight positive result the alphaGal(1)EG6NH2(1) NP gives in the BCA assay see below*.

Assay the supernatants, 20 µl in triplicate by standard micro BCA assay (Pierce kit 23235), this will give data showing how much insulin remains in supernatant. By subtracting this value from the value for the insulin only standard calculate the amount of NP bound insulin, it can also be expressed as a percent if required. The data obtained here shows the amount of alphaGal(1)EG6NH2(1)-NP that if required to maximally bind the 100 µg of insulin used, these conditions can be scaled up to produce the amount alphaGal(1) EG6NH2 (1)-NP-insulin required.

*The data can be correcting for the slight interference of the free alphaGal(1)EG6NH2(1)-NP in the BCA assay. To do this perform a gold analysis on all the final samples and calculate how much gold remains in the various supernatants, higher levels will be seen in samples with an excess of NP to insulin. Use the BCA value for the 10 μg gold content NP to correct relative to the gold content seen, as demonstrated by the following example:

If the 10 μg gold content NP without insulin gives 0.5 by BCA and 40 μg Au test NP supernatant gives BCA of 1.25, and also shows gold content of 5 μg, that means 0.25 of BCA value (50% of 0.5) is actually due to the free NP, hence corrected value for 40 μg gold test NP supernatant should be 1.00 not 1.25. This is a simplified, illustrative example, the correction factor will be minimal where the gold content in the supernatant is low.

The amount of human insulin bound (in nmoles) per amount of gold (in nmoles) is shown in FIG. 12, wherein:

Glc=2'-thioethyl-β-D-glucopyranoside;

GlcNAc=2'-thioethyl-2-acetamido-2-deoxy-β-D-glucopyranoside;

GlcamineIAA=5'-thiopentanyl-2-deoxy-2-imidazolacetamido-α,β-D-glucopyranoside (alpha, beta mix of isomers);

AGal=2'-thioethyl-α-D-galactopyranoside;

EG6NH2=1-amino-17-mercapto-3,6,9,12,15,-pentaoxa-heptadecanol;

AGlc=2'-thioethyl-α-D-glucopyranoside; and

The numbers in the legend refer to the ligand stiochiometry.

As can be seen by reference to FIG. 12, a relatively high degree of insulin binding was obtained using nanoparticles having a corona of AGal and EG6NH2 in approximately 1:1 ratio. Insulin binding was also exhibited by nanoparticles having any of the following corona compositions:

AGal: EG6NH2 1:1 (Trace 11 FIG. 12)

Glc:GlcamineIAA 1:1 (Trace 10 FIG. 12)

AGlc: EG6NH2 1:1 (Trace 8 FIG. 12)

BGlc: EG6NH2 1:1 (Trace 6 FIG. 12)

GlcNAc: EG6NH2 1:1 (Trace 7 FIG. 12).

The insulin bound to nanoparticles as described herein was found to be releasable upon contact with a physiological solution (e.g. a saline solution) and was found to be detectable such that a positive result was achieved in an ELISA for (human) insulin. These results indicate that insulin-bound nanoparticles of the invention provide insulin in a form that is available for interaction with biological systems and/or components. Thus, the nanoparticles are capable of acting as a carrier/stabiliser of insulin (e.g. for storage and/or processing for incorporation into, e.g., a pharmaceutical product) whilst also maintaining the ability to present or make available insulin (for example, monomeric insulin) to exert its biological effects, for example following delivery to a subject, organ or cell thereof.

Example 4

Characterisation of Nanoparticles

I) Characterization of Insulin Gold Nanoparticles Batch MI-NP-10-Ins (NP-alpha-Gal(1)EG6NH2(1))

a) Gold Content:

The gold content was determined using a method based on the formation of a coloured complex between ethopropazine and the gold after complete oxidation to Au(III). The absorbance of the sample is measured at 513 nm and quantitatively compared to similar solutions having a known amount of gold.

The gold content was determined to be (batch #NP10): 262.5±56.3 mg/L.

TEM:

a transmission electron microscopy (TEM) image of the nanoparticle suspension is shown in FIG. 13.

The sample was determined to have the following size characteristics for the gold core:

Count=783

Mean (diameter)=2.323 nm±0.716 nm

Min.=1.002 nm

Max.=4.859 nm

Mode=2.104 nm d) Size distribution by Dynamic Light Scattering: number and volume distributions were determined by dynamic light scattering (DLS) for MI-NP-10 amine-gal (i.e. NP-alpha-Gal (1)EG6NH2(1) nanoparticles), and are shown in FIGS. 14 A and B, respectively.

The peak value for the peak shown in FIG. 14A is as follows:

Peak 1 4.875 nm

The peak value for the peak shown in FIG. 14B is as follows:

Peak 1 5.289 nm

III) Final preparation of insulin gold nanoparticles Batch MI-NP-10-INS.

A solution of gold nanoparticles MI-NP-10 (13.041 mg gold) was made up to 49.68 mL of water. To the final solution was added acetic acid to obtain a pH=4.6. Then, 55.7 mg of human insulin in 27.85 mL of Tris.HCl pH 7.5 was added. The suspension was left 24 hours and after this time, was centrifuged 1 minute at 4500 g. The supernatant was removed and stored for further insulin and gold content analysis. The precipitate was resuspended in 3.220 mL of water to get a final insulin concentration of 500 units insulin/mL. The size distribution of the insulin-gold nanoparticles was determined by DLS analysis. The insulin content was determined by BCA standard assay.

** The final preparation of insulin gold NP was manufactured under laminar flow cabinet. All glass and plastic material (such as eppendorfs and bottles) and solvent (such as water, TrisHCl and HAc) used were sterilized in an autoclave. All other disposables (such as tips and filters) came pre-sterilized.

Characterisation:

a) Size distribution by Dynamic Light Scattering is shown by number and volume in FIG. 15 A, and B, respectively for MI-NP-10-INS (amine-gal-INSULIN nanoparticles).

The peak value for the peak shown in FIG. 15A is as follows:

Peak 1 68.46 nm

Figure 15B:
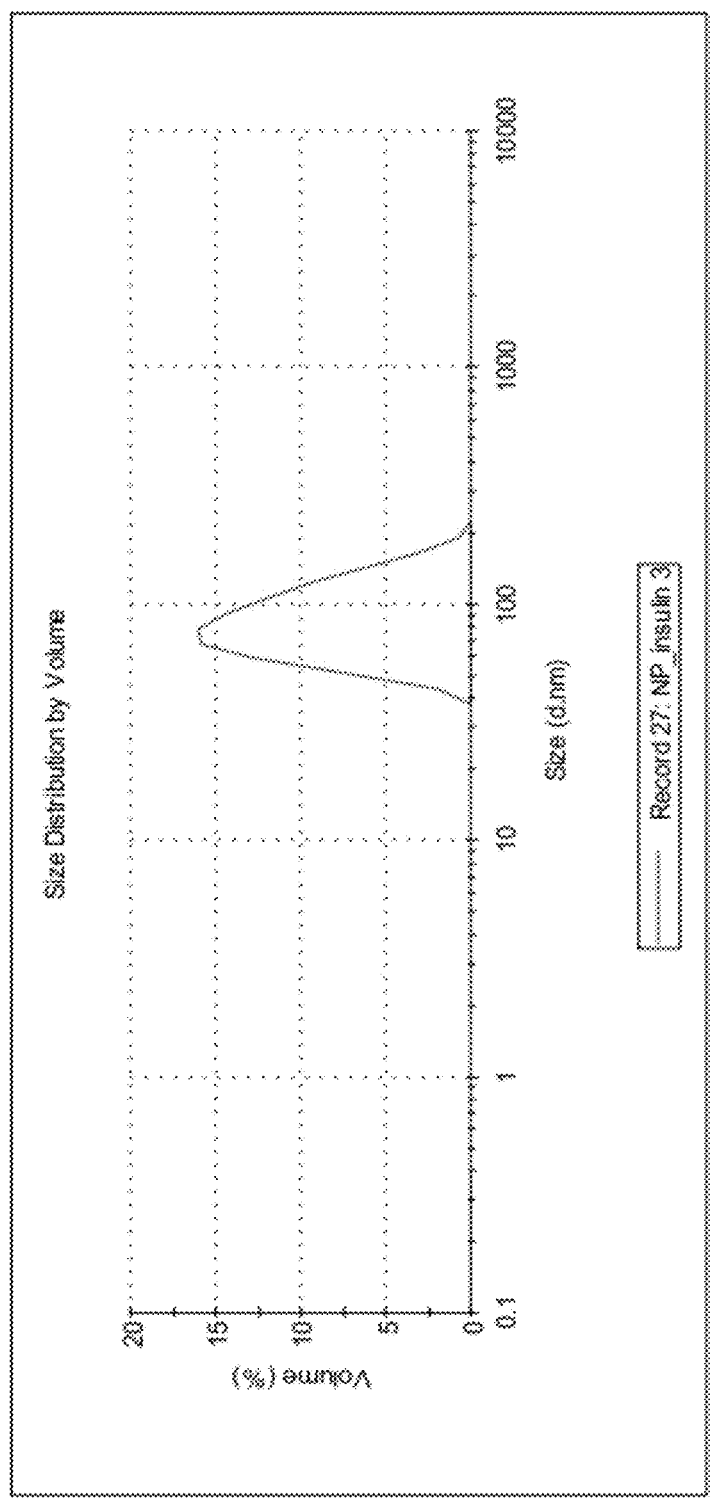
FIG. 15 shows size distribution plots determined by dynamic light scattering (DLS) for insulin bound-MI-NP-10 amine-gal (i.e. NP-alpha-Gal (1)EG6NH2(1) nanoparticles) by A) number and B) volume.

The peak value for the peak shown in FIG. 15B is as follows:

Peak 1 88.38 nm b) Insulin Content:

The % of insulin binding to the nanoparticles was determined by the following formula:

$$\% \text{ insulin} = \frac{\text{insulin added} - \text{insulin supernatant}}{\text{insulin added}} \times 100$$

TABLE 2

| | Insulin content | | | |
|---|---|---|---|---|
| Sample | Insulin added (mg) | Insulin supernatant (mg) | Insulin bound (mg) | % insulin bound |
| MI-NP-10 insulin | 55.700 | 1.308 | 54.4 | 97.65 |

Concentration of Insulin and Gold in NP-Insulin Nanoparticles:

Insulin: 55.7 mg Insulin
Gold: 13.041 mg of gold
Total volume: 3.23 mL water
Final insulin concentration: 17.25 mg insulin/mL=500 units/mL
Final gold concentration: 4.037 mg Au/mL.

Without wishing to be bound by any theory, the present inventors consider the following:

102 Au atoms/NP, for which the mathematical result is 14 insulin molecules attached to 1 NP. Since geometrical considerations allow space for about 7 insulin molecules on the surface of the nanoparticle, these results suggest that each NP contains 7 insulin dimer units.

Further characterisation of the insulin gold nanoparticles Batch MI-NP-10-INS yielded the following results.

Final insulin concentration: 17.25 mg insulin/mL=500 U/mL, determined by colorimetric bicinchonicic acid assay after calibration against insulin standardized solutions of known concentrations.

Final gold concentration: 4.037 mg Au/mL, determined by colorimetric assay with ethopropazine assay after calibration against gold standardized solutions of known concentrations.

Total volume: 3.23 mL in MilliQ water.

After geometrical considerations, one α-galactose-EG-amine-Au nanoparticle contains a gold core with 102 atoms. Then:

4.037 mg=2.049e-5 moles=1.234e19 atoms=1.21e17 nanoparticles 17.25 mg=2.97e-6 moles=1.789e18 molecules Therefore one α-galactose-EG6NH2-Au nanoparticle is bound to about between 14 and 15 insulin molecules to produce the final nanoparticle.

Results from Thermogravimetric Analysis:

Without wishing to be bound by any theory, the present inventors consider that for insulin-NP we have 500 ug of dry weight in which 410 ug is decomposed. Therefore the percent organic is 82%. Considering 102 atoms of gold in one α-galactose-EG6NH2-Au nanoparticle, gold weight would be 20091 (18%) and an organic corona 12122. Therefore to have a particle that is 82% organic it must have weight of 111616 that is 91525 organic. Since 12122 of organic is corona that leaves about 79403 of the organic as insulin. Since insulin has MW 5808 then we must have 14 moles insulin per particle.

Figure 16:
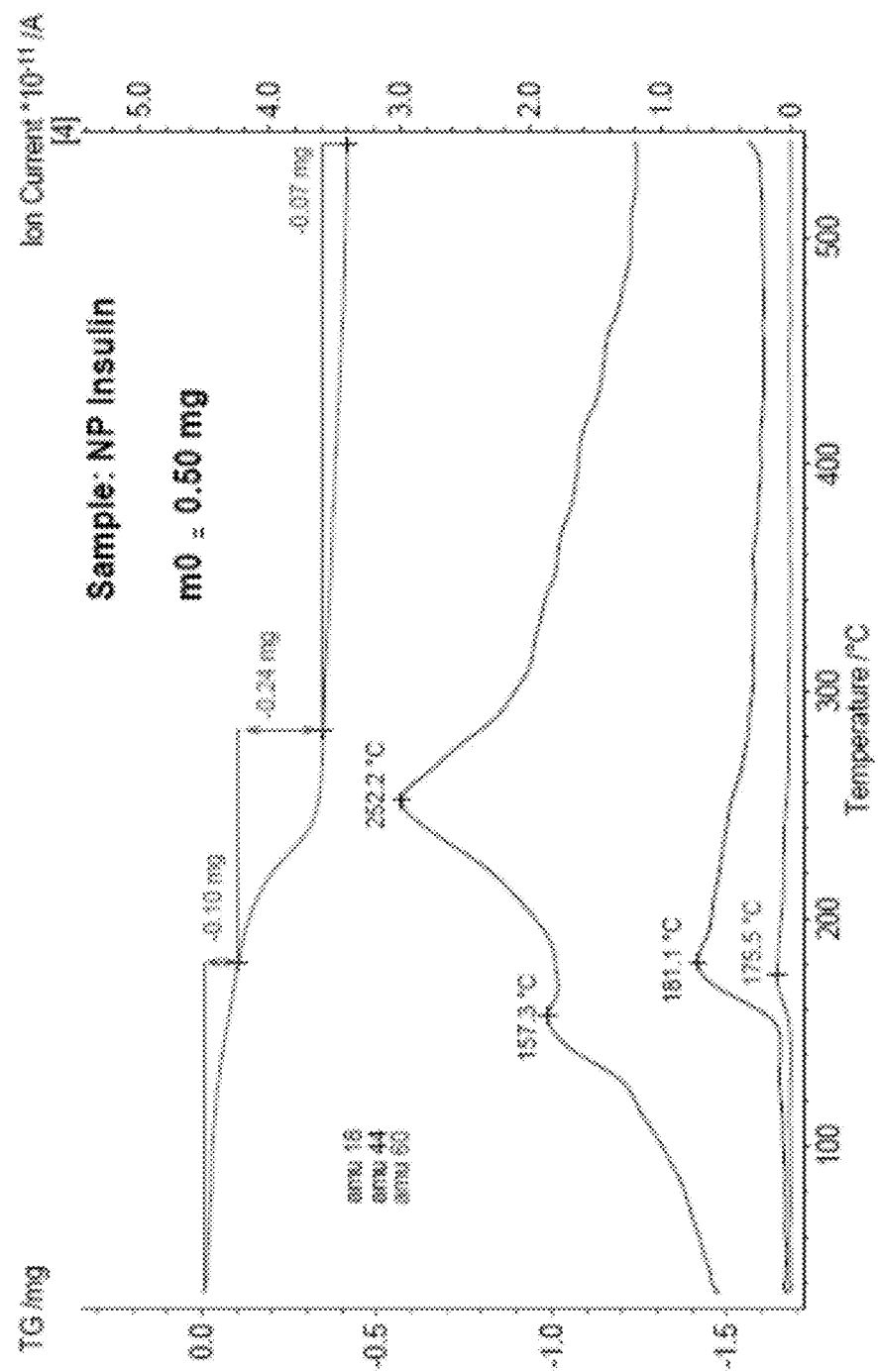
FIG. 16 shows experimental thermogravimetric analysis (TGA) data for α-galactose-EG-amine-Au nanoparticles with temperature peaks indicated {batch #NP10}.

FIG. 16 shows the experimental thermogravimetric analysis (TGA) data.

Example 5

Zn Optimisation of Insulin Binding

Gold nanoparticles (NPs), alphaGal(1)EG6NH2(1) NPs, were prepared as described in Example 2 above. In order to evaluate the influence of Zn on insulin binding to the NPs, a first batch of NPs was synthesised in the absence of Zn. A second batch of NPs was synthesised in the presence of 1.33 equivalents of Zn. A third batch of NPs was synthesised in the absence of Zn, but had 1.33 equivalents of $ZnCl_2$ added to the NPs post-synthesis. The binding of human insulin to the three batches of gold NPs was then measured.

Figure 17:
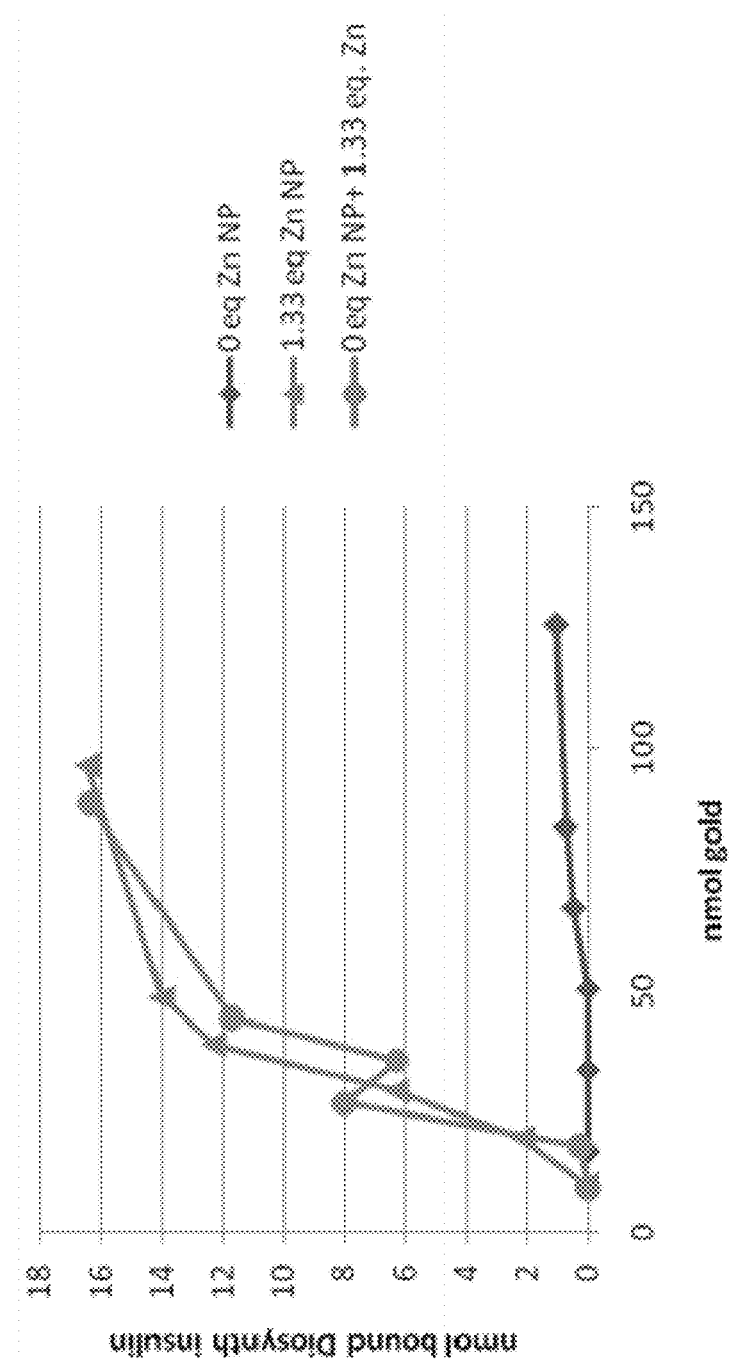
FIG. 17 shows a graph of insulin bound to gold nanoparticles, wherein diamonds indicate nanoparticles in the absence of zinc, triangles indicate nanoparticles synthesized in the presence of 1.33 equivalents of zinc, and circles indicate nanoparticles synthesized in the absence of zinc to which 1.33 equivalents of zinc have been added post-synthesis.

The results are shown in FIG. 17. FIG. 17 displays a Graph showing the amount of fixed 17.2 nmoles of Insulin binding to varying gold NP concentrations. Comparison of NP synthesised without Zn, a NP with synthesised with 1.33 eq, and Zn free NPs with 1.33 eq of ZnCl2.

The graph in FIG. 17 shows that with no zinc present insulin binding is at a very low level. When zinc is present insulin binding is significantly higher up to quantitative. Equivalent insulin binding occurs whether the zinc is present during NP synthesis or whether it is added post synthesis.

Without wishing to be bound by any theory, the present inventors believe that the $Zn^{2+}$ cation provides improved insulin binding to the gold NPs. Other forms of Zn, such as ZnO may also mediate improved insulin binding. In particular, presence of ZnO in gold NP sample that had been stored for a period of months indicates that ZnO can form and may additionally or alternatively to $Zn^{2+}$ cation mediate or facilitate improved insulin binding to the NPs.

The importance of $Zn^{2+}$ in insulin crystallisation, form and function has been reported previously. However, data described herein indicate that insulin bound to NPs, including in the presence of $Zn^{2+}$, is in monomeric or dimeric form rather than the hexameric form more commonly associated with human insulin in the presence of $Zn^{2+}$ (i.e. insulin not bound to NPs). This may present a considerable advantage in relation to the present invention because monomeric or dimeric insulin is preferred in many settings (e.g. clinical settings) as compared with hexameric insulin.

The present inventors have found that binding of GLP-1 to gold NPs (described herein) takes place the presence of Zn (including, but not limited to $Zn^{2+}$ and/or ZnO). GLP-1 binding to gold NPs described herein was to NPs synthesised in the presence of Zn. It is specifically contemplated herein that Zn may be present in GLP-1-bound gold nanoparticle compositions.

Example 6

GLP-1 Binding to Gold Nanoparticles

Figure 18:
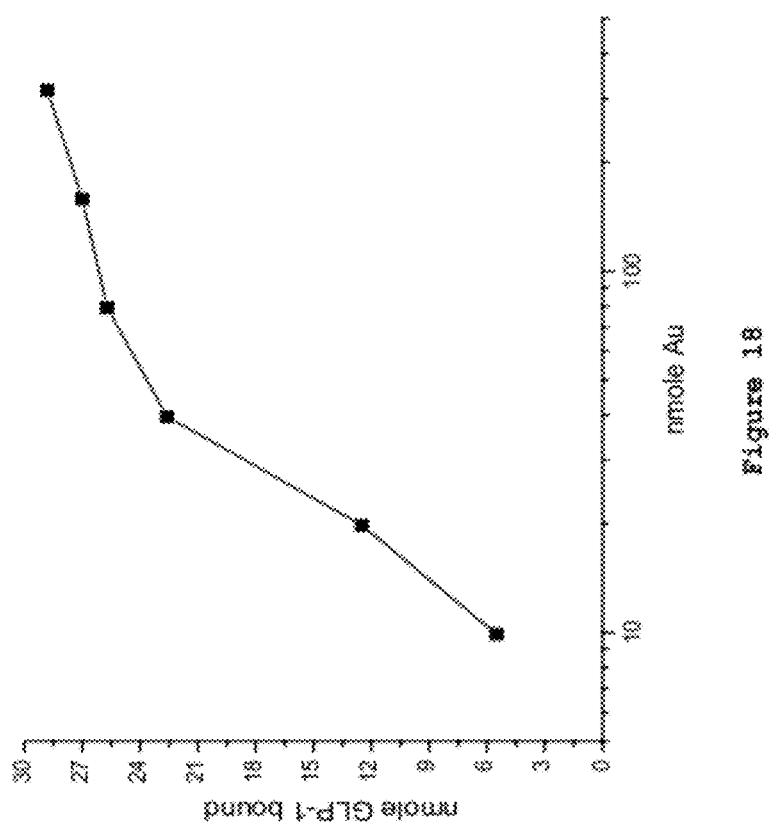
FIG. 18 shows binding of GLP-1 to gold nanoparticles at varying amounts of gold nanoparticles.

Gold nanoparticles (NPs), alphaGal(1)EG6NH2(1) NPs, were prepared as described in Example 2 above. Rather than adding insulin, GLP-1 was added. It was found that GLP-1 binds to the NPs. The binding of a fixed 29.8 nmoles of GLP-1 to varying gold NP concentrations is shown in FIG. 18. These results demonstrate that a peptide other than insulin binds to the nanoparticles of the invention.

Example 7

Figure 19:
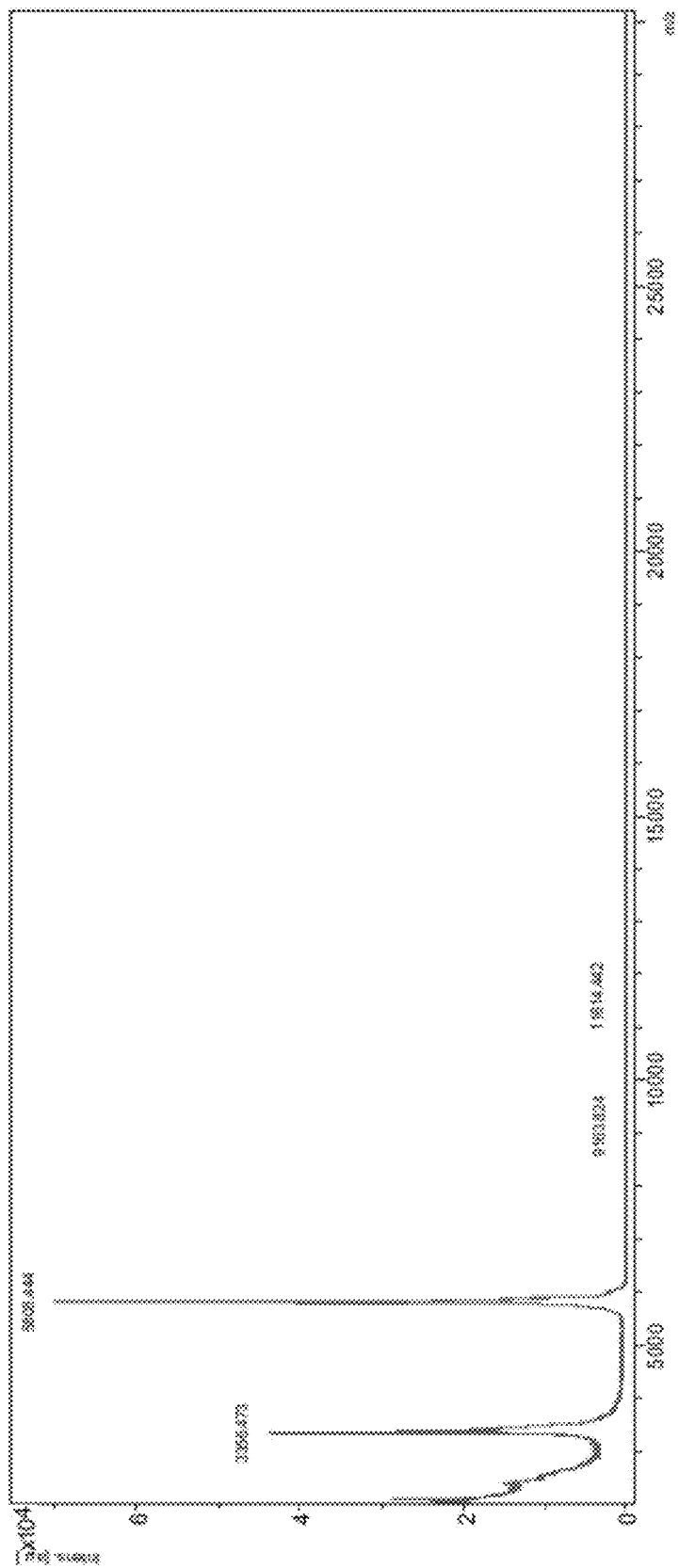
FIG. 19 shows a MALDI trace showing GLP-1 and insulin from a nanoparticle preparation comprising both GLP-1 and insulin.
Figure 20:
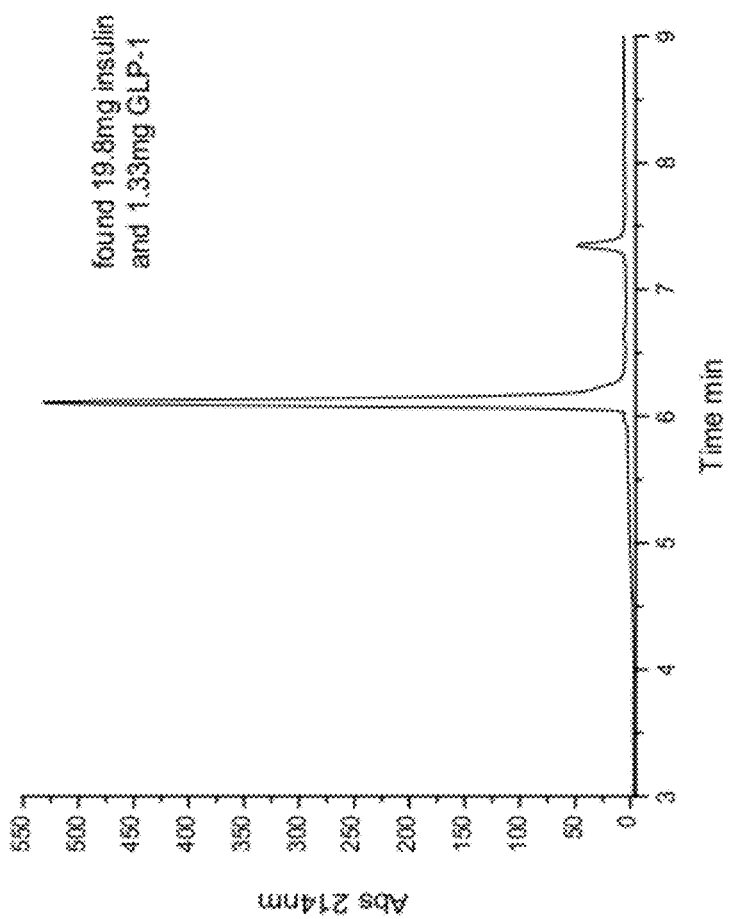
FIG. 20 shows an HPLC trace showing GLP-1 and insulin from a nanoparticle preparation comprising both GLP-1 and insulin.

Nanoparticles Co-Binding More than One Protein: Combination Insulin/GLP-1 Nanoparticles Gold nanoparticles (NPs), alphaGal(1)EG6NH2(1) NPs, were prepared as described in Example 2 above. Insulin and GLP-1 were both added to the NPs. An aqueous solution of the GLP-1/Insulin NPs was subjected to analysis by MALDI and the results are shown in FIG. 19. The GLP-1/Insulin NPs were subjected to HPLC and the trace is shown in FIG. 20. The HPLC data show that 19.8 mg of insulin was measured and 1.33 mg of GLP-1.

The binding reaction was performed using a 1:1 molar ratio of insulin and GLP-1. The HPLC data show that the approximate ratio of insulin:GLP-1 was 9:1 indicating preferential binding of the insulin relative to GLP-1 to the nanoparticle coronal surface.

The MALDI and HPLC data demonstrate the mixed binding of GLP-1 and Insulin to gold nanoparticles. Without wishing to be bound by any theory, the present inventors believe that co-binding of two or more different species of peptide to the nanoparticle of the invention may be preferred in certain settings (e.g. certain clinical settings) as compared with binding of a single species of peptide. In particular, combinations of peptides may be carried on a nanoparticle such that the peptides perform mutually beneficial functions and/or act in concert, such as in a synergistic fashion.

Example 8

In Vivo Treatment of Minipigs with Insulin-Carrying Nanoparticles, GLP-1-Carrying Nanoparticles, Mixtures Thereof and Combination Insulin/GLP-1 Nanoparticles In order to explore further the monomeric release characteristics of NP-insulin, constructs of insulin and GLP-1 were synthesized. We have proposed that GLP-1 is immediately removed from the plasma via receptors (rather than enzymatic degradation) and that the pharmacodynamics (PD) effect of GLP-1 will, like insulin, be temporally and quantitatively unrelated to the pharmacokinetics (PK), which is thought to be just minutes. We have previously used NP-insulin to provide a source of monomer insulin for receptor blockade ten minutes before IVG stimulated release of endogenous monomeric insulin. The PK of endogenous insulin through the 1st phase and 2nd phase was then visualized. We have also used Novo Rapid entrainment to block insulin receptors and measure the PK of NP-insulin. In this study we have used the co-administration of NP-GLP-1 along with the administration of NP-insulin to provide a pancreatic insulinotropic effect and to the reduce the clearance rate of both endogenously released insulin and exogenous NP-insulin in response to IVG. The PK of both the endogenous released and exogenous NP-insulin were measured.

Figure 21:
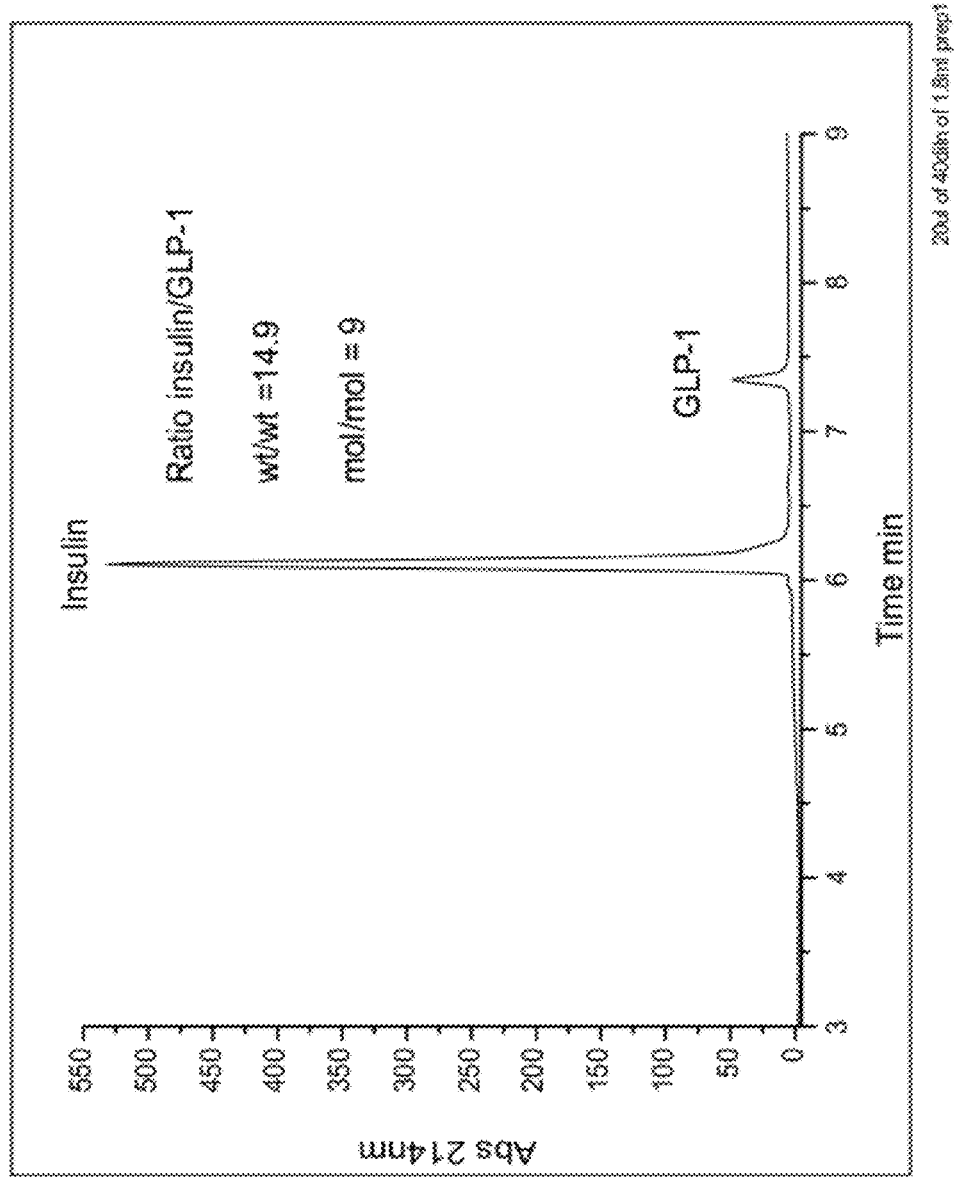
FIG. 21 shows an HPLC trace showing GLP-1 and insulin from a nanoparticle preparation comprising both GLP-1 and insulin, in which the ratio of insulin to GLP-1, in both wt/wt and mol/mol terms, is indicated.

The PK and PD of NP-insulin, a combination nanoparticle having both insulin and GLP-1 loaded on the same nanoparticle (NP-insulin/GLP-1—see Example 7 for details of preparation) and a mixture preparation of NP-insulin and NP-GLP-1 were assessed using healthy female minipigs. Surface analysis showed that single NP-insulin particles have ~16 moles insulin/particle and NP-insulin/GLP-1 particles have ~26 moles insulin/particle. Analysis of the NP-insulin/GLP-1 nanoparticles as shown in FIG. 21 revealed a molar ratio of insulin to GLP-1 on the same particle was 9/1. The administered dose of insulin was 2.5 U/animal and the dose of GLP-1 was 0.1 nmol/kg (average wt. 19 kg) either using a single particle or mixing NP-insulin particles and NP-GLP-1 particles to give a molar ratio of 9/1 for insulin/GLP-1. This stoichiometry provides the opportunity to deliver a therapeutic dose of both insulin and GLP-1 on a single particle.

Animals were fasted overnight and then placed under anaesthesia. After 120 minutes a subcutaneous (s.c.) injection of the test items was administered in water vehicle and 10 minutes later an intraveneous glucose (IVG) challenge of 0.33 gm/kg was administered intravenous. Blood was sampled at intervals and measurements of insulin, glucose, C-peptide and glucagon recorded. The IVG was required since exogenously administered GLP-1 only stimulates pancreatic insulintropic actions in the presence of hyperglycaemia. Further, IVG doesn't result in endogenous release of GLP-1 from intestinal L cells since a plasma/portal glucose differential which is required for endogenous release, is not present after systemic administration of glucose. This contrasts with an oral glucose test which will induce endogenous GLP-1. GLP-1 has also been shown to increase plasma insulin levels by decreasing the catabolic rate of plasma insulin. For hormones with short half-lives this can have a rapid and significant effect on plasma levels. Direct insulinotropic effects have also been proposed based on studies with isolated pancreatic islets but the mechanism in vivo has not been definitively established. Extrapancreatic effects of exogenous GLP-1 will be present in either oral glucose test (OGT) or IVG protocols. Reduction in blood glucose levels after oral glucose tolerance tests has been proposed to be secondary to reduced gastric emptying but this action of GLP-1 has recently been challenged and nausea may be implicated in the effect. Clarification of the mechanism of action of exogenous administered native GLP-1 can not necessarily be extrapolated from studies on the exendin analogues or GLP-1 protease inhibitors. In the present experimental protocol the test items were given prior to the glucose challenge and therefore models a potential pharmacodynamics (PD) effect on a subsequent glucose load—i.e. pre-meal treatment of diabetics.

Figure 22:
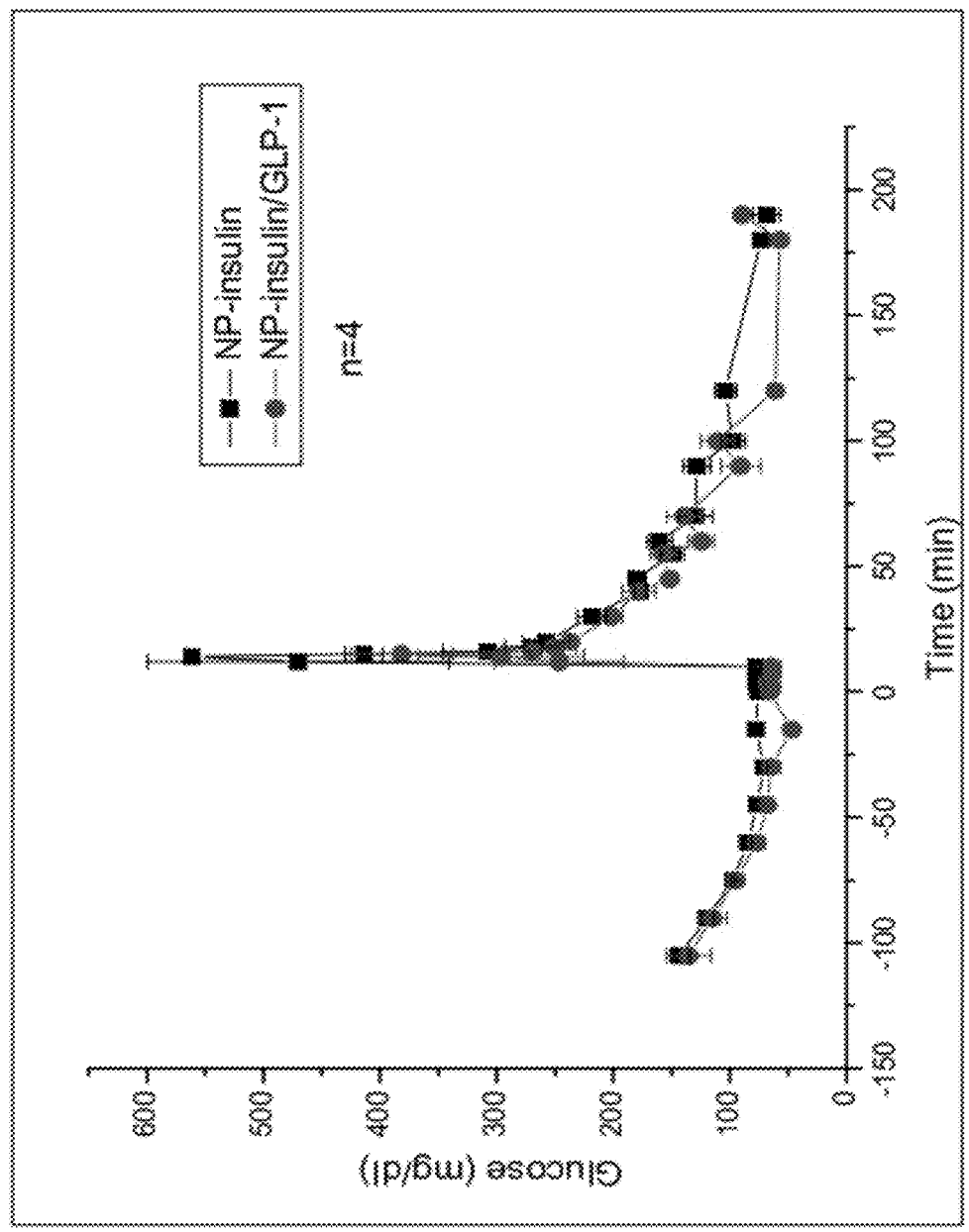
FIG. 22 shows the pharmacodynamics of glucose clearance for both a nanoparticle-insulin preparation and a nanoparticle-insulin/GLP-1 combination preparation.

FIG. 22 shows the PD of glucose clearance for the NP-insulin and NP-insulin/GLP-1 particles. The data demonstrate that the magnitude of the glucose $C_{max}$ was reduced by almost 50% for the combination NP-insulin/GLP-1 as compared with treatment using the NP-insulin preparation. The blunting of the $C_{max}$ is a characteristic of cephalic phase insulin release and may indicate an increase in volume of distribution (Vd). GLP-1 is known to reduce AV glucose differences and this effect may therefore promote glucose entering interstitial space more efficiently where the target organs of muscle and liver (space of Disse) can dispose of the glucose. PET scans of FDG in normal and diabetic patients after insulin injection has demonstrated liver and muscle to be the main target organs with abnormal enhanced accumulation in muscle in diabetics, in contrast in normal individuals almost all the glucose is removed by the liver. The ability of NP-insulin/GLP-1 to reduce the magnitude of the glucose $C_{max}$ in response to a glucose challenge indicates that the "glucose excursion" is relatively normalised compared with the large glucose excursion that is typically exhibited by diabetic patients in response to a glucose challenge. This indicates that the NP-insulin/GLP-1 addresses a key feature of the diabetic condition: the regulation of the glucose excursion in response to a glucose challenge (see Bagger et al., 2011, J. Clin. Endocrinol. Metab., Vol. 96 (3), pp. 737-745, the entire contents of which are expressly incorporated herein by reference). This is expected to be of therapeutic benefit. The inventors presently believe that NP-insulin/GLP-1 may advantageously regulate the "incretin effect" such that the glucose excursion in a treated diabetic following a glucose challenge is reduced to, or close to the normal, non-diabetic, range of around 2 times baseline blood glucose concentration.

Figure 23:
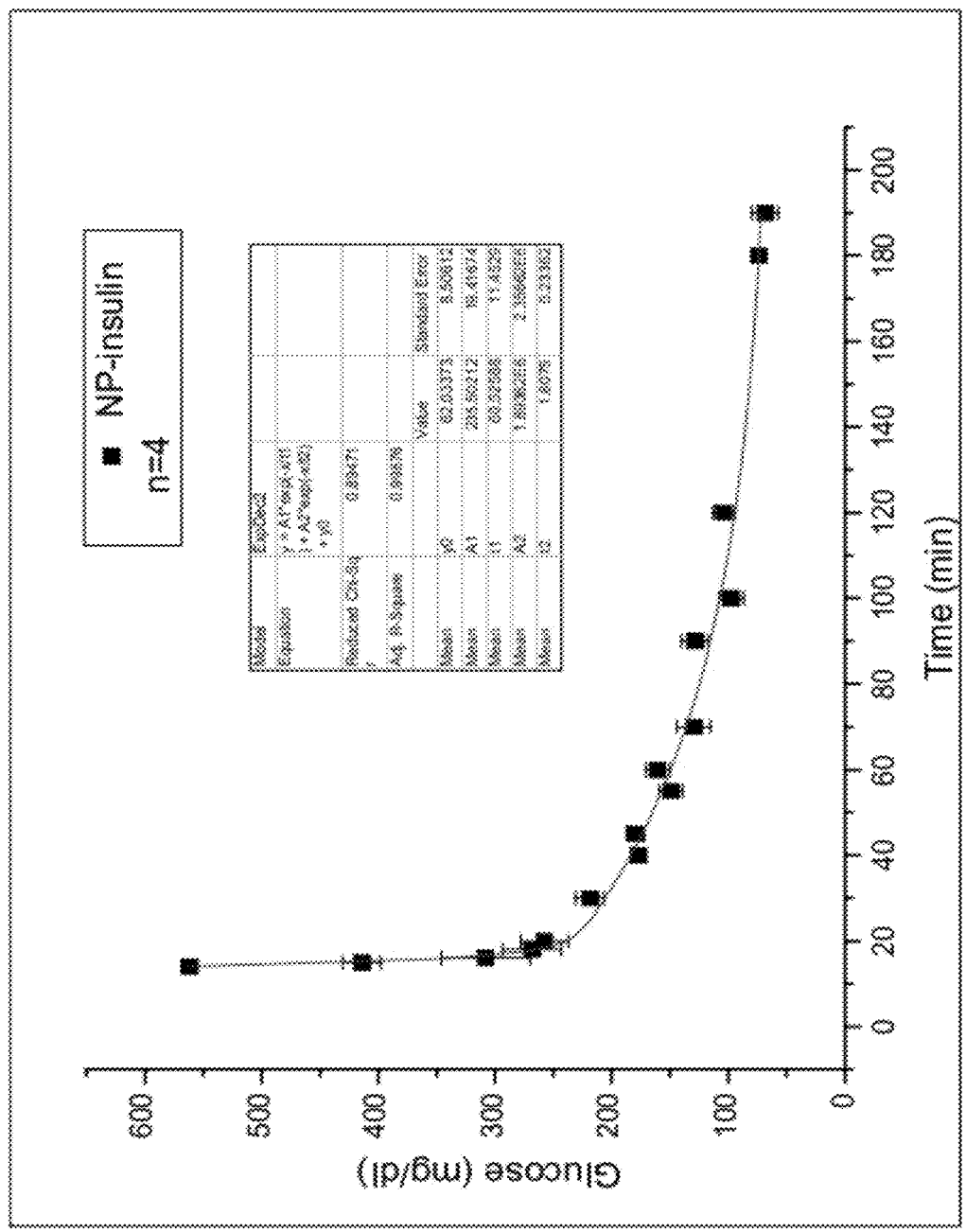
FIG. 23 shows a plot of glucose clearance from one minute after a five minute square wave intravenous infusion of glucose for a nanoparticle-insulin preparation.
Figure 24:
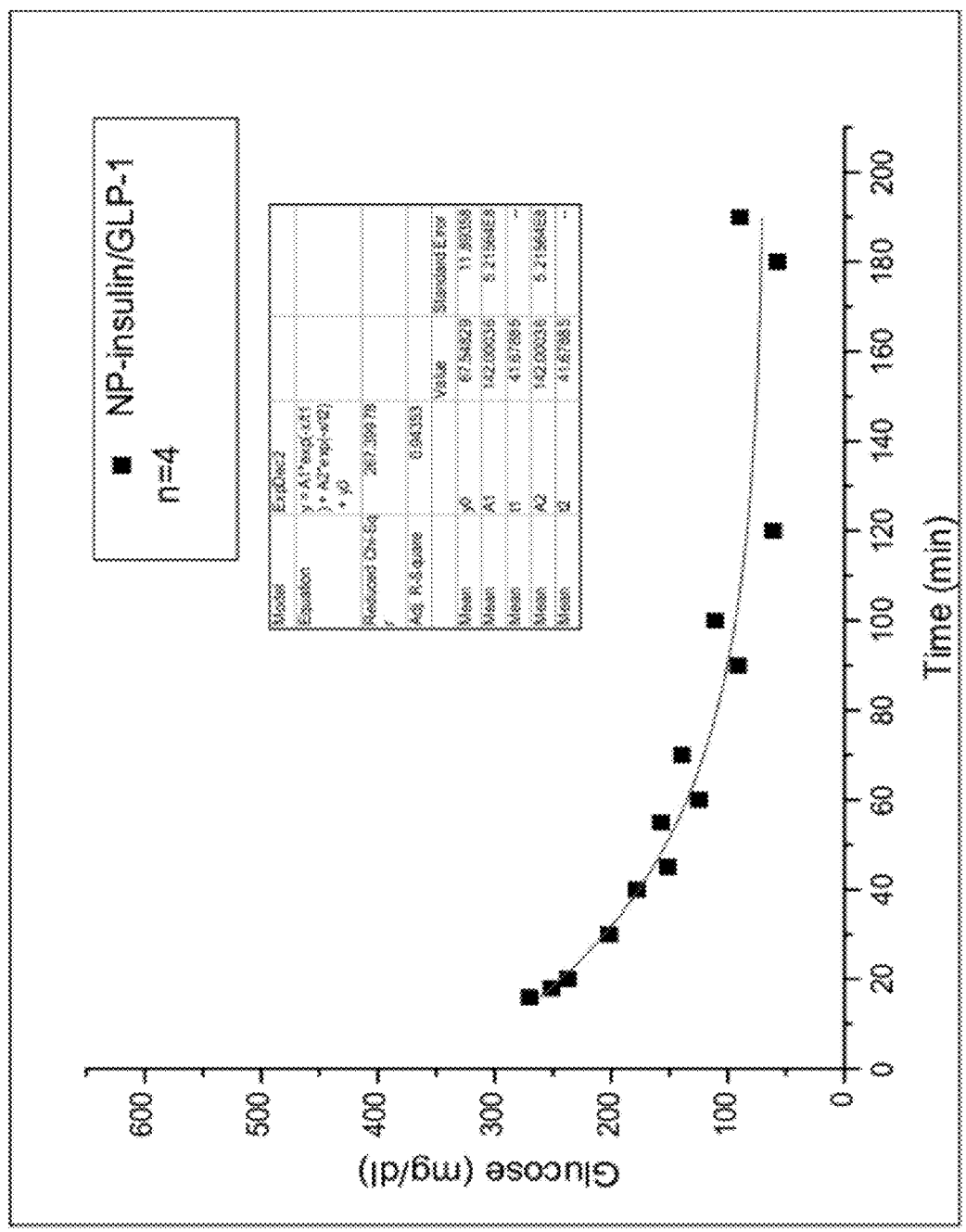
FIG. 24 shows a plot of glucose clearance from one minute after a five minute square wave intravenous infusion of glucose for a nanoparticle-insulin/GLP-1 combination preparation.

FIGS. 23 and 24 show the data plotted from 6 minutes after IVG (1 minute after the end of the 5 minute square wave infusion). The pre-treatment with the NP-insulin had a dramatic effect on the initial clearance of the glucose (vascular compartment 1) with a half-life of 1.1 min. The second clearance half-life was 42 min for the interstitial space elimination (compartment 2). The presence of GLP-1 on the same particle had the effect of dramatically damping the $C_{max}$ (glucose excursion) and the two compartment model could not be used and the data could only be fit to a single exponential giving a calculated half-life of 28 min.

Figure 25:
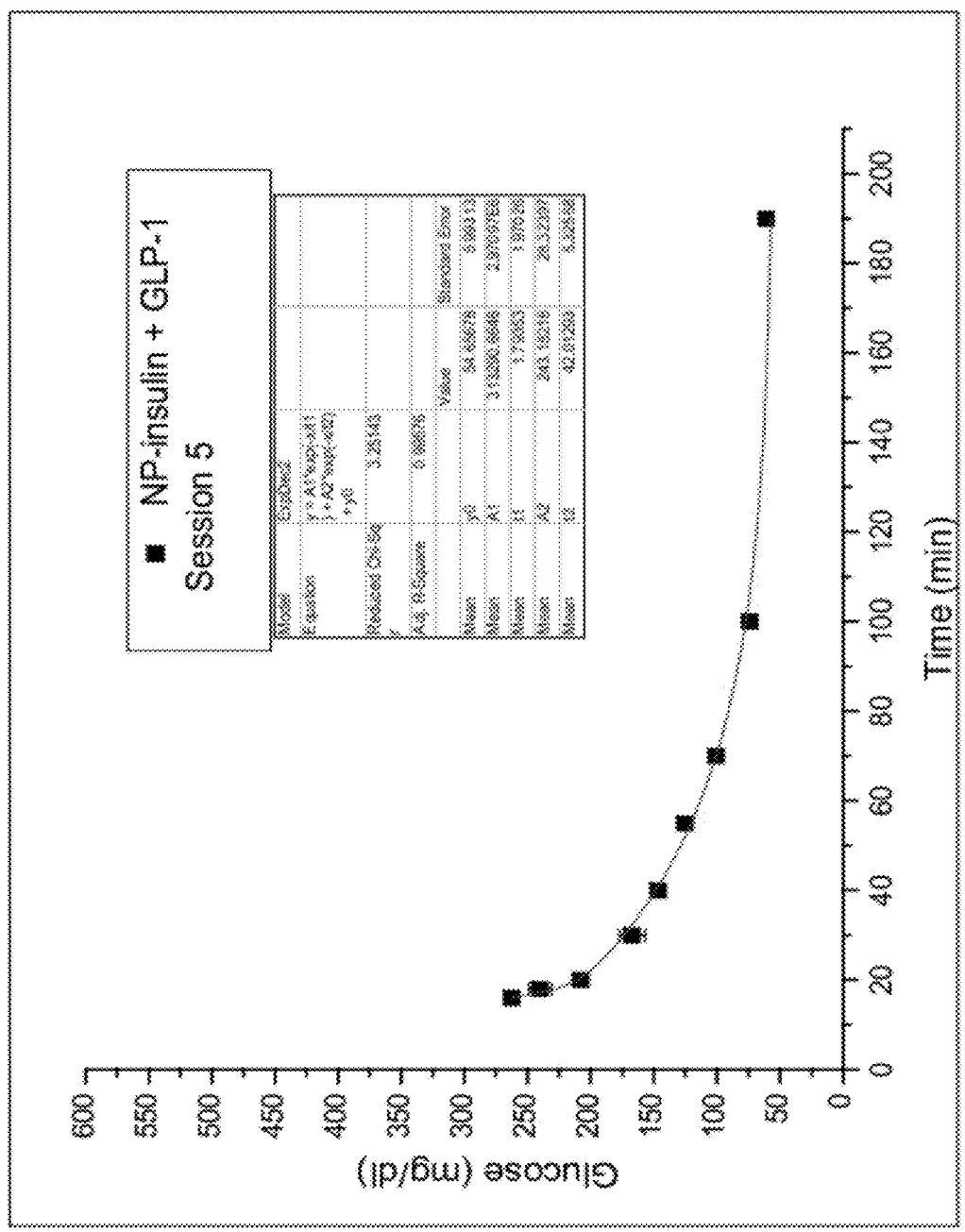
FIG. 25 shows a plot of glucose clearance for a mixture of a nanoparticle-insulin preparation and a nanoparticle-GLP-1 preparation.
Figure 26:
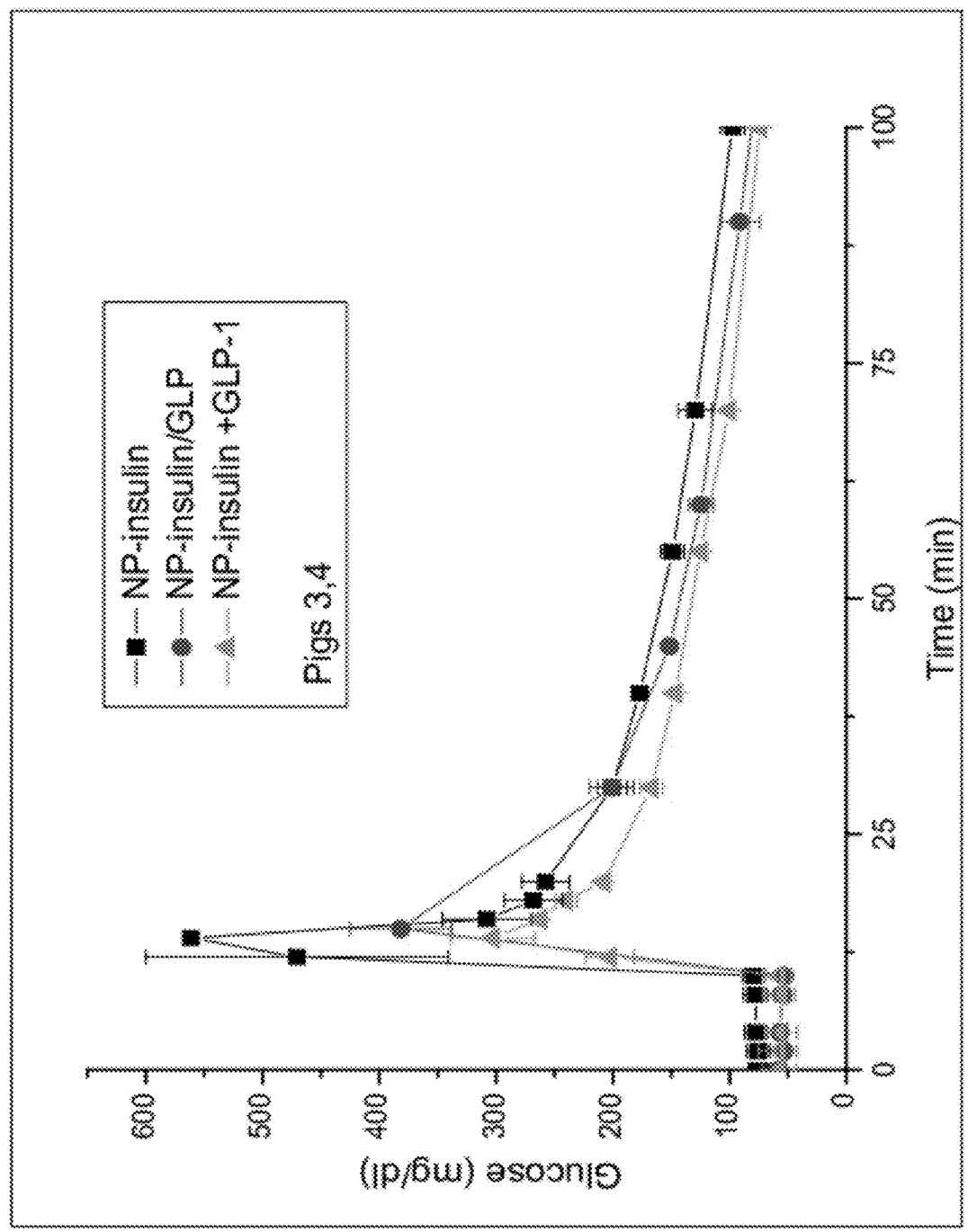
FIG. 26 shows a plot of glucose clearance for three test items: an NP-insulin preparation (squares); an NP-insulin/GLP-1 combination preparation (circles); and an NP-insulin and NP-GLP-1 mixture (triangles)

FIG. 25 shows the PD data for mixing two particles containing insulin or GLP-1 (that is the insulin and GLP-1 were on separate particles). Again a significant damping of the $C_{max}$ is observed and the majority of the glucose is cleared with a half-life of −29 min which was similar to the particle containing both insulin and GLP-1. FIG. 26 compares the three test items in the same pigs. Both GLP-1 containing test items dampened the $C_{max}$ of the glucose square-wave infusion, confirming this unique PD effect of the GLP-1. Reduction of glucose excursion is critical in the treatment of type II diabetes and as far as we are aware this has not previously been reported for free GLP-1 or the acylated analogues. GLP-1 has recently been shown to reduce water intake and if the effects we observe are due to $V_d$ redistribution these two observation could be linked.

Figure 27:
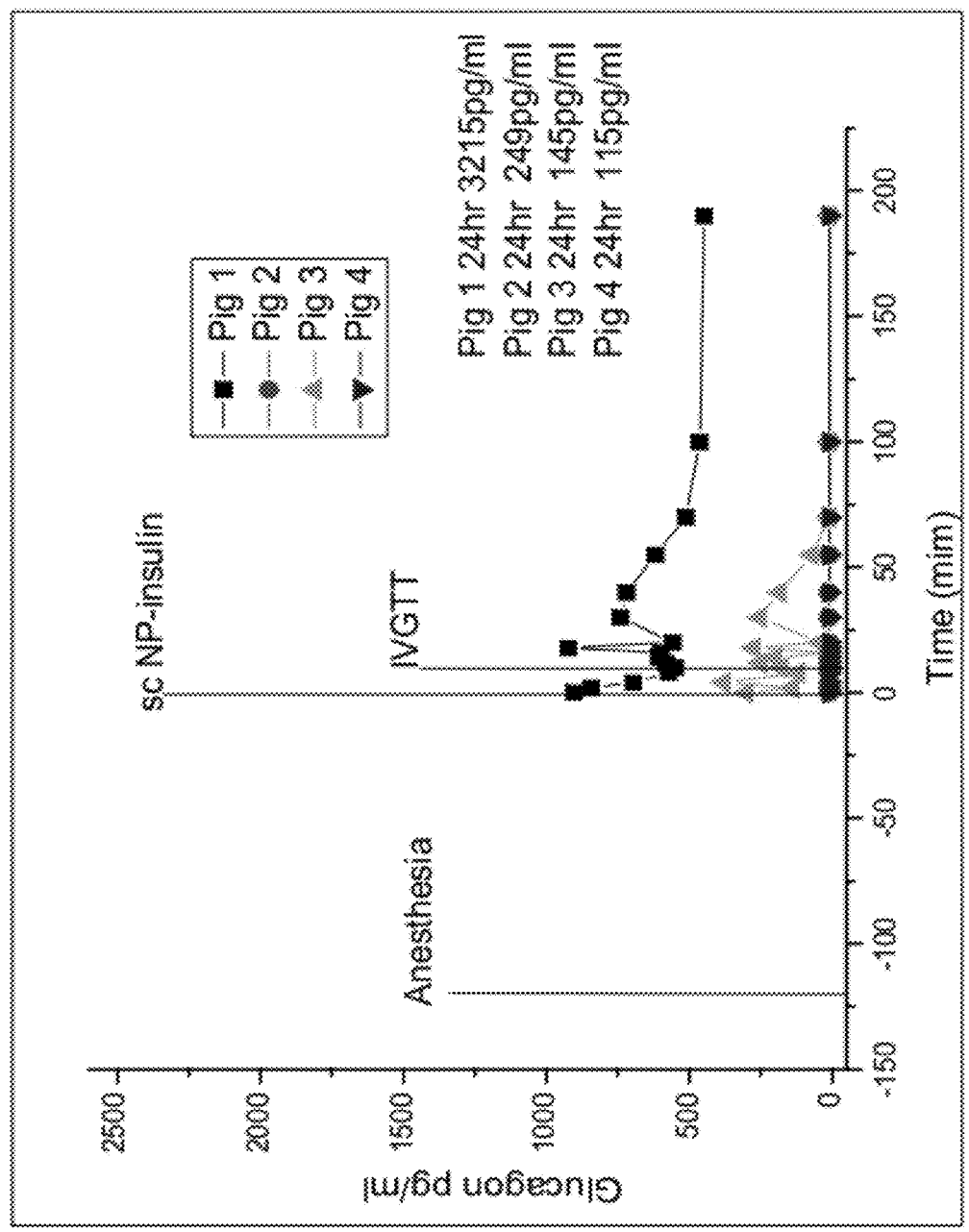
FIG. 27 shows plots (pigs 1-4) of glucagon levels after sub-cutaneous administration of NP-insulin.
Figure 28:
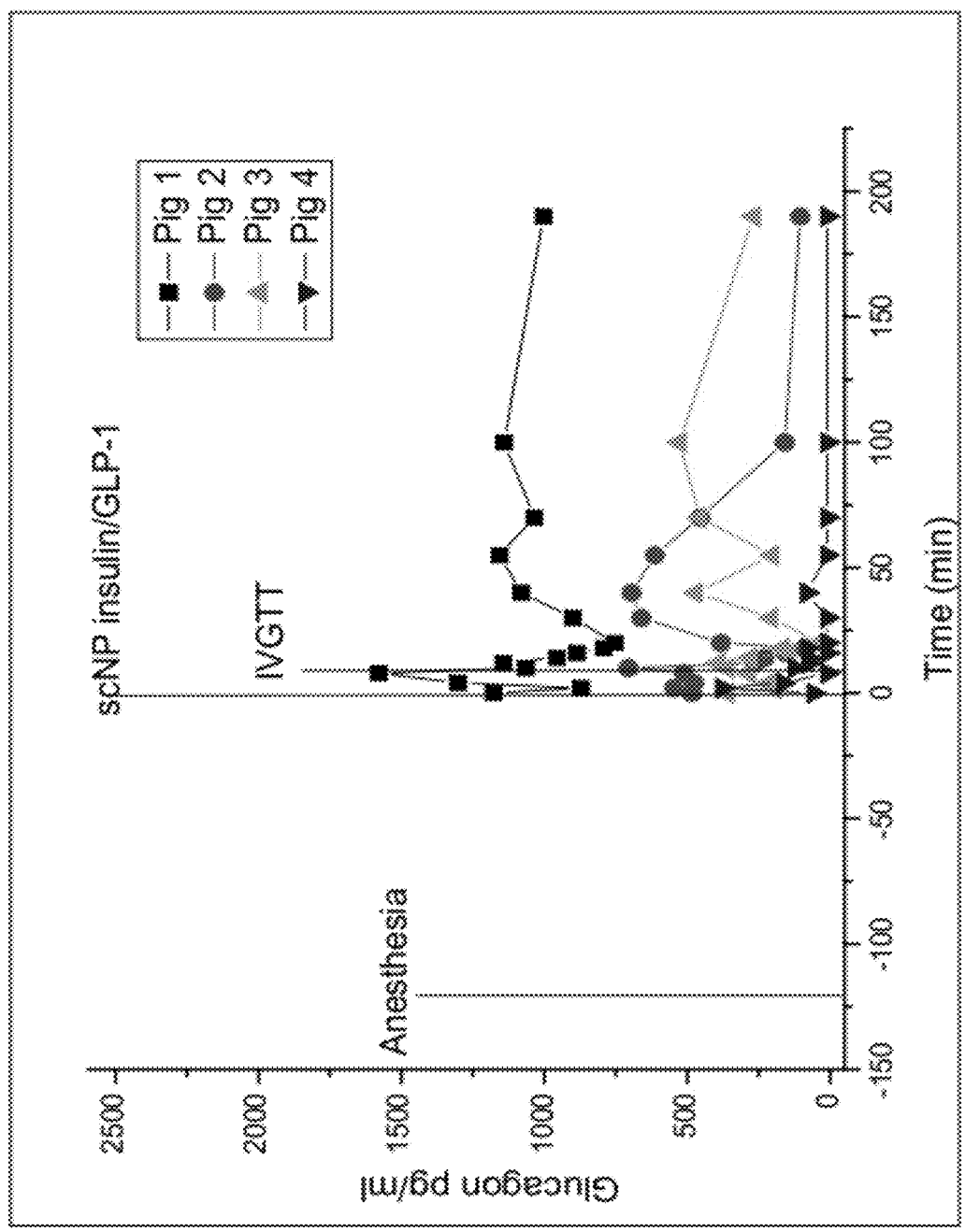
FIG. 28 shows plots (pigs 1-4) of glucagon levels after sub-cutaneous administration of NP-insulin/GLP-1 combination.
Figure 29:
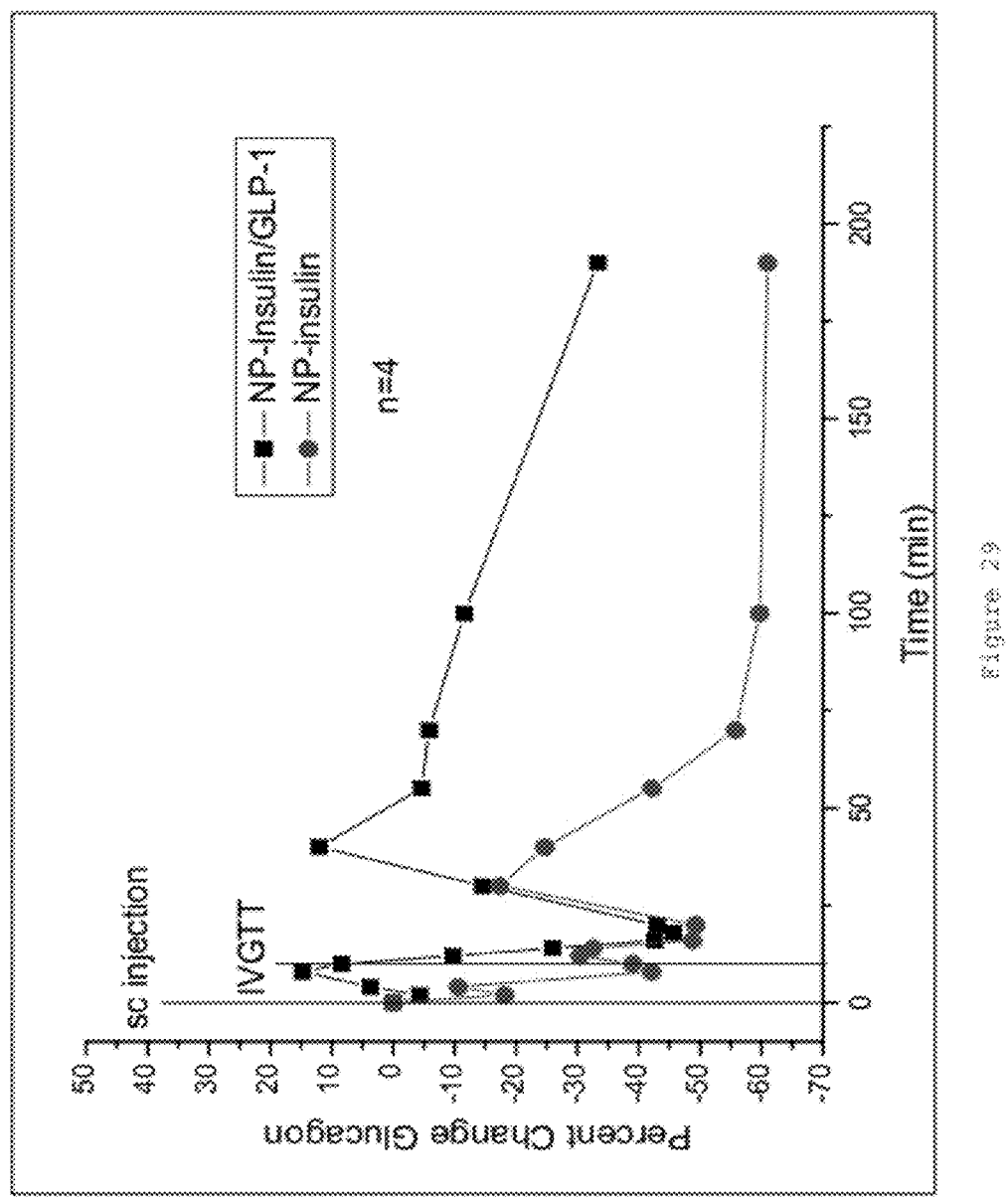
FIG. 29 shows data plotted as the percent change of the glucagon levels, so as to normalize for different starting values of the individual pigs (n=4); the NP-insulin/GLP-1 combination plot is represented by squares and the NP-insulin plot is represented by circles.

FIGS. 27 and 28 show the glucagon levels after administration of NP-insulin and NP-insulin/GLP-1 in individual animals. As we have found previously in the absence of an IVG, subcutaneous (s.c.) NP-insulin has a dramatic effect on maintaining the anaesthesia induced suppression of glucagon. In contrast (FIG. 28) the NP-insulin/GLP-1 particles increased glucagon levels in all animals during the first ten minutes after sc injection. A rapid drop in levels immediately followed the IVG at the ten minute point and then elevated levels returned as the glucose levels returned to normal glycaemia. In FIG. 29 the data is plotted as the mean of the percent change in order to normalize for different starting values. Since none of the animals in the study had hypoglycaemia (FIG. 26), the differences in glucagon response must be a measure of the balance between the counter-hormones required to maintain normal glycaemia rather than a response to hypoglycaemia. These data suggest that the glucose PK shown in FIG. 24 for the NP-insulin/GLP-1 is a balance of the strong glucose lowering action of the NP-insulin which was being counter-acted by the glucose elevating potential of the glucagon. A characteristic of some rapid-acting insulin is to drive hypoglycaemia without a clear counter-hormone response in anesthetized minipigs. The addition of the GLP-1 component to NP-insulin appears to provide a counter-hormone response even in this protocol.

Figure 30:
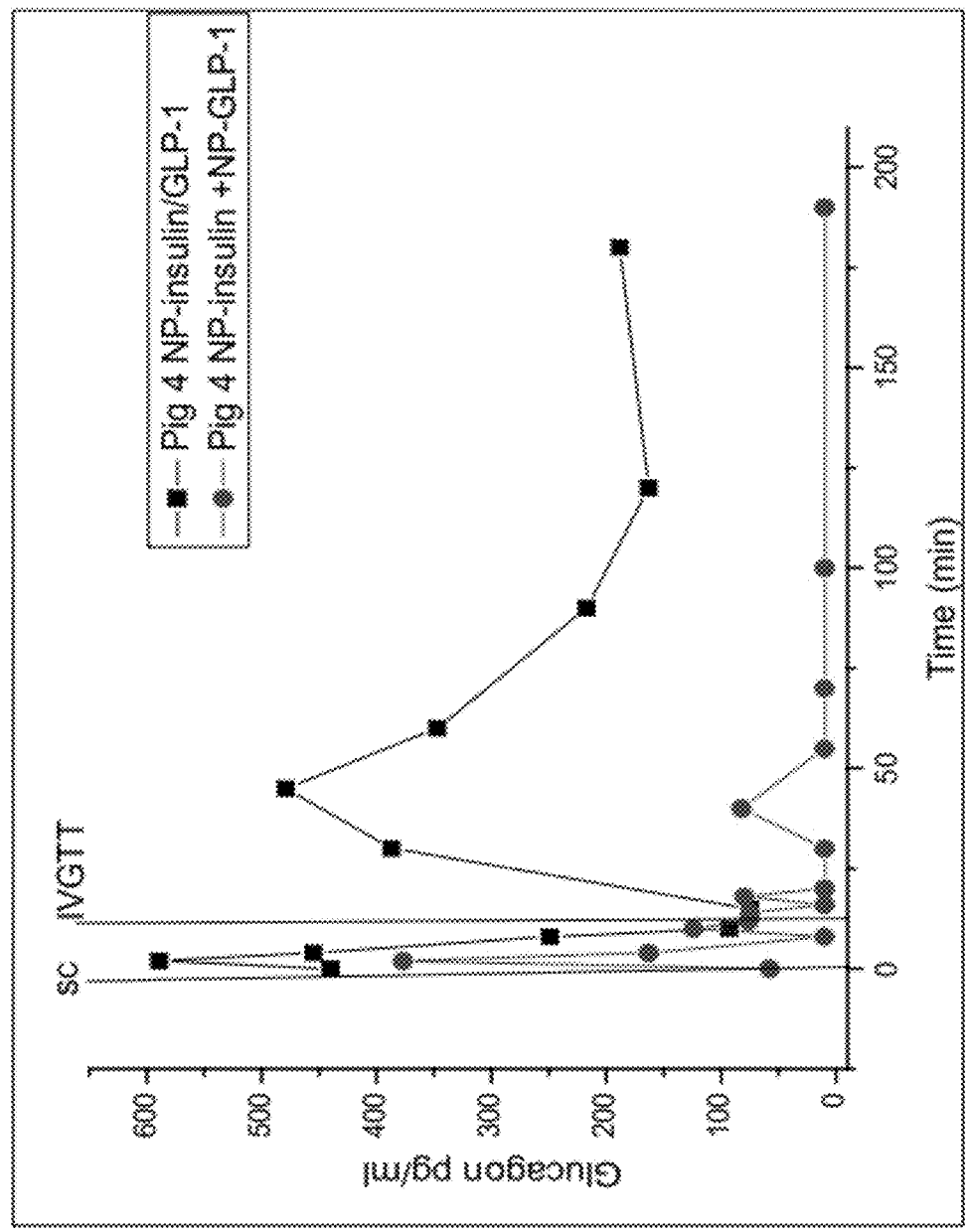
FIG. 30 shows plots of glucagon levels following sub-cutaneous administration of the NP-insulin/GLP-1 combination preparation (squares) and of a mixture of NP-insulin and NP-GLP-1 (circles)

As reported in FIG. 27, we found almost undetectable levels of glucagon after the IVG but these were significantly raised by the administration of the NP-insulin/GLP-1 as shown in FIG. 28. FIG. 30 shows the effect of administering the insulin and GLP-1 on separate particles compared to the NP-insulin/GLP-1 combination. For both test items an initial spike of glucagon was measured followed by a rapid decline and then post IVG an elevation of glucagon levels were significantly elevated for the NP-insulin/GLP-1 particles. This indicates that the NP-insulin/GLP-1 treatment induces a more normal glucagon response (also known as counter-hormone response) as compared with the mixture of NP-insulin and NP-GLP-1. This suggests that the NP-insulin/GLP-1 combination may avoid or minimize any undesirable hypoglycaemia.

This experiment provides preliminary evidence that administering the insulin and GLP-1 on the same particle results in a different PD effect from administering two particles with either GLP-1 or insulin attached. The release rate of the GLP-1 and insulin is rapid in plasma but it would perhaps be expected that some of the NP insulin and GLP-1 remains associated with the particle during at least one circulation. Under this condition either the insulin or the GLP-1 could be acting as a homing molecule such that delivery of the insulin and GLP-1 are to the same target. For example the fate of most administered insulin is the pancreas and therefore this could result in targeting of the GLP-1 to that compartment. In contrast GLP-1 predominantly cleared by the kidney and like insulin is localized to the pancreas and this could result in insulin/GLP-1 delivery to the pancreas but different histological sites.

Figure 31:
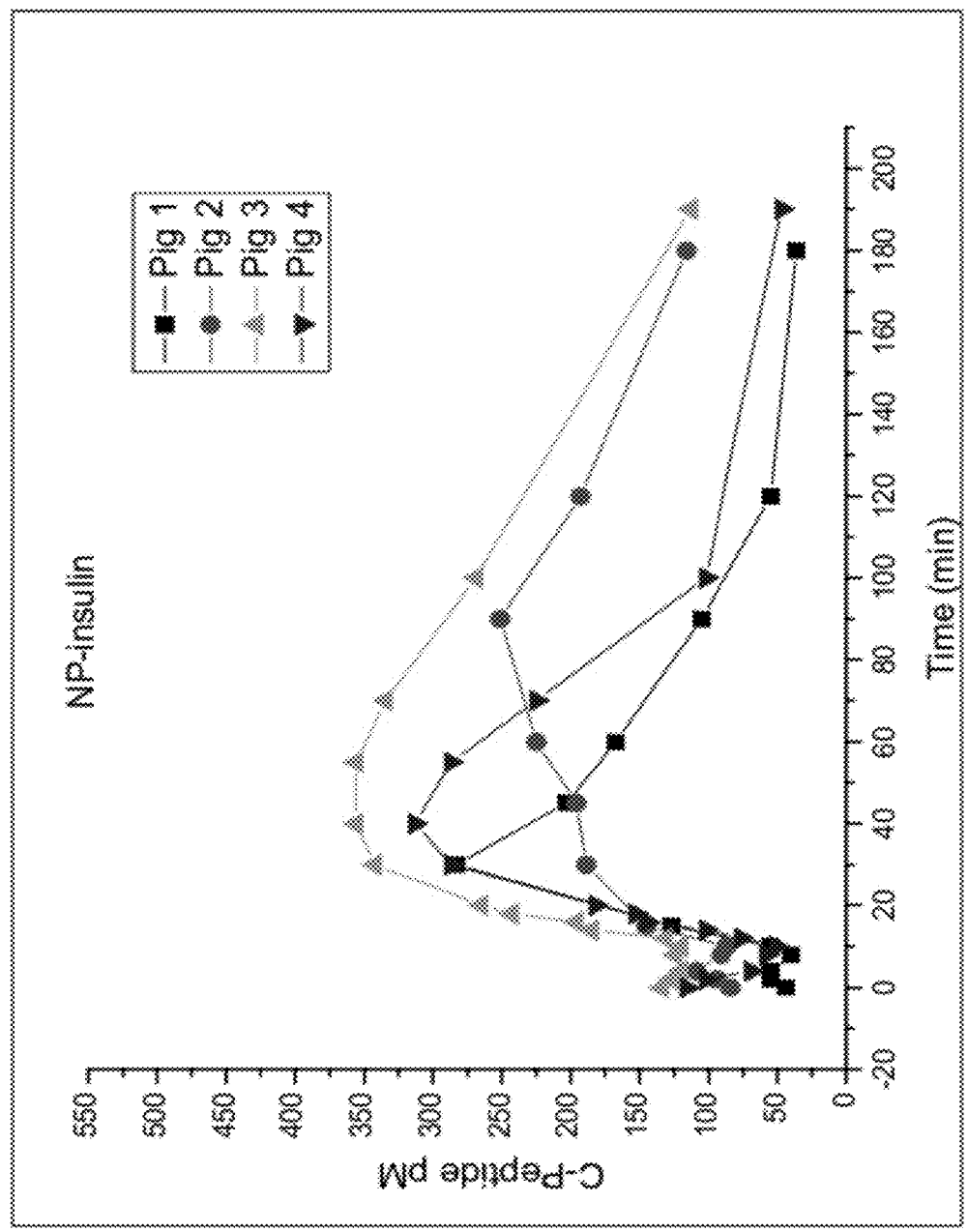
FIG. 31 shows plots (pigs 1-4) of C-peptide levels in response to intravenous glucose (IVG) following sub-cutaneous administration of NP-insulin.
Figure 32:
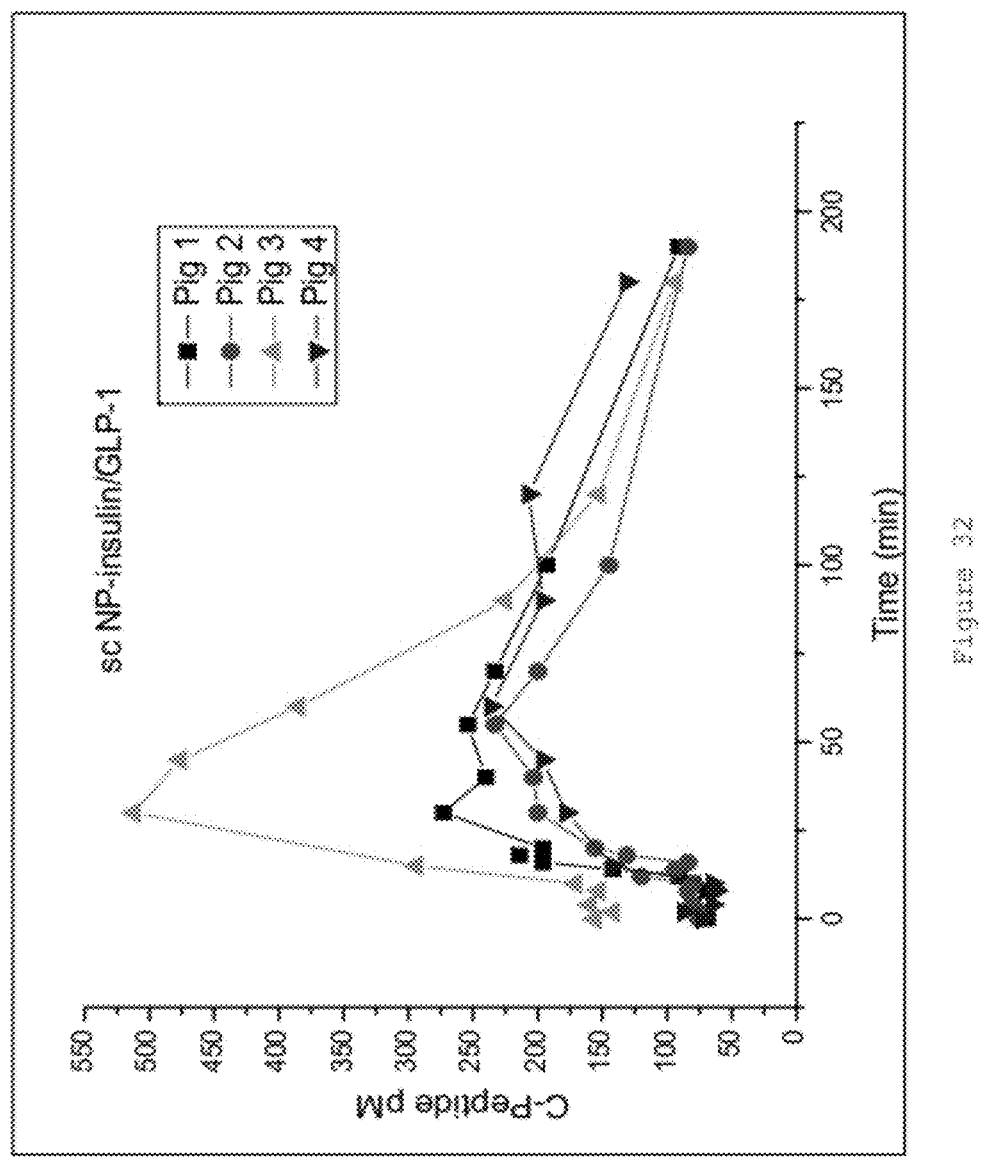
FIG. 32 shows plots (pigs 1-4) of C-peptide levels in response to intravenous glucose (IVG) following sub-cutaneous administration of the NP-insulin/GLP-1 combination preparation.
Figure 33:
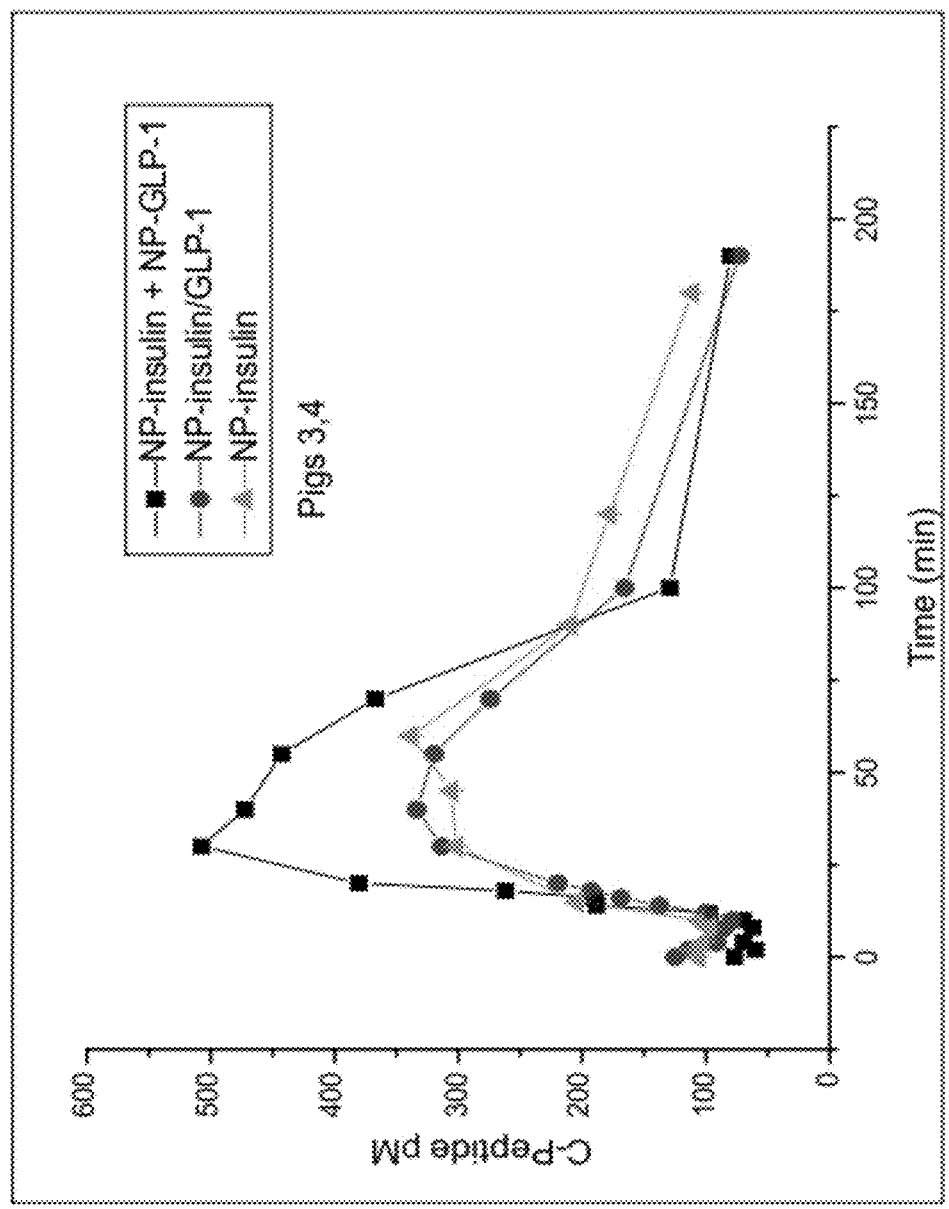
FIG. 33 shows plots (pigs 3 & 4) of C-peptide levels, in which the effects of (i) a mixture of NP-insulin and NP-GLP-1 (squares), (ii) the combination NP-insulin/GLP-1 preparation (circles), and (iii) NP-insulin (triangles) are compared.

FIG. 31 shows the C-peptide response to the IVG after administration of the sc NP-insulin. Insulin doesn't suppress insulin synthesis and the C-peptide levels, in principle, reflect the glucose stimulus to the pancreas and release of endogenous insulin. FIG. 32 shows the individual responses for the same pigs administered NP-insulin/GLP-1. No clear insulinotropic effect of GLP-1 was observed when it is attached to the same particle as insulin, as shown in FIG. 32 except possibly for pig 3. In FIG. 33 no difference in C-peptide synthesis is seen between the NP-insulin and NP-insulin/GLP-1. In contrast, the administration of the insulin and GLP-1 on separate particles has resulted in an insulinotropic effect. This suggests that the NP-insulin/GLP-1 combination advantageously avoids or reduces a GLP-1 induced insulinotropic effect in a subject as compared with the NP-insulin and NP-GLP-1 mixture. The expected GLP-1 insulinotropic response is therefore not observed when the GLP-1 is attached to a particle which also contains insulin. This is further evidence of insulin targeting of the GLP-1. It is controversial but the direct pancreatic effects of GLP-1 may be a counter indication of GLP-1 therapy since pancreatitis and pancreatic tumours have now been reported. The ability to deliver GLP-1 and avoid the insulinotropic activity in the pancreas is a potentially important characteristic of NP-insulin/GLP-1 constructs.

Figure 34:
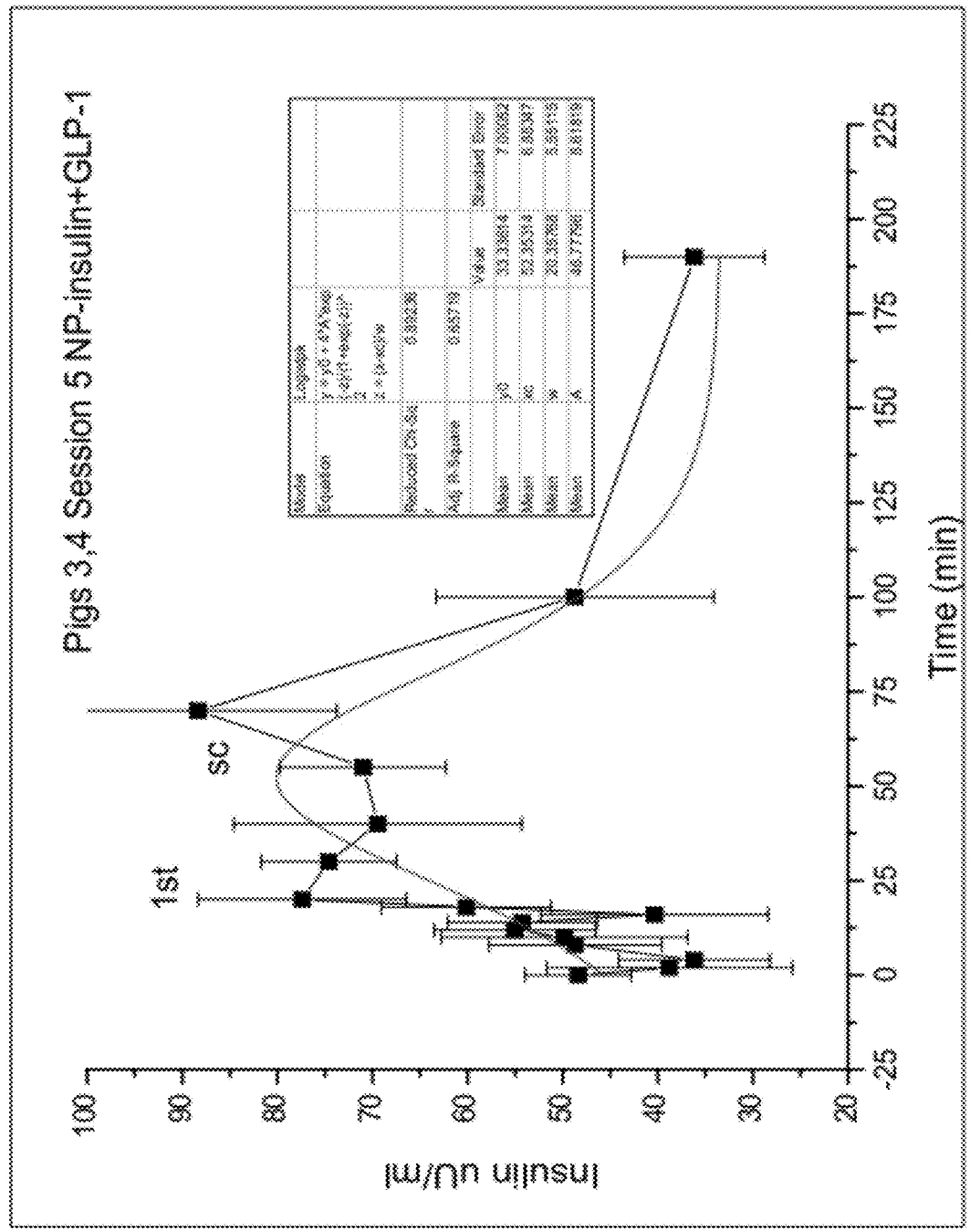
FIG. 34 shows insulin pharmacokinetic data (pigs 3 & 4) following treatment with a mixture of NP-insulin and NP-GLP-1.
Figure 35:
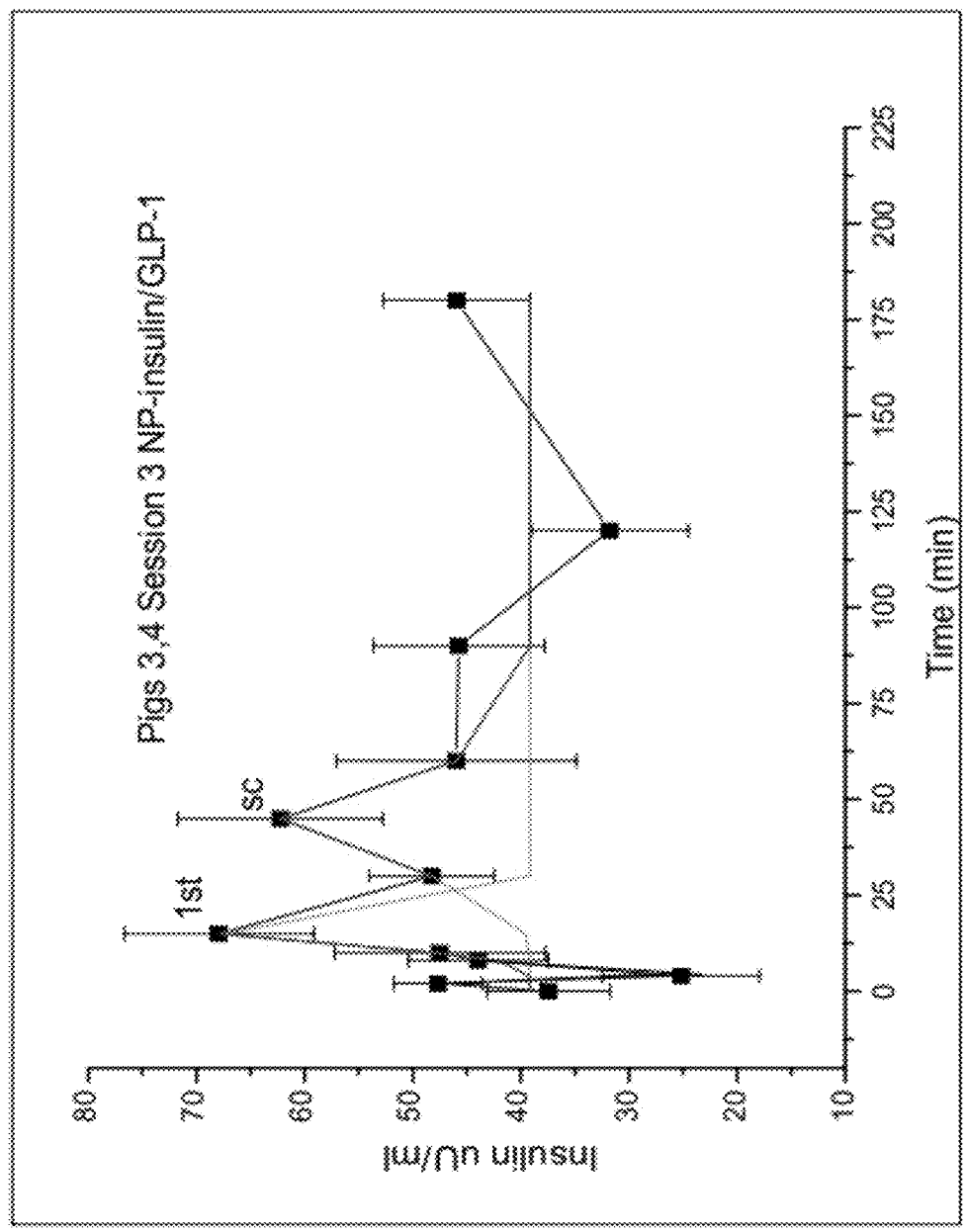
FIG. 35 shows insulin pharmacokinetic data (pigs 3 & 4) following treatment with the combination NP-insulin/GLP-1 preparation.

The strong insulinotropic effect is also clearly seen in the insulin PK measurements as shown in FIG. 34 which shows the data for pigs when treated with a mixture of particles and FIG. 34 shows that the composite picture of the endogenous insulin release which has been enhanced by the insulinotropic action of GLP-1 and the exogenous NP-insulin which was administered s.c. From the entrainment experiments we know that the pre-treatment of the animals ten minutes prior to the IVG induced receptor blockade and we can observe predominantly the PK of endogenously produced monomeric insulin. FIG. 35 shows the insulin PK after using the NP-insulin/GLP- 1. FIG. 36 shows the effect of an intravenous infusion of NP-GLP-1 compared to control and free GLP-1 simultaneous with a glucose infusion. Under these conditions GLP-1 is thought to enhance the 1st and 2nd phase response by either an insulinotropic effect or by enhancing insulin $C_{max}$ by reducing the clearance or degradation of insulin. This confirms that the NP-insulin/GLP particles are providing the stabilization activity of GLP-1 (peak around 10-12 minutes) but not the insulintropic effect which is evident post 50-75 minutes, as shown in FIG. 34.

The insulinotropic effect of GLP-1 is controversial since it is difficult to explain how endogenous GLP-1 is able to anatomically reach the pancreas prior to it being degraded. GLP-1 is also thought to be released into lymphatics that make its biodistribution more difficult to predict. Analogue GLP-1s have longer plasma half-lives and clearly would be able to reach the pancreas and have an insulinotropic effect, however, this action may be associated with abnormal physiology such as overstimulation of islets cell and pancreatitis. It is clear that the NP-insulin/GLP-1 and the mixture of the two particles have different biological effects. The biodistribution of the two constructs may be very different depending on the relative release rates of the two peptides when they are attached to the same particle. The "side car" phenomena could be important in determining the final biological outcome.

In summary the ability to separate out the ability of GLP-1 to increase insulin $C_{max}$ and avoid a pancreatic insulinotropic effect could be of significant medical benefit—possibly reducing the risk of pancreatitis. Diabetic patients do not have a defect in the quantity of intestinal endogenous GLP-1 released after a meal or glucose challenge. But peripheral insulin resistance in diabetics is paralleled by GLP-1 tissue resistance—i.e. reduced bioactivity at the receptor organs and the metabolic mechanisms may be identical. The main therapeutic action then for GLP-1 treatment should therefore be aimed at enhancing the bioavailability of insulin either endogenously produced or exogenously administered. The ability of NP-insulin/GLP to solve both of these problems is very attractive for a therapeutic product.

Example 9

As mentioned above, the compositions of the present invention may be delivered via nasal delivery. For example, an aqueous solution containing insulin/GLP-1 nanoparticles may be formulated and applied in the form of a spray to the nasal membranes using an atomizer, a nebulizer or a sprayer. The spray of the solution carrying the nanoparticles are contacted with the nasal mucus membrane and absorbed thereby. For example, the nasal delivery systems may include various components such as isotonic agents, buffers, preservatives, antiseptics, surfactants, and stabilizing agents and combinations thereof. For example, the insulin/GLP-1 nanoparticles of Example 7 are combined with an aqueous, buffered solution for nasal delivery.

Example 10

Insulin Film Strips (1 IU)

A film matrix composition is prepared with the following components and the process described below
1. 5.171 g (49.25%) Polyethylene oxide (PEO) WSR N10 LEO (Dow)
2. 2.586 g (24.63%) HPMC E15 (Dow)
3. 1.724 g Maltitol Syrup (Lycasin 80/55) (Roquette) containing 1.293 g (12.31%) solids and 0.431 g Water
4. 1.293 g (12.31%) Natural Glycerin (Spectrum)
5. 0.053 g (0.50%) Span 80 (Spectrum)
6. 0.105 g (1.00%) Titanium Dioxide USP (Brenntag)
7. 3.0 ml of insulin/GLP-1 nanoparticles (Midatech)
8. 14.069 g Sterile Water USP (McGaw)

Components 3, 4, 5, 6, and 8 are added to a fabricated glass bowl. Then a blend of components 1 and 2 are added to the bowl. The solution is prepared as described below using the Degussa Dental Multivac Compact.
40 minutes stirring=100 rpm vacuum=60% (16 in Hg)
40 minutes stirring=100 rpm vacuum=90% (25 in Hg)
12 minutes stirring=100 rpm vacuum=95% (27 in Hg)
8 minutes stirring=100 rpm vacuum=98% (27.5 in Hg)
Add sterile water to obtain QS
4 minutes stirring=100 rpm vacuum=100% (28.5 in Hg)
Add component 7
Add sterile water to obtain QS
8 minutes stirring=100 rpm vacuum=100% (28.5 in Hg)

The solution is cast into 2 sheets of film using the K-Control Coater with the micrometer adjustable wedge bar set at 440 to 460 microns onto the HDP side of paper substrate. One film is dried 15 minutes at 100° C. in a convection air oven and the other film is dried 30 minutes at 60° C. in a convection air oven. Drying is done in accordance with the invention to produce uniformity of content in the resultant film and unit doses cut therefrom. The films are cut into 0.875×0.5 inch strips which weigh 33 to 39 mg.

Example 11

Oral Active Strips Containing 20 IU Insulin and 69 Micrograms GLP-1 Per Strip (Insulin/GLP-1 Molar Ratio 7:1) for Sublingual Delivery The below ingredients are added to a fabricated glass bowl.
1. 2.868 grams (47.310%) Polyethylene oxide (PEO) WSR N10 LEO (Colorcon)
2. 1.434 grams (23.660%) HPMC E15 (Dow)
3. 0.956 grams maltitol syrup (Lycasin 80/55) (75% solids) (Roquette) containing 0.717 grams (11.825%) maltitol and 0.239 g water
4. 0.717 grams (11.825%) glycerin (Spectrum)
5. 0.029 grams (0.480%) Peceol (Gattefosse)
6. 0.058 grams (0.961%) titanium dioxide (Brenntag)
7. 10 grams of a gold/ligand/insulin/GLP-1 suspension containing 0.239 grams (3.939%) gold/ligand/insulin/GLP-1 and 9.761 g water (Midatech) (6062.8 IU insulin and 0.021 g GLP-1) (Insulin:GLP-1 Molar Ratio of 7:1)
8. 4.146 g sterile water (Braun)

The bowl is equipped with a stirrer top. A solution is prepared using the Degussa Dental Multivac Compact with stirring and vacuum as described below:
40 minutes stirring=125 rpm vacuum=60% (18 in Hg)
40 minutes stirring=125 rpm vacuum=90% (25.5 in Hg)
12 minutes stirring=125 rpm vacuum=95% (27 in Hg)
8 minutes stirring=125 rpm vacuum=98% (27.5 in Hg)
Added sterile water to compensate for water lost
10 minutes stirring=125 rpm vacuum=100% (28.5 in Hg)

The solution is cast into wet film using the K Control Coater with the micrometer adjustable wedge bar set at 335 microns onto mylar substrate. The film is dried 20 minutes in an 80 C. air oven. The film has a % moisture content of 2.80. The film sheets are cut into 14×18 mm strips. The film strips have a dry target strip weight of 20 mg and a target strip weight corrected for moisture of 20.58 mg. Each strip contains 20 IU insulin and 69 micrograms GLP-1 with an insulin/GLP-1 molar ratio of 7:1. The strip is administered to the patient by placing under the tongue for dissolution.

Example 12

Slow Occlusive Film for Bi Layer Active Film to Obtain Bioadhesion

The ingredients used in the slow occlusive film are shown below:
1. 7.85 grams (7.48%) PEO WSR 1105 LEO (Colorcon)
2. 53.97 grams (51.40%) PEO WSR N80 LEO (Colorcon)
3. 17.01 grams maltitol syrup (Lycasin 80/55) (75% solids) (Roquette) containing 12.76 grams (12.15%) maltitol and 4.25 grams water
4. 12.76 grams (12.15%) glycerin (Spectrum)
5. 10.79 grams (10.28%) HPMC E15 (Dow)
6. 2.10 grams (2.00%) sucralose (EMD)
7. 4.20 grams (4.00%) peppermint 2303 flavor (Ungerer)
8. 0.53 grams (0.50%) Peceol (Gattefosse)
9. 0.04 grams (0.04%) FD & C blue granular (Sensient Tech)
10. 240.75 grams sterile water (Braun)

The PEO WSR 1105, maltitol syrup, glycerin, peceol, and sterile water are added to a fabricated glass bowl. The bowl is equipped with a heating mantel and the heat is turned on. The solution is prepared as described below:
24 minutes stirring=150 rpm vacuum=0% Temperature=73.5 C.
40 minutes stirring=150 rpm vacuum=0% Temperature=60 C.
The heat is cut off and the heating mantel is removed
A blend of PEO WSR N80 LEO, HPMC E15, sucralose, and FD & C blue granular is added to the bowl.
Sterile water is added to compensate for water lost.
20 minutes stirring=100 rpm vacuum=60% (18 in Hg)
12 minutes stirring=100 rpm vacuum=90% (27 in Hg)
28 minutes stirring=100 rpm vacuum=100% (28.5 in Hg)
The peppermint flavor is added.
Sterile water is added to compensate for water lost.
8 minutes stirring=150 rpm vacuum=100% (28.5 in Hg)

The solution is cast into wet films using the K-Control Coater with the micrometer adjustable wedge bar set at 900 microns onto mylar substrate. The film is dried for 27 minutes in an 80 C. oven. The film has a % moisture of 2.46. The film sheets are cut into 22×190 mm strips. The acceptable weight range for the strips is 0.79 grams to 0.97 grams. One of the 22×190 mm strips is cut into ten 22×18 mm strips which have an average strip weight of 80 mg. These 18×22 mm strips of slow occlusive film are for preparing bi-layer films strips of gold/ligand/insulin/GLP-1 to allow bioadhesion.

Example 13

Oral Bi-Layer Film Strips of 20 IU Insulin/60 Micrograms GLP-1 with an Insulin/GLP-1 Molar Ratio of 7:1 for Buccal Delivery One of the 14×18 mm active strips containing 20 IU insulin and 69 micrograms GLP-1 from Example 1 is centered on one of the 18×22 mm strips of occlusive film from Example 2. The strips are placed in a folded sheet of HDPE 6330L paper. The strips in the folded sheet of paper are allowed to pass twice through the GBC Heat Sealer H212 at a temperature of 88 to 90 C. After cooling for 2 minutes, the laminated strip is removed from between the paper substrate. The process is repeated to obtain additional laminated strips. Each laminated strip contains 20 IU insulin and 69 micrograms GLP-1 with an insulin:GLP-1 molar ratio of 7:1. The laminated bi-layer oral film strip is administered to the patent in the buccal area with the active strip placed in the downward position toward the buccal area.

Example 14

Intravenous Injectable Sterile Nano/Insulin/GLP-1 Formulation 1.65 ml of a suspension of gold nano/ligand/insulin/GLP-1 (insulin:glp-1 at 7:1 molecular ratio), containing 606 IU insulin/ml is added to a 20 ml vial for a total of 1000 IU of insulin and 3,450 micrograms of GLP-1. To this suspension are added 30 mg of m-cresol and 160 mg of glycerin. To the mixture is added sterile water quantity sufficient to 10 g. The suspension/solution is brought to a pH of 7.4 using 2 N HCl and 2 N sodium hydroxide. Each ml of intravenous injection contains 100 IU of insulin and 345 micrograms of GLP-1.

Example 15

Subcutaneous Injectable Sterile Nano/Insulin/GLP-1 Formulation 1.65 ml of a suspension of gold/nano/ligand/insulin/GLP-1 (insulin:glp-1 at 7:1 molecular ratio), containing 606 IU insulin/ml is added to a 20 ml vial for a total of 1000 IU of insulin and 3,450 micrograms of GLP-1. To this suspension is added 3 mg of m-cresol, 6 mg tromethamine, 5 mg sodium chloride and 0.01 mg Polysorbate 20. To the mixture is added sterile water quantity sufficient to 10 g. The suspension/solution is brought to a pH of 7.4 using 2 N HCl and 2 N sodium hydroxide. Each ml of subcutaneous injection contains 100 IU of insulin and 345 micrograms of GLP-1.

Example 16

Lyophilized Tablet Formulation of Insulin/GLP-1

Six grams of gold/nano/ligand/insulin/GLP-1 (insulin:glp-1 at 7:1 molecular ratio), containing 3,636 IU insulin and 12.544 mg of GLP-1 is added to 74 grams of distilled water. To this solution is added 10 grams of 125 bloom gelatin, 6 grams of mannitol, 2 grams of glycerin, 0.5 grams of sucralose and 1.5 grams of peppermint flavor. The ingredients are mixed until the gelatin is in solution. Five hundred fifty mg's of the solution is pipetted into one hundred and eighty one (1) one cm diameter blister packs. The solution is freeze dried in a Navalyphe-N2 500 Freeze Dryer and packaged with an aluminum foil backing. Each lyophilized tablet contains 20 mg of insulin and 69 micrograms of GLP-1+ or −10%. The process flow is as follows:
Active+Polymer Carrier Solution→Blister Packs→Nitrogen Freeze Drying Tunnel→Lyophilized→Aluminum Foil Backed Packaging All references cited herein are incorporated herein by reference in their entirety and for all purposes to the same extent as if each individual publication or patent or patent application was specifically and individually indicated to be incorporated by reference in its entirety.

The specific embodiments described herein are offered by way of example, not by way of limitation. Any sub-titles herein are included for convenience only, and are not to be construed as limiting the disclosure in any way.

The invention claimed is:

1. A therapeutic or bioaffecting film delivery system comprising:
   (a) one or more film matrices comprising at least one polymer;
   (b) a plurality of nanoparticles incorporated in at least one of said film matrices, said nanoparticles comprising:
      (i) a core comprising a metal and/or a semiconductor;
      (ii) a corona comprising a plurality of ligands covalently linked to the core, wherein at least one of said ligands comprises a carbohydrate moiety; and
      (iii) at least a first peptide and a second peptide bound to the corona.

2. The film delivery system according to claim 1, wherein a molar ratio of said first peptide to said second peptide is in the range 1:100 to 100:1.

3. The film delivery system according to claim 2, wherein the first and second peptides are bound to the corona such that at least a fraction of the bound peptides is released from the nanoparticle upon contacting the nanoparticle with a physiological solution.

4. The film delivery system according to claim 3, wherein said release comprises dissociation of bound peptide molecules from the nanoparticle rapidly within minutes followed by further sustained release over a period of at least 2 or more hours.

5. The film delivery system according to claim 4, wherein said release comprises dissociation of bound peptide molecules from the nanoparticle over a period of at least 4 or more hours.

6. The film delivery system according to claim 5, wherein the at least one of the first and second peptides is capable of stimulating a reduction in blood glucose levels in a mammalian subject.

7. The film delivery system according to claim 1, wherein the first and second peptides are reversibly bound to the corona.

8. The film delivery system according to claim 1, wherein at least one of the first and second peptides is capable of stimulating a physiologic response in a mammalian subject.

9. The film delivery system according to claim 1, wherein the first and second peptides are individually selected from the group consisting of insulin, GLP-1, and exenatide.

10. The film delivery system according to claim 9, wherein the insulin is monomeric and/or dimeric human insulin.

11. The film delivery system according to claim 1, wherein the first and second peptides are individually selected from the group consisting of: insulin, GLP-1, exenatide, IGF1, IGF2, relaxin, INSL5, INSL6, INSL7, pancreatic polypeptide (PP), peptide tyrosine tyrosine (PTT), neuropeptide Y, oxytocin, vasopressin, GnRH, TRH, CRH, GHRH/somatostatin, FSH, LH, TSH, CGA, prolactin, ClIP, ACTH, MSH, enorphins, lipotropin, GH, calcitonin, PTH, inhibin, relaxin, hCG, HPL, glucagons, somatostatin, melatonin, thymosin, thmulin, gastrin, ghrelin, thymopoietin, CCK, GIP secretin, motin VIP, enteroglucagon, IGF-1, IGF-2, leptin, adiponectin, resistin Osteocalcin, renin, EPO, calicitrol, ANP, BNP, chemokines, cytokines, adipokines, PYY (3-36), and oxyntomodulin.

12. The film delivery system according to 1, wherein the first peptide comprises insulin and the second peptide comprises GLP-1, and wherein a molar ratio of insulin to GLP-1 is in the range of about 5:1 to about 20:1.

13. The film delivery system according to claim 12, wherein the carbohydrate moiety comprises a galactopyranoside and/or a glucopyranoside.

14. The film delivery system according to claim 1, wherein the carbohydrate moiety comprises a monosaccharide and/or a disaccharide.

15. The film delivery system according to claim 14, wherein the carbohydrate moiety comprises a glycoside of: galactose, glucose, glucosamine, N-acetylglucosamine, mannose, fucose, lactose, or a combination thereof.

16. The film delivery system according to claim 1, wherein the carbohydrate moiety is covalently linked to the core via a linker selected from the group consisting of: sulphur-containing linkers, amino-containing linkers, phosphate-containing linkers and oxygen-containing linkers.

17. The film delivery system according to claim 16, wherein the linker comprises an alkyl chain of at least two carbons.

18. The film delivery system according to claim 1, wherein said at least one ligand comprising a carbohydrate moiety is selected from the group consisting of: 2'-thioethyl-α-D-galactopyranoside, 2'-thioethyl-β-D-glucopyranoside, 2'-thioethyl-2-acetamido-2-deoxy-β-D-glucopyranoside, 5'-thiopentanyl-2-deoxy-2-imidazolacetamido-α,β-D-glucopyranoside and 2'-thioethyl-α-D-glucopyranoside, and wherein said at least one ligand comprising a carbohydrate moiety is covalently linked to the core via the thiol sulphur.

19. The film delivery system according to claim 1, wherein said plurality of ligands covalently linked to the core further comprises at least one non-carbohydrate ligand.

20. The film delivery system according to claim 19, wherein said at least one non-carbohydrate ligand comprises an amine group.

21. The film delivery system according to claim 19, wherein said at least one non-carbohydrate ligand comprises 1-amino-17-mercapto-3,6,9,12,15,-pentaoxa-heptadecanol covalently linked to the core via the thiol sulphur.

22. The film delivery system according to claim 19, wherein said at least one ligand comprising a carbohydrate moiety and said at least one non-carbohydrate ligand are different and are present on the nanoparticle in a ratio of 1:40 to 40:1.

23. The film delivery system according to claim 22, wherein in the ratio is 1:10 to 10:1.

24. The film delivery system according to claim 23, wherein the ratio is 1:2 to 2:1.

25. The film delivery system according claim 1, wherein the corona comprises at least 5 ligands per core.

26. The film delivery system according to claim 25, wherein the corona comprises about 10 to about 1000 ligands per core.

27. The film delivery system according to claim 26, wherein the corona comprises 44-106 ligands per core.

28. The film delivery system according to claim 1, wherein at least 5 or more peptide molecules are bound per core.

29. The film delivery system according to claim 1, wherein the core comprises a metal selected from the group consisting of: Au, Ag, Cu, Pt, Pd, Fe, Co, Gd, Zn or any combination thereof.

30. The film delivery system according to claim 29, wherein the core comprises a passive metal selected from the group consisting of: Au, Ag, Pt, Pd and Cu, or any combination thereof.

31. The film delivery system according to claim 29, wherein the core comprises a combination of metals selected from the group consisting of: Au/Fe, Au/Ag, Au/Cu, Au/Ag/Cu, Au/Pt, Au/Pd, Au/Ag/Cu/Pd, Au/Gd, Au/Fe/Cu, Au/Fe/Gd, Au/Fe/Cu/Gd.

32. The film delivery system according to claim 1, wherein the core is magnetic.

33. The film delivery system according to claim 1, wherein the core further comprises an NMR active atom selected from the group consisting of: $Mn^{2+}$, $Gd^{3+}$, $Eu^{2+}$, $Cu^{2+}$, $V^{2+}$, $Co^{2+}$, $Ni^{2+}$, $Fe^{3+}$ and lanthanides$^{3+}$.

34. The film delivery system according to claim 1, wherein the core further comprises a semiconductor.

35. The film delivery system according to claim 34, wherein the semiconductor is selected from the group consisting of: cadmium selenide, cadmium sulphide, cadmium tellurium and zinc sulphide.

36. The film delivery system according to claim 1, wherein the core comprises a metal oxide coated with a metal selected from the group consisting of: Au, Ag, Cu, Pt, Pd and Zn, or any combination thereof.

37. The film delivery system according to claim 36, wherein said metal oxide is of the formula $XFe_2O_4$, where X is a metal selected from the group consisting of: Fe, Mn and Co.

38. The film delivery system according to claim 1, wherein the nanoparticle cores have an average diameter in the range of about 0.5 nm to about 50 nm.

39. The film delivery system according to claim 38, wherein said average diameter is in the range of about 1 nm to about 10 nm.

40. The film delivery system according to claim 39, wherein said average diameter is in the range of about 1.5 nm to about 2 nm.

41. The film delivery system according to claim 40, wherein said divalent component is present in an amount sufficient to produce a stabilizing effect.

42. The film delivery system according to claim 41, wherein said divalent component is present in an amount of about 0.5 to about 2.0 equivalents of said metal in said core.

43. The film delivery system according to claim 42, wherein said divalent component is present in an amount of about 0.75 to about 1.5 equivalents of said metal in said core.

44. The film delivery system according to claim 1, wherein the nanoparticle core comprises a divalent component.

45. The film delivery system according to claim 44, wherein said divalent component is present in the corona of the nanoparticle.

46. The film delivery system according to claim 45, wherein said divalent component is selected from the group consisting of zinc, magnesium, copper, nickel, cobalt, cadmium, or calcium, their oxides and salts thereof.

47. The film delivery system according to claim 46, wherein said zinc is selected from: $Zn^{2+}$ and ZnO.

48. The film delivery system according to claim 47, wherein the zinc comprises $ZnCl_2$.

49. The film delivery system according to claim 44, wherein said divalent component is selected from the group consisting of divalent metals, divalent metal compounds or other components having a divalent state.

50. The film delivery system according to claim 44, wherein the first and second peptides are reversibly bound to the corona.

51. The film delivery system according to claim 50, wherein the first and second peptides are bound to the corona such that at least a fraction of the bound peptides is released from the nanoparticle upon contacting the nanoparticle with a physiological solution.

52. The film delivery system according to claim 51, wherein said release comprises dissociation of bound peptide molecules from the nanoparticle rapidly within minutes followed by further sustained release over a period of at least 2 or more hours.

53. The film delivery system according to claim 52, wherein said release comprises dissociation of bound peptide molecules from the nanoparticle over a period of at least 4 or more hours.

54. The film delivery system according to claim 52, wherein at least one of the first and second peptides is capable of stimulating a physiologic response in a mammalian subject.

55. The film delivery system according to claim 52, wherein the first and second peptides are insulin and GLP-1.

56. The film delivery system according to claim 52, wherein the first peptide comprises insulin and the second peptide comprises GLP-1, and wherein a molar ratio of insulin to GLP-1 is in the range of about 5:1 to about 20:1.

57. The film delivery system according to claim 1, wherein the one or more film matrices are formed by evaporating a solvent carrier from the matrices to form a visco-elastic film within the first 10 minutes of applying heat or radiation energy whereby the nanoparticles are locked in or substantially prevented from migrating with the matrices to provide a film delivery system with a substantially uniform distribution of the nanoparticles.

58. The film delivery system of claim 57, wherein said solvent is selected from the group consisting of water, polar organic solvent, and combinations thereof.

59. The film delivery system according to claim 1, wherein the one or more film matrices comprise two film layers having different release properties.

60. The film delivery system according to claim 1, wherein the one or more film matrices comprise at least one water soluble or water swellable polymer.

61. The film delivery system according to claim 60, wherein the at least one water soluble or water swellable polymer is selected from the group consisting of polyethylene oxide, cellulose, a cellulose derivative, pullulan, polyvinyl pyrrolidone, polyvinyl alcohol, polyethylene glycol, carboxyvinyl copolymers, hydroxypropylmethyl cellulose, hydroxyethyl cellulose, hydroxypropyl cellulose, carboxymethyl cellulose, sodium alginate, xanthan gum, tragancanth gum, guar gum, acacia gum, arabic gum, polyacrylic acid, methylmethacrylate copolymer, carboxyvinyl copolymers, starch, gelatin, and combinations thereof, alone or in combination with polyethylene oxide.

62. The film delivery system of claim 60, wherein the at least one water soluble or water swellable polymer is selected from the group consisting of ethylcellulose, hydroxypropyl ethyl cellulose, cellulose acetate phthalate, hydroxypropyl methyl cellulose phthalate, polyvinylacetatephthalates, phthalated gelatin, crosslinked gelatin, poly(lactic acid)/poly (glycolic acid)/polyethyleneglycol copolymers, polycaprolactone and combinations thereof.

63. The film delivery system of claim 60, wherein the at least one water soluble or water swellable polymer is selected from the group consisting selected from the group consisting of methylmethacrylate copolymer, polyacrylic acid polymer, poly(glycolic acid) (PGA), poly(lactic acid) (PLA), poly(lactic acid)/poly(glycolic acid)/polyethyleneglycol copolymers, polydioxanoes, polyoxalates, poly(α-esters), polyanhydrides, polyacetates, polycaprolactones, poly(orthoesters), polyamino acides, polyaminocarbonates, polyurethanes, polycarbonates, polyamides, poly(alkyl cyanoacrylates), and mixtures and copolymers thereof.

64. The film delivery system of claim 60, wherein said at least one water soluble or water swellable polymer comprises a polymer selected from the group consisting of sodium alginate, xanthan gum, tragancanth gum, guar gum, acacia gum, arabic gum, starch, gelatin, carageenan, locust bean gum, dextran, gellan gum and combinations thereof.

65. The film delivery system of claim 60, wherein said at least one water soluble or water swellable polymer comprises a polymer selected from the group consisting of ethylcellulose, hydroxypropyl ethyl cellulose, cellulose acetate phthalate, hydroxypropyl methyl cellulose phthalate, polyvinylacetatephthalates, phthalated gelatin, crosslinked gelatin, poly(lactic acid)/poly(glycolic acid)/polyethyleneglycol copolymers, polycaprolactone, methylmethacrylate copolymer, polyacrylic acid polymer, poly(glycolic acid) (PGA), poly(lactic acid) (PLA), poly(lactic acid)/poly(glycolic acid)/polyethyleneglycol copolymers, polydioxanoes, polyoxalates, poly($\alpha$-esters), polyanhydrides, polyacetates, polycaprolactones, poly(orthoesters), polyamino acides, polyaminocarbonates, polyurethanes, polycarbonates, polyamides, poly(alkyl cyanoacrylates), sodium alginate, xanthan gum, tragancanth gum, guar gum, acacia gum, arabic gum, starch, gelatin, carageenan, locust bean gum, dextran, gellan gum and combinations thereof.

66. The film delivery system according to claim 1, wherein the nanoparticles are uniformly distributed within the at least one or more film matrices.

67. The film delivery system according to claim 1, wherein the nanoparticles are distributed within said one of matrices such that the percent by weight variance of nanoparticles or peptide carried by the nanoparticles per unit volume of film does not vary more than about 10%.

68. The film delivery system of claim 67, wherein the permeation or penetration enhancing agent is selected from the group consisting of medium chain mono and diacylglycerol fatty acid derivatives, synthetic and natural surfactants, medium chain fatty acids and salts and esters thereof, bile salts, chelating agents, detergents, phospholipids, lecithins, cetomacrogels, glycerol and polyalkylene glycols and their esters, salicylates, polysorbates, alkylsulfoxides, alkanols, fatty acids and their corresponding esters and alcohols, urea and cyclic ureas, pyrrolidone derivatives, alkyl and cyclic amides, anionic surfactants, cationic surfactants, non-ionic surfactants, ketones, alkyl oxides, cycloalkene oxides, oils, alkyl glycosides, zonula occuludens, alcohols, and combinations thereof.

69. The film delivery system according to claim 67, wherein the permeation enhancing agent is coupled to the nanoparticle core and/or the nanoparticle corona.

70. The film delivery system according to claim 1, wherein the total water content is about 10% or less by weight of the delivery system.

71. The film delivery system according to claim 1, wherein the nanoparticles are incorporated or deposited on the surface of the one or more film matrices.

72. The film delivery system according to claim 1, further comprising a permeation and/or penetration enhancing agent.

73. The film delivery system according to claim 1, wherein the nanoparticles are distributed in the film such that the percent weight of nanoparticles or active carried by the nanoparticle per unit volume does not vary by more than about ten percent.

74. The film delivery system according to claim 1, wherein said film is divided into individual films of approximately equal size, and wherein the amount by weight of nanoparticles of individual films has a variance of no more than about ten percent between individual films.

* * * * *